US012611311B2

(12) United States Patent
Marks et al.

(10) Patent No.: US 12,611,311 B2
(45) Date of Patent: Apr. 28, 2026

(54) METATARSAL ARTHROPLASTY DEVICES, SYSTEMS, AND METHODS

(71) Applicant: Extremity Innovations, Inc., Aiken, SC (US)

(72) Inventors: Richard Marks, Mobile, AL (US); Arley Perez, III, Wayne, NJ (US)

(73) Assignee: Extremity Innovations, Inc., Aiken, SC (US)

( * ) Notice: Subject to any disclaimer, the term of this patent is extended or adjusted under 35 U.S.C. 154(b) by 710 days.

(21) Appl. No.: 18/084,514

(22) Filed: Dec. 19, 2022

(65) Prior Publication Data

US 2023/0190485 A1 Jun. 22, 2023

Related U.S. Application Data

(60) Provisional application No. 63/291,363, filed on Dec. 18, 2021.

(51) Int. Cl.
*A61F 2/42* (2006.01)
*A61B 17/16* (2006.01)
(Continued)

(52) U.S. Cl.
CPC ........ *A61F 2/4225* (2013.01); *A61B 17/1682* (2013.01); *A61F 2/30767* (2013.01);
(Continued)

(58) Field of Classification Search
CPC .... A61F 2/4606; A61F 2/4225; A61F 2/4607; A61F 2/461; A61F 2/4612; A61F 2/4605; A61B 17/1775; A61B 17/1717
See application file for complete search history.

(56) References Cited

U.S. PATENT DOCUMENTS

| | | | |
|---|---|---|---|
| 4,156,296 A | 5/1979 | Johnson et al. | |
| 4,211,228 A * | 7/1980 | Cloutier | A61F 2/389 |
| | | | 606/88 |

(Continued)

FOREIGN PATENT DOCUMENTS

| | | |
|---|---|---|
| AU | 2004201647 B2 | 8/2010 |
| CN | 112402067 A | 2/2021 |

(Continued)

*Primary Examiner* — Alvin J Stewart
(74) *Attorney, Agent, or Firm* — David Meibos; Maywood IP Law

(57) ABSTRACT

Implants, systems, instruments, methods, and kits for metatarsophalangeal joint arthroplasty may include metatarsal arthroplasty implants, repositioning guides, broach tools, inserter tools, and sterilizable packaging configured to facilitate metatarsal arthroplasty surgical procedures. The metatarsal arthroplasty implants may generally include an articular member having a convex articular surface, a concave bone-facing surface opposite the convex articular surface, and at least one side surface intermediate the convex articular surface and the concave bone-facing surface, as well as a central shaft sized for insertion into a metatarsal bone having a central shaft longitudinal axis, a central shaft proximal end coupled to the concave bone-facing surface of the articular member, and a central shaft distal end extending away from the concave bone-facing surface of the articular member along the central shaft longitudinal axis.

18 Claims, 29 Drawing Sheets

(51) Int. Cl.
    *A61F 2/30*        (2006.01)
    *A61F 2/46*        (2006.01)
    *A61B 17/92*       (2006.01)

(52) U.S. Cl.
    CPC .............. *A61F 2/46* (2013.01); *A61F 2/4606*
        (2013.01); *A61B 2017/922* (2013.01); *A61F*
        *2002/30131* (2013.01); *A61F 2002/30224*
        (2013.01); *A61F 2002/30245* (2013.01); *A61F*
        *2002/30299* (2013.01); *A61F 2002/30326*
        (2013.01); *A61F 2002/30327* (2013.01); *A61F*
        *2002/30614* (2013.01); *A61F 2002/3069*
        (2013.01); *A61F 2002/30841* (2013.01); *A61F*
        *2002/30878* (2013.01); *A61F 2002/30879*
        (2013.01); *A61F 2002/30904* (2013.01); *A61F*
        *2002/30934* (2013.01); *A61F 2002/4233*
        (2013.01); *A61F 2002/4622* (2013.01); *A61F*
        *2002/4681* (2013.01)

(56)             References Cited

U.S. PATENT DOCUMENTS

| | | | |
|---|---|---|---|
| 4,385,404 A | 5/1983 | Sully et al. | |
| 4,642,122 A | 2/1987 | Steffee | |
| 4,728,330 A | 3/1988 | Comparetto | |
| 4,787,908 A | 11/1988 | Wyss et al. | |
| 4,908,031 A | 3/1990 | Frisch | |
| 5,007,932 A | 4/1991 | Bekki et al. | |
| 5,037,440 A | 8/1991 | Koenig | |
| 5,207,712 A | 5/1993 | Cohen | |
| 5,314,486 A | 5/1994 | Zang | |
| 5,326,366 A | 7/1994 | Pascarella | |
| 5,458,648 A | 10/1995 | Berman | |
| 5,462,549 A * | 10/1995 | Glock ................... | A61F 2/4684 |
| | | | 606/88 |
| 5,683,466 A | 11/1997 | Vitale | |
| 5,725,585 A | 3/1998 | Zobel | |
| 5,776,203 A | 7/1998 | Spalding | |
| 5,895,388 A | 4/1999 | Zobel | |
| 6,007,580 A | 12/1999 | Lehto | |
| 6,319,284 B1 | 11/2001 | Rushdy | |
| 7,128,763 B1 | 10/2006 | Blatt | |
| 7,175,667 B2 | 2/2007 | Saunders et al. | |
| 7,291,175 B1 | 11/2007 | Gordon | |
| 7,473,259 B2 * | 1/2009 | Jacobs ............... | A61B 17/0482 |
| | | | 606/148 |
| 7,641,695 B2 | 1/2010 | Guederian | |
| 7,909,880 B1 | 3/2011 | Grant | |
| 8,147,559 B2 | 4/2012 | Tallarida | |
| 8,292,966 B2 | 10/2012 | Morton | |
| 8,353,965 B2 | 1/2013 | Seitz, Jr. | |
| 8,491,663 B2 | 7/2013 | Lindner | |
| 8,647,390 B2 | 2/2014 | Bellemere | |
| 8,652,211 B1 | 2/2014 | Jerry, Jr. | |
| 8,764,842 B2 | 7/2014 | Graham | |
| 8,845,750 B2 | 9/2014 | Slavitt | |
| 8,876,901 B2 | 11/2014 | Strzepa | |
| 8,900,318 B2 | 12/2014 | Linares | |
| 9,044,332 B2 | 6/2015 | Goswami et al. | |
| 9,132,019 B2 | 9/2015 | Weems | |
| 9,504,581 B2 | 11/2016 | Parrott | |
| 9,554,916 B2 | 1/2017 | Miller | |
| 10,064,631 B2 | 9/2018 | Dacosta | |
| 10,098,749 B2 | 10/2018 | Jefferis | |
| 10,517,742 B2 | 12/2019 | Long | |
| 10,617,528 B2 | 4/2020 | Lauf | |
| 11,051,946 B2 | 7/2021 | Vitale | |
| 11,058,545 B2 | 7/2021 | Carioscia | |
| 11,083,587 B2 | 8/2021 | Sikora | |
| 11,123,196 B1 | 9/2021 | Zink | |
| 11,160,664 B2 | 11/2021 | Cavanagh | |
| 11,273,045 B2 * | 3/2022 | Montross ............. | A61F 2/4606 |
| 11,382,759 B2 | 7/2022 | Bailey | |
| 2006/0074492 A1 | 4/2006 | Frey | |

| | | | |
|---|---|---|---|
| 2006/0100715 A1 | 5/2006 | de Villiers | |
| 2006/0247787 A1 | 11/2006 | Rydell | |
| 2010/0185295 A1 | 7/2010 | Emmanuel | |
| 2011/0082561 A1 | 4/2011 | Forrester | |
| 2011/0125277 A1 | 5/2011 | Nygren | |
| 2012/0022656 A1 | 1/2012 | Lavi | |
| 2012/0065738 A1 | 3/2012 | Schulman | |
| 2012/0179268 A1 | 7/2012 | Hollawell | |
| 2012/0259312 A1 * | 10/2012 | Iannotti .................. | A61B 17/88 |
| | | | 604/173 |
| 2012/0259335 A1 * | 10/2012 | Scifert ............... | A61B 17/1767 |
| | | | 623/20.35 |
| 2012/0259419 A1 * | 10/2012 | Brown .............. | A61B 17/1682 |
| | | | 623/21.19 |
| 2013/0231744 A1 | 9/2013 | Taylor | |
| 2014/0188238 A1 | 7/2014 | Sander | |
| 2014/0316530 A1 | 10/2014 | Early | |
| 2016/0030196 A1 * | 2/2016 | Eraly .................... | A61F 2/4612 |
| | | | 606/96 |
| 2016/0151076 A1 * | 6/2016 | Bake .................... | A61F 2/4684 |
| | | | 606/80 |
| 2017/0100251 A1 | 4/2017 | Ek et al. | |
| 2018/0036142 A1 | 2/2018 | Wahl | |
| 2018/0103967 A1 * | 4/2018 | Rouyer ............. | A61B 17/1659 |
| 2019/0142598 A1 | 5/2019 | Koenig | |
| 2019/0183660 A1 * | 6/2019 | Loring ................. | A61F 2/4657 |
| 2019/0274696 A1 * | 9/2019 | Goble ............... | A61B 17/155 |
| 2020/0078185 A1 * | 3/2020 | Marks ............... | A61F 2/42 |
| 2020/0085592 A1 * | 3/2020 | Oh ........................ | A61F 2/4684 |
| 2020/0107937 A1 | 4/2020 | Denham | |
| 2020/0197183 A1 | 6/2020 | Nutter | |
| 2020/0246147 A2 | 8/2020 | Schwartz | |
| 2021/0022879 A1 * | 1/2021 | Hollis ................. | A61B 17/151 |
| 2021/0059829 A1 * | 3/2021 | Montross ............. | A61F 2/4225 |
| 2021/0113222 A1 * | 4/2021 | Khatibi ................. | A61B 17/15 |
| 2021/0121297 A1 | 4/2021 | Cavanagh et al. | |
| 2021/0290319 A1 * | 9/2021 | Poltaretskyi ......... | G02B 27/017 |
| 2021/0298771 A1 * | 9/2021 | Lee ........................ | A61B 17/15 |
| 2021/0378686 A1 * | 12/2021 | Sikora ............... | A61B 17/1778 |
| 2022/0249239 A1 | 8/2022 | Williams | |
| 2022/0313277 A1 * | 10/2022 | Hissong ............... | A61B 17/14 |
| 2022/0346965 A1 | 11/2022 | Schwartz | |
| 2022/0370211 A1 * | 11/2022 | Campbell ............ | A61B 17/151 |
| 2022/0387178 A1 * | 12/2022 | Reynolds ............ | A61F 2/30734 |
| 2023/0000498 A1 * | 1/2023 | Amiot ................. | A61B 17/863 |
| 2023/0092178 A1 * | 3/2023 | Campbell .......... | A61B 17/8866 |
| | | | 606/87 |
| 2023/0149045 A1 * | 5/2023 | Sayger .............. | A61B 17/1775 |
| | | | 606/60 |
| 2023/0165616 A1 * | 6/2023 | Sayger .............. | A61B 17/1682 |
| | | | 602/30 |
| 2023/0190306 A1 * | 6/2023 | Kowalczyk ......... | A61F 2/30767 |
| | | | 623/18.11 |
| 2023/0190484 A1 * | 6/2023 | Marks ............... | A61B 17/1682 |
| | | | 623/16.11 |
| 2023/0255784 A1 * | 8/2023 | Parekh .................. | A61F 2/4225 |
| | | | 606/96 |
| 2023/0301644 A1 * | 9/2023 | Coyne .................... | A61B 17/66 |
| 2023/0301669 A1 * | 9/2023 | Wagner ............. | A61B 17/8061 |
| 2023/0310013 A1 * | 10/2023 | Perler .................. | A61B 17/66 |
| | | | 606/87 |
| 2023/0371966 A1 * | 11/2023 | Spitler .............. | A61B 17/8866 |
| 2023/0389973 A1 * | 12/2023 | Hartson ............ | A61B 17/1682 |
| 2024/0024129 A1 * | 1/2024 | Metcalfe ............ | A61B 17/1778 |
| 2024/0041609 A1 * | 2/2024 | Penninger ............ | A61F 2/4081 |
| 2024/0099778 A1 * | 3/2024 | Hlad .................. | A61B 17/1775 |
| 2024/0108363 A1 * | 4/2024 | Nader ............... | A61B 17/1728 |
| 2024/0206890 A1 * | 6/2024 | Gargac ................. | A61F 2/4081 |
| 2024/0237980 A1 * | 7/2024 | Niver ................. | A61B 17/0682 |
| 2024/0268966 A1 * | 8/2024 | Spitler .............. | A61F 2/30942 |
| 2024/0325154 A1 * | 10/2024 | Ryd .................. | A61B 17/1775 |
| 2024/0335205 A1 * | 10/2024 | Pressacco ............. | A61F 2/4612 |
| 2025/0000525 A1 * | 1/2025 | Korman .............. | A61B 17/151 |
| 2025/0017604 A1 * | 1/2025 | Dewey ................. | A61B 17/809 |
| 2025/0049449 A1 * | 2/2025 | DiGeorgio ............. | A61B 17/15 |
| 2025/0049450 A1 * | 2/2025 | Dogué .............. | A61B 17/1775 |
| 2025/0072910 A1 * | 3/2025 | Orphanos ......... | A61B 17/1778 |
| 2025/0114209 A1 * | 4/2025 | Korman ................. | A61F 2/4606 |

(56) References Cited

U.S. PATENT DOCUMENTS

| | | | | |
|---|---|---|---|---|
| 2025/0143720 A1 * | 5/2025 | Wagner | .............. | A61B 17/8897 |
| 2025/0160855 A1 * | 5/2025 | Dacosta | ............. | A61B 17/1775 |
| 2025/0195081 A1 * | 6/2025 | Scanlan | ................ | A61B 34/10 |
| 2025/0241694 A1 * | 7/2025 | Blacklidge | ............ | A61F 2/4225 |
| 2025/0241696 A1 * | 7/2025 | Barnes | .............. | A61B 17/8057 |
| 2025/0268611 A1 * | 8/2025 | Neichel | .............. | A61F 2/30734 |

FOREIGN PATENT DOCUMENTS

| | | | | | |
|---|---|---|---|---|---|
| CN | 113425470 A | 9/2021 | | | |
| CN | 113425472 A | 9/2021 | | | |
| DE | 3017798 C2 | 10/1983 | | | |
| DE | 29807414 | 9/1998 | | | |
| DE | 10358307 A1 | 6/2006 | | | |
| EP | 0201651 B1 | 4/1990 | | | |
| EP | 1977720 A1 * | 10/2008 | ............ | A61F 2/461 |
| FR | 2465470 A1 | 3/1981 | | | |
| FR | 2645735 B1 | 2/1993 | | | |
| FR | 2697155 B1 | 12/1994 | | | |
| FR | 2709948 B1 | 11/1995 | | | |
| FR | 2722979 B1 | 1/1997 | | | |
| FR | 2724311 B1 | 1/1997 | | | |
| FR | 2728783 B1 | 9/1999 | | | |
| FR | 2803509 B1 | 7/2002 | | | |
| FR | 2926212 B1 | 3/2010 | | | |
| FR | 3022137 A1 * | 12/2015 | ......... | A61B 17/1682 |
| FR | 3057454 A1 * | 4/2018 | ......... | A61B 17/1684 |
| WO | WO9416638 | 8/1994 | | | |
| WO | WO1996005784 A1 | 2/1996 | | | |
| WO | WO9637169 A1 | 11/1996 | | | |
| WO | WO0035381 A1 | 6/2000 | | | |
| WO | WO2001003613 A1 | 1/2001 | | | |
| WO | WO2006099886 A1 | 9/2006 | | | |
| WO | WO2009073924 A1 | 6/2009 | | | |
| WO | WO2014068210 A1 | 5/2014 | | | |
| WO | WO-2015105880 A1 * | 7/2015 | ......... | A61B 17/1728 |
| WO | WO-2016149635 A1 * | 9/2016 | .......... | A61B 17/164 |
| WO | WO2017097906 A1 | 6/2017 | | | |
| WO | WO2022192250 A1 | 9/2022 | | | |
| WO | WO-2023244867 A1 * | 12/2023 | ............ | G06F 30/27 |
| WO | WO-2024168331 A1 * | 8/2024 | ......... | A61B 17/1775 |

* cited by examiner

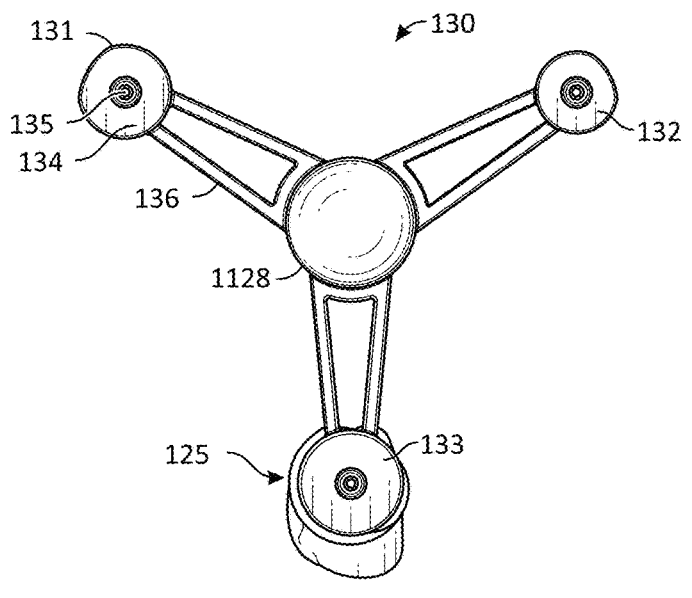
FIG. 3A
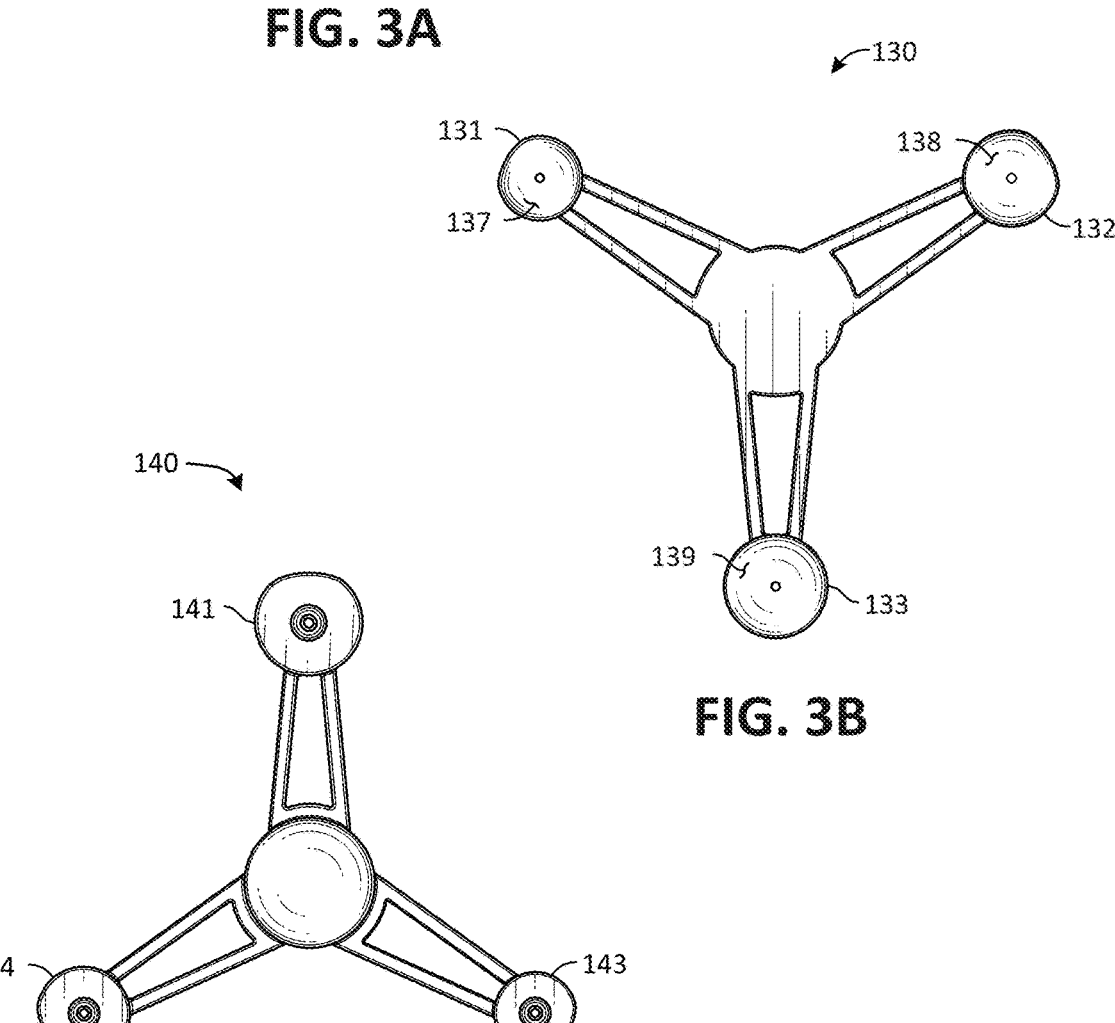
FIG. 3B
FIG. 4

130

125

135

150

130

125

145

150

142

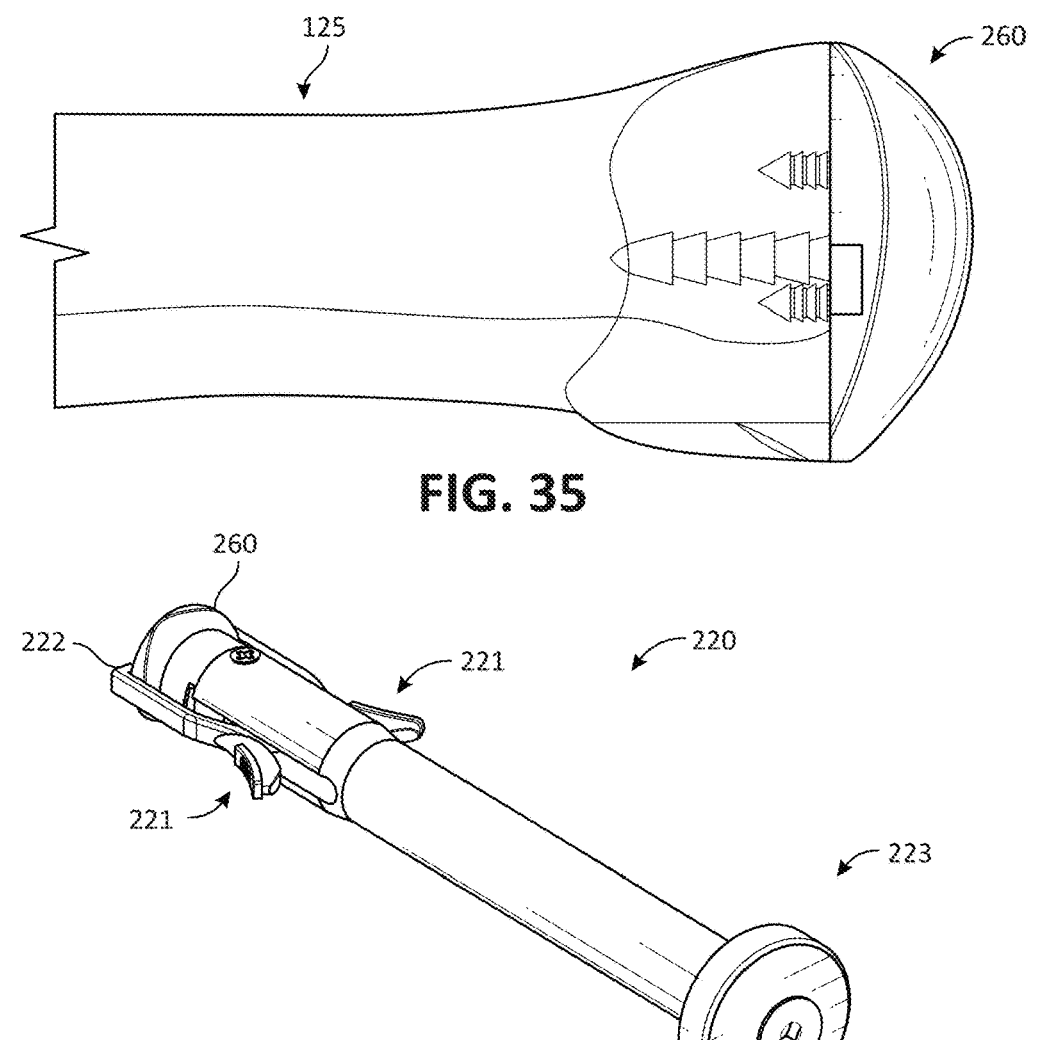
FIG. 35
FIG. 36
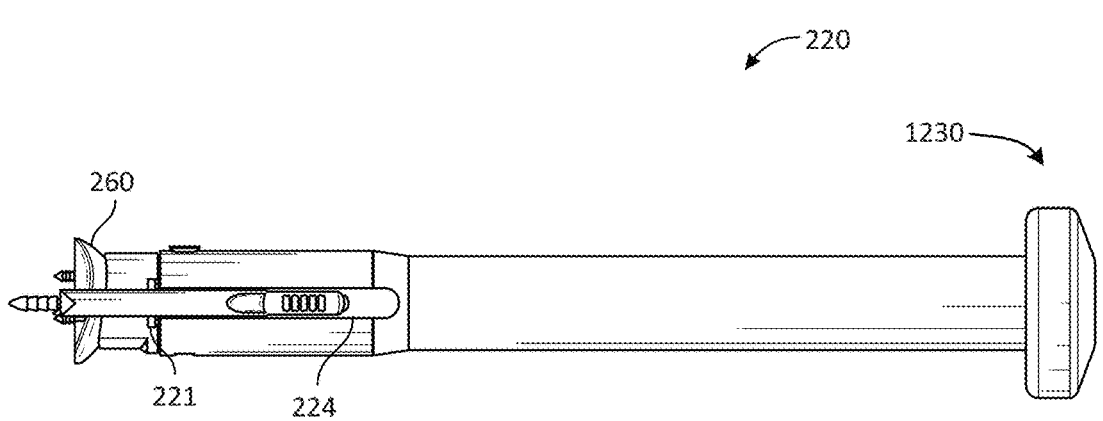
FIG. 37

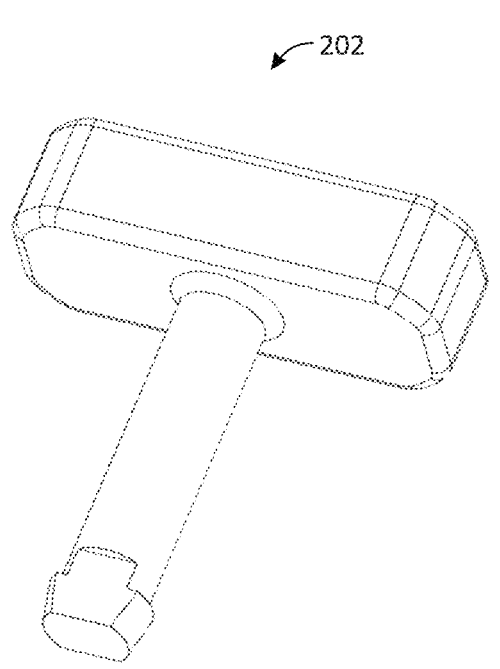
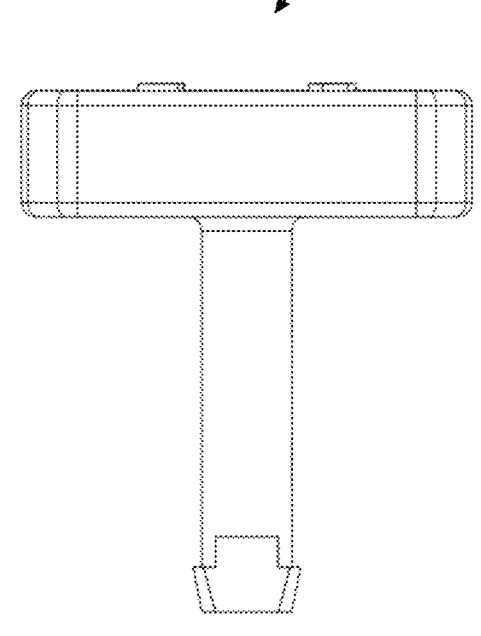
FIG. 44A
FIG. 44B
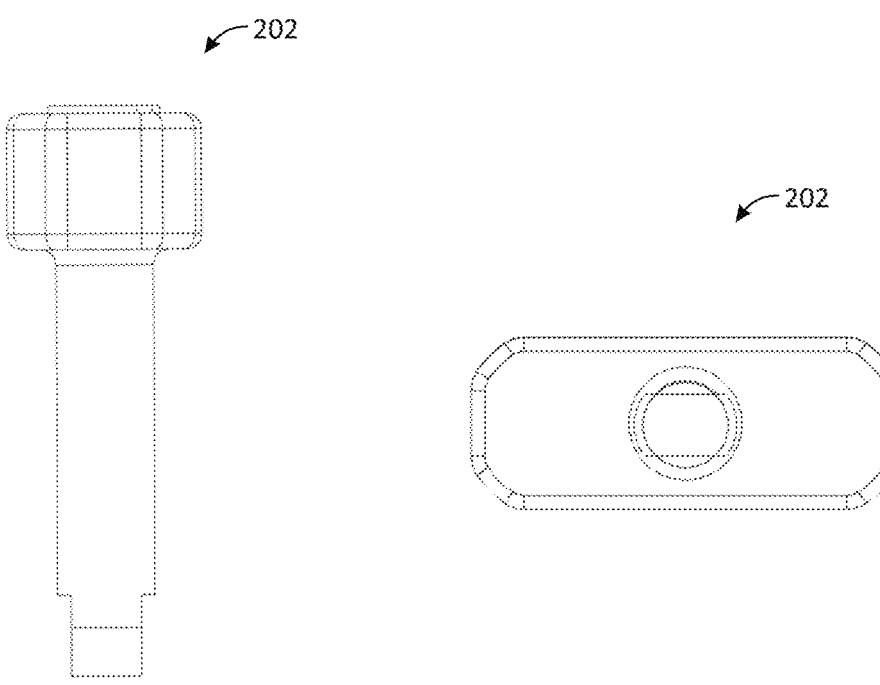
FIG. 44C
FIG. 44D

FIG. 45A          FIG. 45B          FIG. 45C

METATARSAL ARTHROPLASTY DEVICES, SYSTEMS, AND METHODS

CROSS-REFERENCE TO RELATED APPLICATIONS

The present application claims the benefit of U.S. Provisional Patent Application Ser. No. 63/291,363, entitled FIRST METATARSAL ARTHROPLASTY IMPLANT SYSTEMS AND METHODS, which was filed on Dec. 18, 2021. The foregoing document is incorporated by reference as though set forth herein in its entirety.

TECHNICAL FIELD

The present disclosure relates generally to the field of orthopedic and podiatric surgery. More particularly, the present disclosure relates to the treatment of arthritis of the big toe joint or limited dorsiflexion (hallux rigidus) of the first metatarsophalangeal (MTP) joint, as well as surgical treatment of the lesser metatarsophalangeal joints due to dorsal osteophyte impingement or arthritis. However, it will also be understood that the implants, systems, instruments, and methods disclosed herein can be adapted for utilization on any bone or within any type of joint arthroplasty procedure.

BACKGROUND

Arthritis of the big toe is the most common arthritic condition of the foot and is second only to bunions (hallux valgus) as a condition associated with the big toe. The true cause of hallux rigidus is not known, although several risk factors such as an abnormally long or elevated first foot bone (metatarsal), differences in foot anatomy, prior traumatic injury to the big toe, or family history are believed to be contributing factors. Hallux rigidus is typically diagnosed by physical examination of the joint by a physician. This examination includes manipulation of the metatarsophalangeal (MTP) joint and examination of the foot for evidence of bone spurs. Medical imaging may also be used to help understand the extent of joint degeneration and to show the location and size of bone spurs.

Treatment of hallux rigidus typically consists of non-surgical therapy that includes anti-inflammatory medications, heat or ice, orthotics, and injections. Surgical options are determined by the failure of the non-surgical therapy and the extent of the arthritis located in the MTP joint. Common surgical options for hallux rigidus and arthritis of the first MTP joint may include decompression (cheilectomy), partial joint resection (resection arthroplasty), fusion (arthrodesis) of the first MTP joint, joint replacement and arthroplasty (partial joint replacement). However, these surgical interventions all involve risks, difficulties, and/or other drawbacks. Accordingly, there is a need for improved hallux rigidus implants, systems, instruments, and methods.

SUMMARY

The various systems and methods of the present disclosure have been developed in response to the present state of the art, and in particular, in response to the problems and needs in the art that have not yet been fully solved by currently available metatarsal treatment systems and methods. The systems and methods of the present disclosure may provide metatarsal arthroplasty implants and instruments for extremities including but not limited to the first MTP joint, lesser MTP joints, etc. The instruments may include, but are not limited to, one or more sizing templates, repositioning guides, reamers, step drills, broach tools, trial devices, inserters, etc. These instruments may facilitate enhanced bone fixation with minimal bone removal from a metatarsal head.

In some embodiments, a system for performing a metatarsal arthroplasty surgical procedure may include a repositioning guide configured to guide placement of a metatarsal arthroplasty implant on a metatarsal bone. The repositioning guide may include a repositioning guide body having a first guide pin hole configured to receive a first guide pin placed in the metatarsal bone at a first location and a first angle, and a second guide pin hole configured to receive one of: a second guide pin placed through the second guide pin hole and into the metatarsal bone at a second location and a second angle to guide placement of the metatarsal arthroplasty implant on the metatarsal bone with respect to the second location and the second angle, and the first guide pin repositioned through the second guide pin hole and into the metatarsal bone at a third location and a third angle to guide placement of the metatarsal arthroplasty implant on the metatarsal bone with respect to the third location and the third angle.

In some embodiments of the system, the metatarsal arthroplasty implant may include an articular member having a convex articular surface, a concave bone-facing surface opposite the convex articular surface, and at least one side surface intermediate the convex articular surface and the concave bone-facing surface. The metatarsal arthroplasty implant may also include a central shaft sized for insertion into the metatarsal bone having a central shaft longitudinal axis, a central shaft proximal end coupled to the concave bone-facing surface of the articular member, and a central shaft distal end extending away from the concave bone-facing surface of the articular member along the central shaft longitudinal axis.

In some embodiments of the system, the repositioning guide body may include an offset guide portion comprising an offset concave surface configured to abut the metatarsal bone, the first guide pin hole may include a central guide pin hole, and the second guide pin hole may include one or more peripheral holes arranged about the central guide pin hole.

In some embodiments of the system, the one or more peripheral holes may include four peripheral holes arranged about the central guide pin hole and configured to guide the second guide pin into the metatarsal bone at the second location and the second angle, parallel to the first guide pin.

In some embodiments of the system, the repositioning guide body may include an angular guide portion having an angular concave surface configured to abut the metatarsal bone, the second guide pin hole may include an attachment guide pin hole spaced apart from the first guide pin hole and configured to guide the second guide pin into the metatarsal bone at the second location and the second angle to secure the angular guide portion to the metatarsal bone, and the first guide pin hole may include an angular guide pin hole having an oval shape configured to guide repositioning of the first guide pin through the angular guide pin hole and into the metatarsal bone at the third location and the third angle, non-parallel to an initial placement of the first guide pin in the metatarsal bone at the first location and the first angle.

In some embodiments of the system, the angular guide portion may also include one or more angle markings configured to indicate a relative change in angular position between the first angle and the third angle.

In some embodiments of the system, the repositioning guide body may include an offset guide portion and an angular guide portion, wherein the offset guide portion and the angular guide portion may be coupled to each other via one or more connecting arms intermediate the offset guide portion and the angular guide portion.

In some embodiments, a system for performing a metatarsal arthroplasty surgical procedure may include a repositioning guide configured to guide placement of a metatarsal arthroplasty implant on a metatarsal bone. The repositioning guide may include a repositioning guide body having a first guide pin hole configured to receive a first guide pin placed in the metatarsal bone at a first location and a first angle. The first guide pin hole may be elongated to permit adjustment of at least one of: a sagittal orientation of the first guide pin in the metatarsal bone with respect to the first location and the first angle, and a medial-lateral orientation of the first guide pin in the metatarsal bone with respect to the first location and the first angle.

In some embodiments of the system, the metatarsal arthroplasty implant may include an articular member having a convex articular surface, a concave bone-facing surface opposite the convex articular surface, and at least one side surface intermediate the convex articular surface and the concave bone-facing surface. The metatarsal arthroplasty implant may also include a central shaft sized for insertion into the metatarsal bone having a central shaft longitudinal axis, a central shaft proximal end coupled to the concave bone-facing surface of the articular member, and a central shaft distal end extending away from the concave bone-facing surface of the articular member along the central shaft longitudinal axis.

In some embodiments of the system, the first guide pin hole may include an angular guide pin hole having an oval shape configured to guide repositioning of the first guide pin through the angular guide pin hole and into the metatarsal bone to adjust the sagittal orientation of the first guide pin in the metatarsal bone at a second angle, non-parallel to the first angle.

In some embodiments of the system, the repositioning guide body may also include an attachment guide pin hole spaced apart from the first guide pin hole and configured to guide a second guide pin into the metatarsal bone at a second location and a second angle, parallel to the first angle, to secure the repositioning guide body to the metatarsal bone.

In some embodiments of the system, with the first guide pin removed from the first guide pin hole, the repositioning guide body may be rotatable about the second guide pin to adjust the medial-lateral orientation of the first guide pin repositioned through the first guide pin hole and into the metatarsal bone at a third location and a third angle.

In some embodiments of the system, the third angle may be parallel to the first angle.

In some embodiments of the system, the third angle may be non-parallel to the first angle.

In some embodiments, a system for performing a metatarsal arthroplasty surgical procedure may include a repositioning guide configured to guide placement of a metatarsal arthroplasty implant on a metatarsal bone. The repositioning guide may include a repositioning guide body having an offset guide portion and an angular guide portion. The offset guide portion may include a first guide pin hole configured to receive a first guide pin placed in the metatarsal bone at a first location and a first angle, and a first plurality of guide pin holes configured to guide repositioning of the first guide pin at a second location and a second angle that is parallel to the first angle. The angular guide portion may include one or more guide pin holes configured to receive the first guide pin placed in the metatarsal bone at the first location and the first angle and guide repositioning of the first guide pin to a third location and a third angle non-parallel to the first angle.

In some embodiments of the system, the metatarsal arthroplasty implant may include an articular member having a convex articular surface, a concave bone-facing surface opposite the convex articular surface, and at least one side surface intermediate the convex articular surface and the concave bone-facing surface. The metatarsal arthroplasty implant may also include a central shaft sized for insertion into the metatarsal bone having a central shaft longitudinal axis, a central shaft proximal end coupled to the concave bone-facing surface of the articular member, and a central shaft distal end extending away from the concave bone-facing surface of the articular member along the central shaft longitudinal axis.

In some embodiments of the system, the offset guide portion may include an offset concave surface configured to abut the metatarsal bone, the first guide pin hole may include a central guide pin hole configured to receive the first guide pin placed in the metatarsal bone at the first location and the first angle, and the first plurality of guide pin holes may be arranged about the central guide pin hole and configured to guide repositioning of the first guide pin at the second location and the second angle that is parallel to the first angle.

In some embodiments of the system, the angular guide portion may include an angular concave surface configured to abut the metatarsal bone, and the one or more guide pin holes may include an angular guide pin hole having an oval shape that may be configured to receive the first guide pin placed in the metatarsal bone at the first location and the first angle and guide repositioning of the first guide pin to the third location and the third angle non-parallel to the first angle.

In some embodiments of the system, the angular guide portion may also include one or more angle markings configured to indicate a relative change in angular position between the third angle non-parallel to the first angle.

In some embodiments of the system, the offset guide portion and the angular guide portion may be coupled to each other via one or more connecting arms intermediate the offset guide portion and the angular guide portion.

These and other features and advantages of the present disclosure will become more fully apparent from the following description and appended claims or may be learned by the practice of the systems and methods set forth hereinafter.

BRIEF DESCRIPTION OF THE DRAWINGS

Exemplary embodiments of the disclosure will become more fully apparent from the following description and appended claims, taken in conjunction with the accompanying drawings. Understanding that these drawings depict only exemplary embodiments and are, therefore, not to be considered limiting of the scope of the appended claims, the exemplary embodiments of the present disclosure will be described with additional specificity and detail through use of the accompanying drawings in which:

FIG. 3A is a front view of a sizing guide placed on a metatarsal head, according to an embodiment of the present disclosure;

FIG. 3B is a back view of the sizing guide shown in FIG. 3A;

FIG. 4 is a front view of a sizing guide, according to another embodiment of the present disclosure;

FIG. 35 is a side view of the metatarsal arthroplasty implant of FIG. 30A fully seated in a metatarsal bone;

FIG. 36 is a perspective view of an inserter tool coupled to the metatarsal arthroplasty implant of FIG. 30A;

FIG. 37 is a side view of FIG. 36;

FIG. 44A is a perspective view of a retention pin of the broach tool shown in FIG. 43;

FIG. 44B is a front view of the retention pin;

FIG. 44C is a side view of the retention pin;

FIG. 44D is a bottom view of the retention pin;

Figures 45A, 45B, 45C:
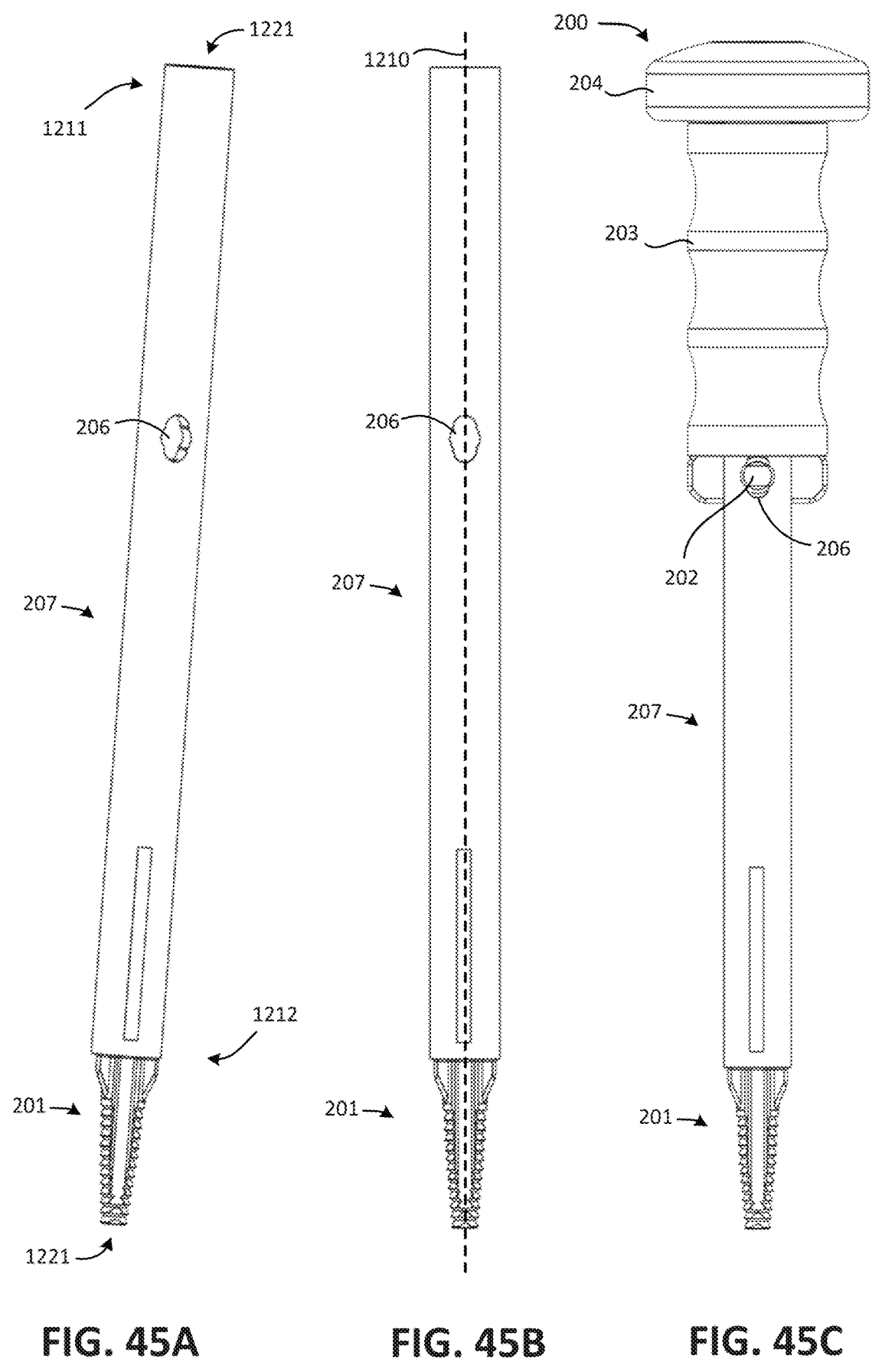

FIG. 45A is a perspective view of a broach tool shaft of the broach tool shown in FIG. 43;

FIG. 45B is a side view of the broach tool shaft;

FIG. 45C is a bottom view of the broach tool; and

Figure 1A:
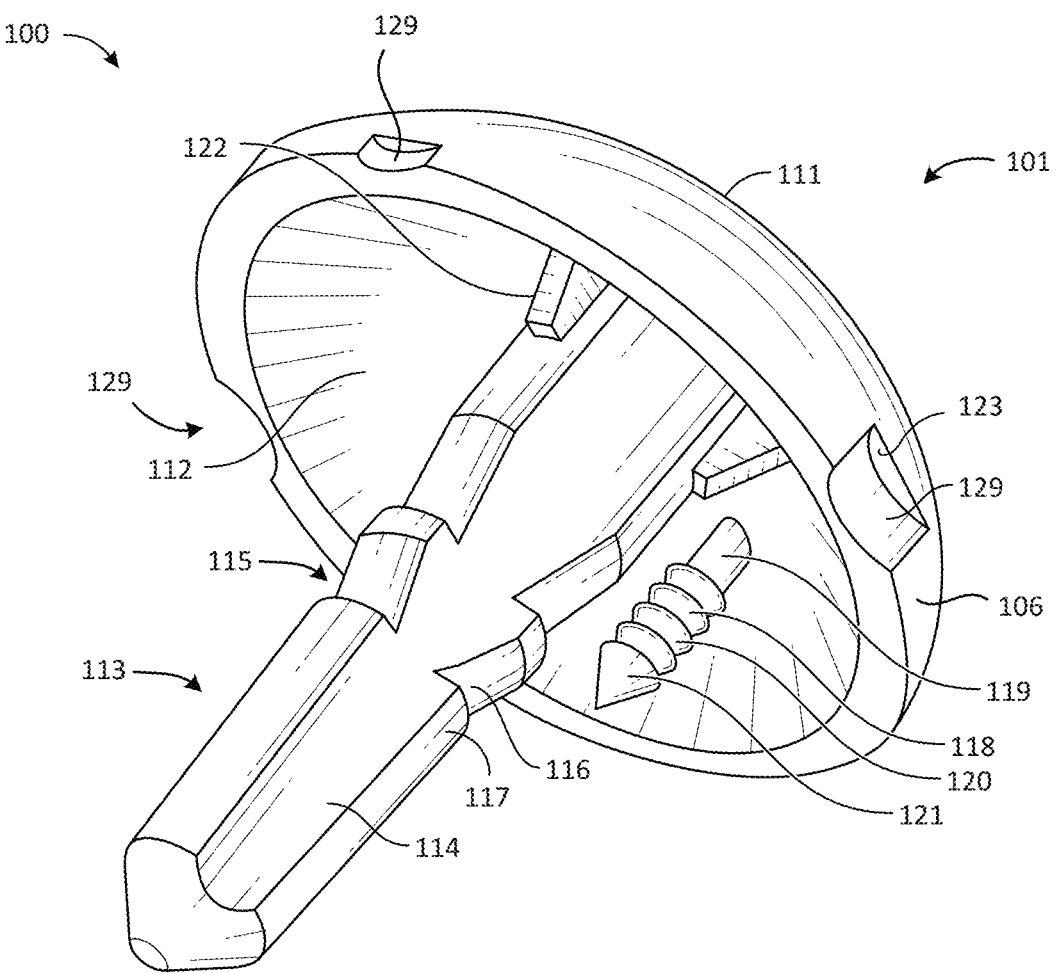
FIG. 1A is a perspective view of a metatarsal arthroplasty implant, according to an embodiment of the present disclosure.

It is to be understood that the drawings are for purposes of illustrating the concepts of the present disclosure and may not be drawn to scale. Furthermore, the drawings illustrate exemplary embodiments and do not represent limitations to the scope of the present disclosure.

DETAILED DESCRIPTION

Exemplary embodiments of the present disclosure will be best understood by reference to the drawings, wherein like parts are designated by like numerals throughout. It will be readily understood that the components of the present disclosure, as generally described and illustrated in the drawings, could be arranged, and designed in a wide variety of different configurations. Thus, the following more detailed description of the embodiments of the devices, systems, and methods, as represented in the drawings, is not intended to limit the scope of the present disclosure but is merely representative of exemplary embodiments of the present disclosure.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in the drawings, the drawings are not necessarily drawn to scale unless specifically indicated.

Standard medical planes of reference and descriptive terminology are employed in this specification. While these terms are commonly used to refer to the human body, certain terms are applicable to physical objects in general.

A standard system of three mutually perpendicular reference planes is employed. A sagittal plane divides a body into right and left portions. A coronal plane divides a body into anterior and posterior portions. A transverse plane divides a body into superior and inferior portions. A mid-sagittal, mid-coronal, or mid-transverse plane divides a body into equal portions, which may be bilaterally symmetric. The intersection of the sagittal and coronal planes defines a superior-inferior or cephalad-caudal axis. The intersection of the sagittal and transverse planes defines an anterior-posterior axis. The intersection of the coronal and transverse planes defines a medial-lateral axis. The superior-inferior or cephalad-caudal axis, the anterior-posterior axis, and the medial-lateral axis are mutually perpendicular.

Anterior means toward the front of a body. Posterior means toward the back of a body. Superior or cephalad means toward the head. Inferior or caudal means toward the feet or tail. Medial means toward the midline of a body, particularly toward a plane of bilateral symmetry of the body. Lateral means away from the midline of a body or away from a plane of bilateral symmetry of the body. Axial means toward a central axis of a body. Abaxial means away from a central axis of a body. Ipsilateral means on the same side of the body. Contralateral means on the opposite side of the body. Proximal means toward the trunk of the body. Proximal may also mean toward a user or operator. Distal means away from the trunk. Distal may also mean away from a user or operator. Dorsal means toward the top of the foot. Plantar means toward the sole of the foot. Varus means deviation of the distal part of the leg below the knee inward, resulting in a bowlegged appearance. Valgus means deviation of the distal part of the leg below the knee outward, resulting in a knock-kneed appearance.

FIGS. 1A-2 and 19-21 illustrate various views of a metatarsal arthroplasty implant or implant 100, according to an embodiment of the present disclosure. In some embodiments, the implant 100 may be designed to replace a natural joint engaging surface and articulate with a proximal phalanx. As the anatomy of patients may vary, the implant 100 may include a plurality of sizes, all with the same general profile and features.

In one embodiment, the implant 100 may have a convex articular surface or convex outer surface 111 and a concave bone-facing surface or concave inner surface 112. The concave inner surface 112 may couple with a central shaft or stem 113 extending therefrom. In some embodiments, the stem 113 may include a conical member with a constant thickness, or may decrease in thickness along the length thereof, and/or may include one or more longitudinal grooves or one or more flutes 114 extending along the length of the stem 113. The one or more flutes 114 may limit the rotational movement of the implant 100 after implantation in a metatarsal bone or metatarsal 125. In some embodiments, the stem 113 may also include at least one barb or radial grooves 115 that may be designed to prevent the implant 100 from backing out of the metatarsal 125 after implantation. Each of the radial grooves 115 may have a first leading angle 116 and a second trailing angle 117.

In some embodiments, the first leading angle 116 may be within the range of 0° to 45° from a central shaft longitudinal axis 107 or axis of the stem 113. More specifically, the first leading angle 116 may be within a range of 10° to 35° from the axis of the stem 113. Yet more specifically, the first leading angle 116 may be within a range of 20° to 25° from the axis of the stem 113. Still more specifically, the first leading angle 116 may be approximately 22.5° from the axis of the stem 113.

In some embodiments, the second trailing angle 117 may be within a range of 60° to 120° from the axis of the stem 113. More specifically, the second trailing angle 117 may be within a range of 75° to 105° from the axis of the stem 113. Yet more specifically, the second trailing angle 117 may be within a range of 85° to 95° from the axis of the stem 113. Still more specifically, the second trailing angle 117 may be approximately 90° from the axis of the stem 113.

Additionally, the concave inner surface 112 may include at least one anti-rotation pin or one or more spikes 119 protruding therefrom having anti-rotation pin proximal end 127 and an anti-rotation pin distal end 128. One spike 119 is shown in FIG. 1A, but in alternative embodiments, any number of spikes 119 may be present, and the spikes 119 may be distributed along the concave inner surface 112. Such distribution may or may not be along a radially symmetrical pattern. Each of the spikes 119 may be proximate the outer edge of the concave inner surface 112, closer to the stem 113, or positioned anywhere along the radius of the concave inner surface 112. This disclosure encompasses the use of 1, 2, 3, 4, 5, 6, 7, 8, 9, or more spikes 119. The spike 119 may optionally have a generally circular cross-section such that the centerline or anti-rotation pin longitudinal axis 276 of the spike 119 may be parallel to the centerline or central shaft longitudinal axis 107 of the stem 113. Further, the spike 119 may include at least one anti-rotation pin barb or a plurality of radial grooves 118. Each of the plurality of radial grooves 118 may have a first leading angle 120 and a second trailing angle 121.

In some embodiments, the implant 100 may include at least one rib member or one or more rib sections 122 connecting the stem 113 to the concave inner surface 112. The one or more rib sections 122 may provide additional support for the stem 113 to help avoid bending of the stem 113 relative to the concave inner surface 112. The one or more rib sections 122 may also engage with the bone as the implant 100 is implanted to help prevent rotation on the implant 100 after implantation.

In some embodiments, the implant 100 may include at least one side surface 106 with a notch or a plurality of notches 129 formed therein comprising undercut surfaces or undercuts 123.

Figure 1B:
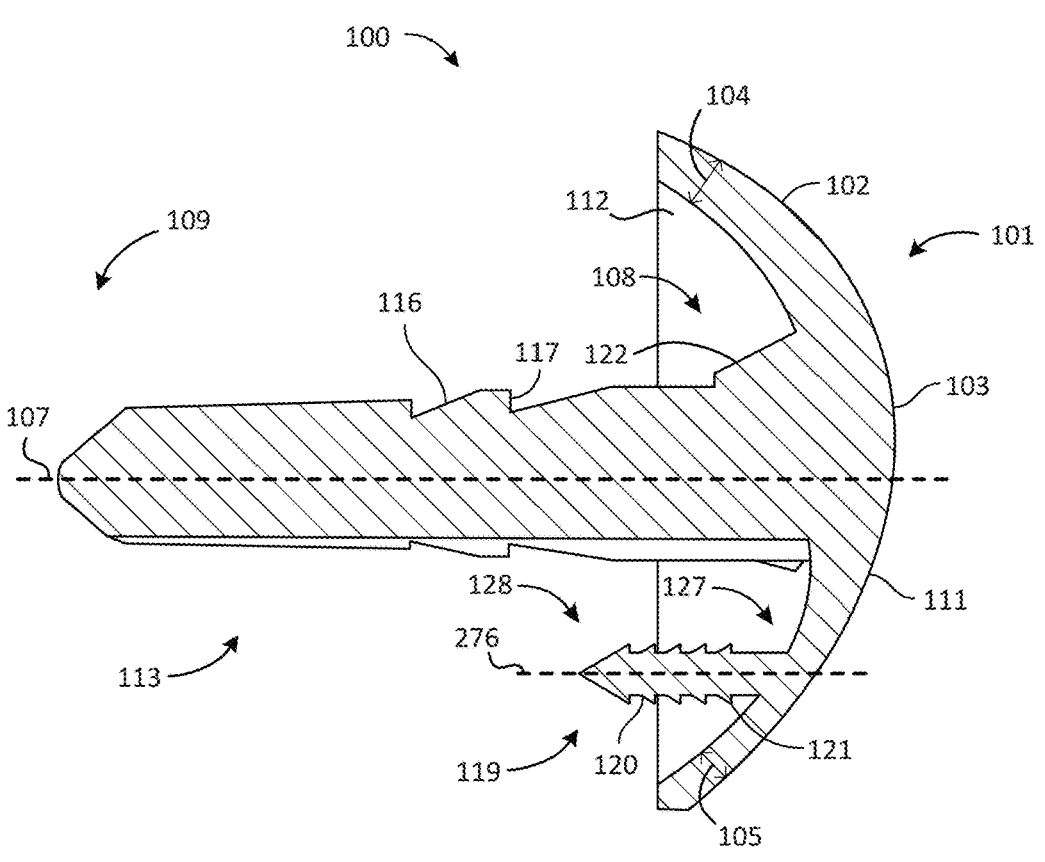
FIG. 1B is a cross-sectional side view of the metatarsal arthroplasty implant of FIG. 1A.

FIG. 1B is a section view of the implant 100. In one embodiment, the implant 100 may have the convex outer surface 111 that may be comprised of a first radius 102 and a second radius 103 that may be generally similar to the first radius 102 or may be generally different than the first radius 102. In some embodiments, the articular member 101 or head of the implant 100 may include a first thickness 105 that may be less than a second thickness 104. In some embodiments, the first radius 102 may be on the dorsal side of the implant 100, and the second radius 103 may be on the plantar side. This may cause the adjoining phalanx to rotate about a tighter arc when moving dorsally of a horizontal plane through the axis of the metatarsus. Additionally, or alternatively, this variable radius may help maintain stability of the joint under the desired amount of tension from surrounding ligaments and other soft tissues. The radius of the convex outer surface 111 may be continuously variable between the first radius 102 and the second radius 103. In the alternative, there may be a more abrupt transition in radius, from the first radius 102 to the second radius 103. In alternative embodiments, other variable radius schemes may be used. For example, a smaller radius could exist on the plantar, rather than the dorsal, side. Variable radius may be used between the left and right sides of the convex outer surface 111.

Figure 2:
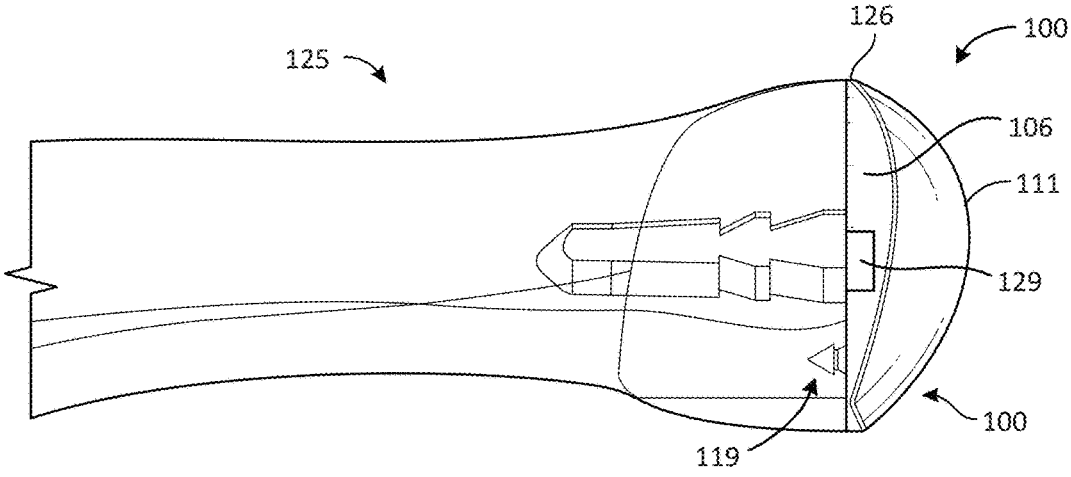
FIG. 2 is a side view of the metatarsal arthroplasty implant of FIG. 1A installed in a metatarsal bone.

FIG. 2 is a side view of the implant 100 fully seated in a metatarsal 125. In some embodiments, the rim 126 of the implant 100 may be generally aligned with the adjoining bony portion of the prepared metatarsal head, and the convex outer surface 111 may be positioned to articulate with the articulating surface of the phalanx (not shown) immediately distal to it.

In some embodiments, a metatarsal arthroplasty implant 100 may include an articular member 101, a central shaft 113 sized for insertion into a metatarsal bone 125, and at least one anti-rotation pin 119 spaced apart from the central shaft 113 and sized for insertion into the metatarsal bone 125 adjacent the central shaft 113. The articular member 101 may include a convex articular surface 111, a concave bone-facing surface 112 opposite the convex articular surface 111, and at least one side surface 106 intermediate the convex articular surface 111 and the concave bone-facing surface 112. The central shaft 113 may include a central shaft longitudinal axis 107, a central shaft proximal end 108 coupled to the concave bone-facing surface 112 of the articular member 101, and a central shaft distal end 109 extending away from the concave bone-facing surface 112 of the articular member 101 along the central shaft longitudinal axis 107. The at least one anti-rotation pin 119 may include an anti-rotation pin longitudinal axis 276, an anti-rotation pin proximal end 127 coupled to the concave bone-facing surface 112 of the articular member 101, an anti-rotation pin distal end 128 extending away from the concave bone-facing surface 112 of the articular member 101 along the anti-rotation pin longitudinal axis 276, and at least one barb 118 formed in the at least one anti-rotation pin 119 and shaped to resist removal of the at least one anti-rotation pin 119 from the metatarsal bone 125.

In some embodiments, the articular member 101 may also include a plurality of notches 129 formed in the at least one side surface 106 with undercut surfaces 123 extending below the convex articular surface 111 configured to facilitate installation and removal of the metatarsal arthroplasty implant 100 from the metatarsal bone 125, as will be discussed in more detail below.

In some embodiments, a length of the at least one anti-rotation pin 119 may be less than a length of the central shaft 113, and the anti-rotation pin longitudinal axis 276 may be substantially parallel to the central shaft longitudinal axis 107.

In some embodiments, the metatarsal arthroplasty implant 100 may also include at least one rib member 122 radially projecting away from a proximal portion 108 of the central shaft 113 and coupling with the concave bone-facing surface 112.

In some embodiments, a first cross-sectional length or diameter of the central shaft proximal end 108 may be greater than a second cross-sectional length or diameter of the central shaft distal end 109.

In some embodiments, the implant 100 may be intended to provide a replacement articulating surface of the metatarsal head and the implant 100 may be designed to articulate with the proximal phalanx. The implant 100 and one or more of the instruments disclosed herein may be provided to a clinician in a single use sterilized package or packaging and/or may be provided in a package that requires sterilization prior to use. The packages may include trays specifically designed to accommodate the implant 100 and instruments. The method for implantation may include one or more of the following steps: (1) Incision and exposure of the metatarsal; (2) Sizing of the metatarsal to determine optimal implant size; (3) Placement of a guide pin; (4) Fluoroscopic confirmation of guide pin position; (5) Repositioning of the guide pin (optional); (6) Reaming the metatarsal head so that the profile generally corresponds to the concave inner surface of the implant; (7) Drill into the medullary canal; (8) Form broach the medullary canal to generally match the implant stem profile; (9) Place trial implant and test range of motion of the joint; (10) If the joint is too tight, steps 6 through 9 above may be repeated; (11) Implant insertion; (12) Fluoroscopic confirmation of implant location; and/or (13) Close the incision.

FIG. 3A is a front view of a sizing guide 130 engaged with the metatarsal 125. The sizing guide 130 may include three sizing discs 131, 132, 133 connected to a central hub 1128 by connecting arms 136. Each of the three sizing discs 131, 132, 133 may be sized to correspond with potential sizes and/or profile shapes of various metatarsal heads. Each of the three sizing discs 131, 132, 133 may include a size indicator 134 (e.g., a size number, etc.) and a guide hole 135 designed to receive a guide pin 150 therethrough.

FIG. 3B is a back view of the sizing guide 130. Each of the three sizing discs 131, 132, 133 may include a concave surfaces 137, 138, 139, respectively. The concave surfaces 137, 138, 139 may generally correspond to a convex profile of an unresected metatarsal head.

FIG. 4 is a front view of another sizing guide 140 embodiment. This embodiment serves the same function as the sizing guide 130 but may be designed to correspond to a larger metatarsal head. The profiles of the three sizing discs 141, 143, 144 of the sizing guide 140 may be larger than the three sizing discs 131, 132, 133 of the sizing guide 130, and may be labeled accordingly.

In some embodiments, the sizing guides may include a plurality of sizing discs within a single instrument to allow a surgeon to engage a plurality of disc sizes with a single instrument to increase efficiency, facilitate the surgical procedure, and reduce costs.

The method may include an initial incision to expose the metatarsal head. The incision may be a dorsal longitudinal incision with the extensor halluces longus (EHL) swept laterally. The method may further include medial and lateral exposure of the joint, with care to preserve the collateral ligaments. Further, osteophytes may be resected dorsally, laterally, and/or medially, and the sesamoids may be mobilized (but may not be released).

Figure 5:
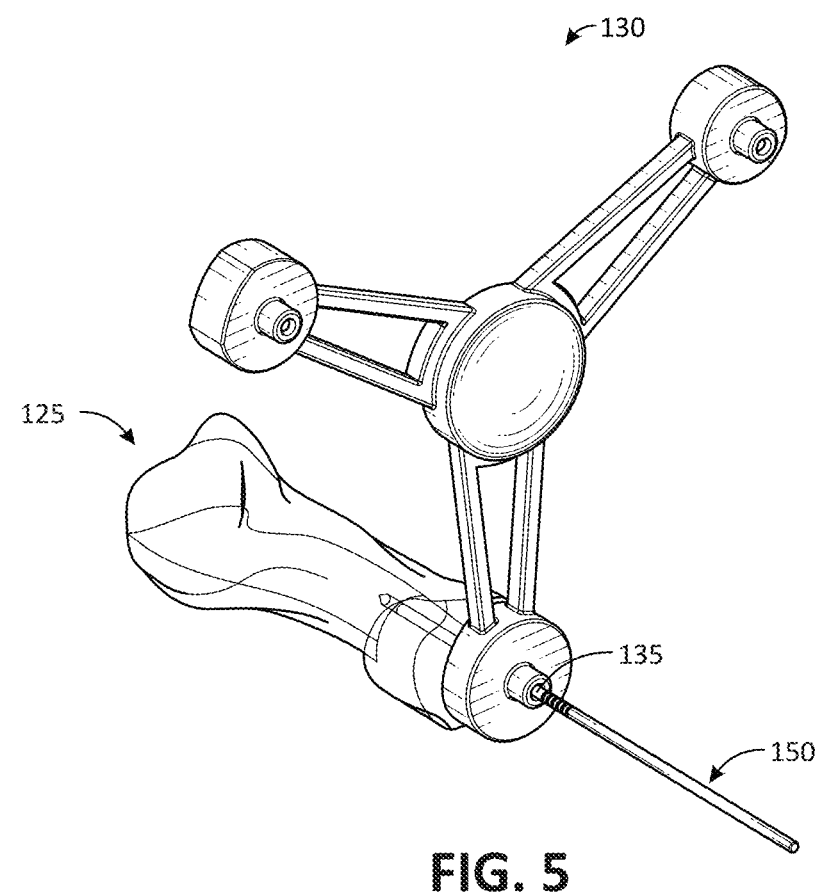
FIG. 5 is a perspective view of the sizing guide of FIG. 3A positioned on a metatarsal head.

FIG. 5 is a perspective view of the sizing guide 130 in position on a metatarsal 125 with a guide pin 150 in position within the metatarsal 125 through the guide hole 135.

The method may subsequently include sizing of the metatarsal head using a plurality sizing guides, as previously discussed. The sizing discs may be designed with a generally similar shape to a metatarsal head. In some embodiments, the sizing guides may include sizing discs within a range of about 14 mm to 24 mm, in 2 mm increments. The sizing discs may include concave surfaces which may generally correspond to the convex surface of the metatarsal head. The sizing guides may be used by placing a thumb on the central hub 1128 and centering the sizing disc on the metatarsal head with the concave surface of the sizing guide engaging the metatarsal head. Various sizes of the guide may be placed on the metatarsal head until the proper size is determined. The method may suggest that if the metatarsal head is between guide sizes, the smaller size may be selected.

The method may further include placement of a first guide pin or guide pin 150. The guide pin 150 may be inserted through the guide hole 135 formed through the center of each sizing disc. The guide hole 135 may facilitate location of the guide pin 150 centrally within the metatarsal head. The guide pin 150 may further include guide pin markings 142 to indicate an optimal insertion depth. The guide pin markings 142 may further include a plurality of indicators to correspond to various insertion depths. The sizing discs, guide pin 150, and guide pin markings 142 may all be designed in conjunction with each other such that the guide pin markings 142 on the guide pin 150 account for the thickness of the sizing discs and the depths that are marked may indicate the correct depth of the guide pin 150 placed into the metatarsal head.

Figure 6:
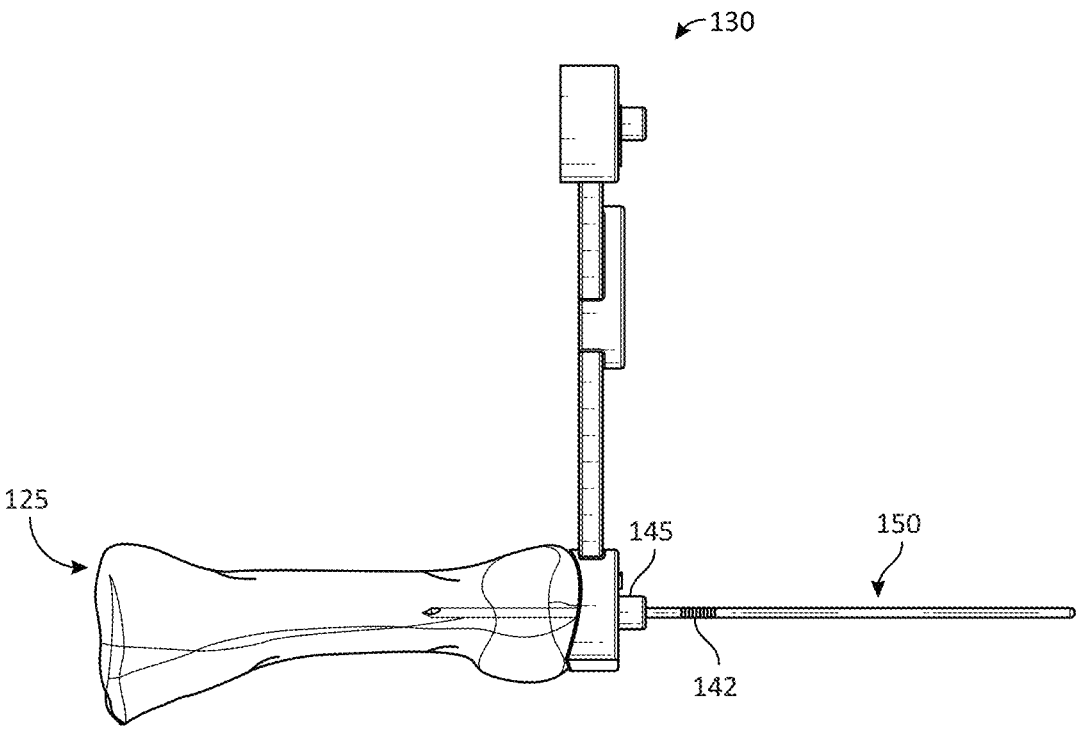
FIG. 6 is a side view of FIG. 5.

FIG. 6 is a side view of the sizing guide 130 in position on the metatarsal 125 with a guide pin 150 in position within the metatarsal 125 through the guide hole 135. The sizing guide 130 may further include a boss 145 around the guide hole 135 to provide better alignment of the guide pin 150 when inserting the guide pin 150 into the metatarsal 125.

The method may further include fluoroscopic confirmation of the position of the guide pin 150 within the metatarsal 125. The fluoroscopic confirmation may produce images to verify the guide pin 150 is centrally located on both the frontal (anterior-posterior) and/or sagittal (lateral) planes. The method may further suggest that if the fluoroscopic images do not verify that the guide pin 150 is centrally located in both planes, the guide pin 150 may be removed and reinserted to correct for the misplacement, as discussed below.

The method may include an optional step for repositioning the guide pin 150 if the location shown in the fluoroscopic images is not centrally located. Repositioning may be accomplished using a repositioning guide 160 specifically design for the method. The repositioning guide 160 may also be designed in conjunction with the guide pin 150 and the guide pin markings 142 such that the guide pin markings 142 on the guide pin 150 account for the thickness of the repositioning guide 160, and the depths that are marked indicate the correct depth of the guide pin 150 into the metatarsal head. The repositioning guide 160 may have slots for sagittal and/or medial-lateral adjustment. For medial-lateral adjustment, the targeting device may be placed over the guide pin 150 and a second guide pin 170 may be inserted in the desired adjustment hole. Rotation around the initial guide pin or guide pin 150 may also accommodate inferior-superior adjustments. Sagittal realignment may be achieved by utilizing a slotted portion of the repositioning guide.

Figures 7, 8, 9:
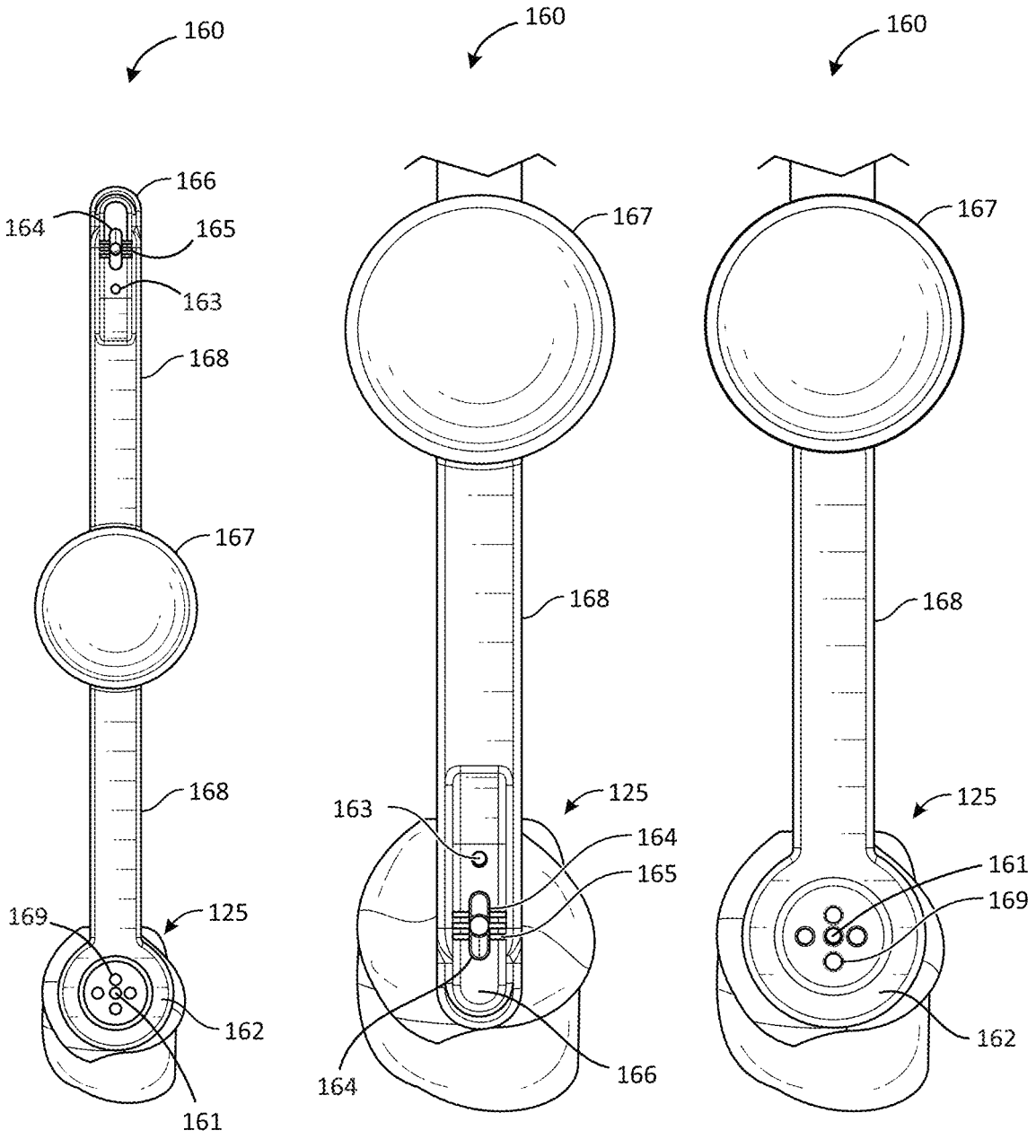
FIG. 7 is a front view of a repositioning guide placed on a metatarsal head, according to an embodiment of the present disclosure.
FIG. 8 is a close-up front view of a portion of the repositioning guide shown in FIG. 7.
FIG. 9 is a close-up front view of another portion of the repositioning guide shown in FIG. 7.

FIG. 7 is a front view the repositioning guide 160 engaged with the metatarsal 125. In some embodiments, the repositioning guide 160 may include a repositioning guide body 1170 having an offset guide portion or first end 162 for offset guide pin adjustments, and an angular guide portion 166 or second end 166 for rotational and/or angular adjustments. In some embodiments, these two ends may be connected via a repositioning guide central hub 167 by one or more connecting arms 168.

FIG. 8 is a close up view of the repositioning guide 160 with the second end 166 engaged with a metatarsal 125. The second end 166 may include an attachment guide pin hole or second guide pin hole 163 to allow the second guide pin 170 to be driven into the metatarsal 125. When the second guide pin 170 is inserted though the second guide pin hole 163, the first guide pin 150 may then be removed for repositioning. A generally oval shaped opening 164 (also referred to herein as a first guide pin hole or an angular guide pin hole) formed in the second end 166 of the repositioning guide 160 may facilitate sagittal and/or medial-lateral adjustment of the guide pin 150. Further the generally oval shaped opening 164 may also adjacently include length markings and/or angle markings 165 such that specific offset distances/angles may be achieved.

FIG. 9 is a close up view of the repositioning guide 160 with the first end 162 engaged with a metatarsal 125. In this configuration, the repositioning guide 160 may be advanced over the guide pin 150 placed within the metatarsal 125 through the central through hole 161 (the central through hole 161 may also be referred to herein as a central guide pin hole or a first guide pin hole). In some embodiments, the first end 162 of the repositioning guide 160 may include a plurality of additional through holes 169 (which may also be referred to herein as a second guide pin hole, one or more peripheral holes, or a first plurality of guide pin holes) that may be spaced apart from the central through hole 161. The plurality of additional through holes 169 may facilitate repositioning of the guide pin 150 offset from the central through hole 161 in the sagittal and/or medial-lateral planes.

Figure 10:
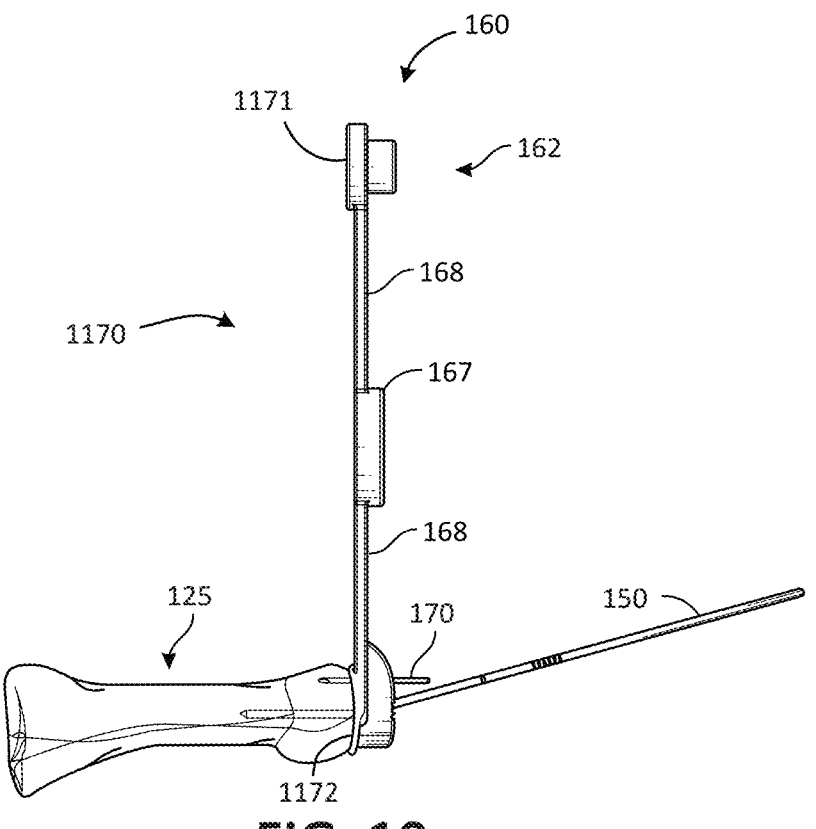
FIG. 10 is a side view of the repositioning guide shown in FIG. 8 with two guide pins placed in the metatarsal head.

FIG. 10 is a side view of the repositioning guide 160 with the second end 166 engaged with a metatarsal 125 and a second guide pin 170 placed in the metatarsal 125 through the repositioning guide 160. In some embodiments, the repositioning guide 160 may include an offset concave surface 1171 and/or an angular concave surface 1172 for engaging the metatarsal 125. In some embodiments, the guide pin 150 may be repositioned and driven back into the metatarsal 125 in a new location utilizing the generally oval shaped opening 164.

Figure 11:
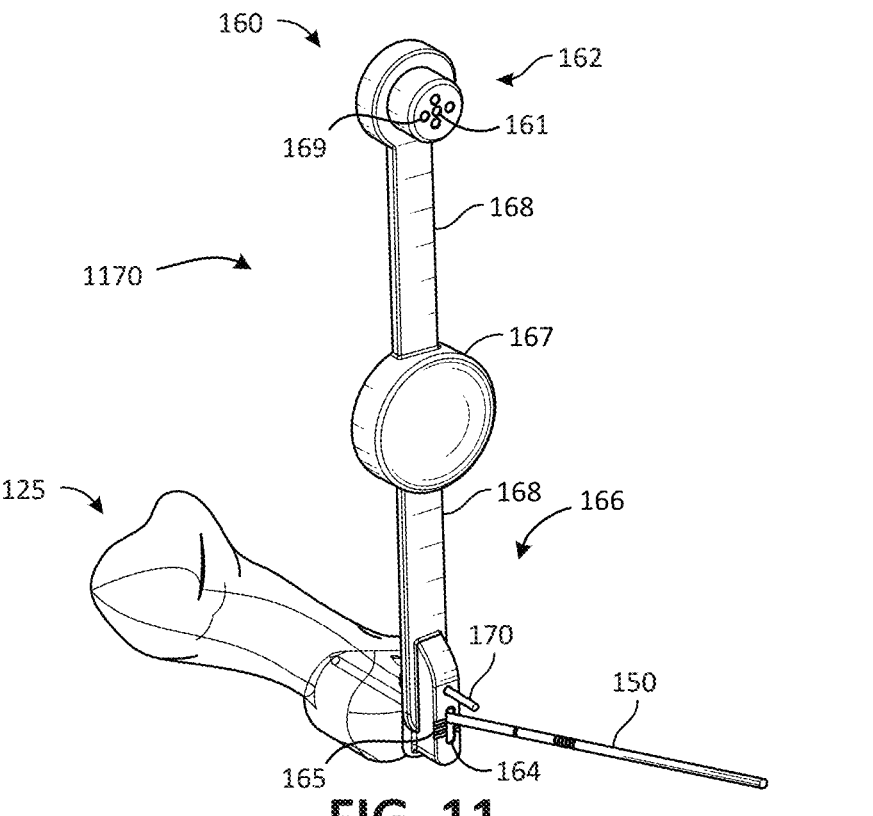
FIG. 11 is a perspective view of FIG. 10.

FIG. 11 is a perspective view of the repositioning guide 160 with the second end 166 engaged with the metatarsal 125 and the second guide pin 170 engaged with the metatarsal 125 through the repositioning guide 160. In some embodiments, a 0.045″ diameter second guide pin 170 may be used to stabilize the repositioning guide 160. The guide pin 150 (for example, a K-wire) placement may be positioned 180 degrees opposite the direction of repositioning (e.g., if a more dorsal trajectory is required for the guide pin 150, the second guide pin 170 may be placed at the 12 o'clock position, allowing the guide pin insertion site to drop opposite the second guide pin 170). In some embodiments, about 15 degrees of sagittal redirection of the guide pin 150 may be achieved. In some embodiments, the possible angular range may be designed to be between about 10 degrees and 20 degrees. Following repositioning, a repeat fluoroscopic verification image may be obtained in both the frontal (anterior-posterior) and/or sagittal (lateral) planes.

In some embodiments, a system for performing a metatarsal arthroplasty surgical procedure may include a repositioning guide 160 configured to guide placement of a metatarsal arthroplasty implant on a metatarsal bone 125. The repositioning guide 160 may include a repositioning guide body 1170 having a first guide pin hole configured to receive a first guide pin 150 placed in the metatarsal bone 125 at a first location and a first angle, and a second guide pin hole configured to receive one of: a second guide pin 170 placed through the second guide pin hole and into the metatarsal bone 125 at a second location and a second angle to guide placement of the metatarsal arthroplasty implant on the metatarsal bone 125 with respect to the second location and the second angle, and the first guide pin 150 repositioned through the second guide pin hole and into the metatarsal bone 125 at a third location and a third angle to guide placement of the metatarsal arthroplasty implant on the metatarsal bone 125 with respect to the third location and the third angle.

In some embodiments of the system, the repositioning guide body 1170 may include an offset guide portion 162 comprising an offset concave surface 1171 configured to abut the metatarsal bone 125, the first guide pin hole may include a central guide pin hole 161, and the second guide pin hole may include one or more peripheral holes 169 arranged about the central guide pin hole 161.

In some embodiments of the system, the one or more peripheral holes 169 may include four peripheral holes arranged about the central guide pin hole 161 and configured to guide the second guide pin 170 into the metatarsal bone at the second location and the second angle, parallel to the first guide pin 150.

In some embodiments of the system, the repositioning guide body 1170 may include an angular guide portion 166 having an angular concave surface 1172 configured to abut the metatarsal bone 125, the second guide pin hole may be an attachment guide pin hole 163 spaced apart from the first guide pin hole and configured to guide the second guide pin into the metatarsal bone 125 at the second location and the second angle to secure the angular guide portion 166 to the metatarsal bone 125, and the first guide pin hole may include an angular guide pin hole 164 having an oval shape configured to guide repositioning of the first guide pin 150 through the angular guide pin hole 164 and into the metatarsal bone 125 at the third location and the third angle, non-parallel to an initial placement of the first guide pin 150 in the metatarsal bone 125 at the first location and the first angle.

In some embodiments of the system, the angular guide portion 166 may also include one or more angle markings 165 configured to indicate a relative change in angular position between the first angle and the third angle.

In some embodiments of the system, the repositioning guide body 1170 may include an offset guide portion 162 and an angular guide portion 166, wherein the offset guide portion 162 and the angular guide portion 166 may be coupled to each other via one or more connecting arms 168 intermediate the offset guide portion 162 and the angular guide portion 166.

In some embodiments, a system for performing a metatarsal arthroplasty surgical procedure may include a repositioning guide 160 configured to guide placement of a metatarsal arthroplasty implant on a metatarsal bone 125. The repositioning guide 160 may include a repositioning guide body 1170 having a first guide pin hole 164 configured to receive a first guide pin 150 placed in the metatarsal bone 125 at a first location and a first angle. The first guide pin hole 164 may be elongated to permit adjustment of at least one of: a sagittal orientation of the first guide pin 150 in the metatarsal bone 125 with respect to the first location and the first angle, and a medial-lateral orientation of the first guide pin 150 in the metatarsal bone 125 with respect to the first location and the first angle.

In some embodiments of the system, the first guide pin hole 164 may be an angular guide pin hole 164 having an oval shape configured to guide repositioning of the first guide pin 150 through the angular guide pin hole 164 and into the metatarsal bone 125 to adjust the sagittal orientation of the first guide pin 150 in the metatarsal bone at a second angle, non-parallel to the first angle.

In some embodiments of the system, the repositioning guide body may also include an attachment guide pin hole 163 spaced apart from the first guide pin hole 164 and configured to guide a second guide pin 170 into the metatarsal bone 125 at a second location and a second angle, parallel to the first angle, to secure the repositioning guide body 1170 to the metatarsal bone 125.

In some embodiments of the system, with the first guide pin 150 removed from the first guide pin hole 164, the repositioning guide body 1170 may be rotatable about the second guide pin 170 to adjust the medial-lateral orientation of the first guide pin 150 that may then be repositioned through the first guide pin hole 164 and into the metatarsal bone 125 at a third location and a third angle.

In some embodiments of the system, the third angle may be parallel to the first angle.

In some embodiments of the system, the third angle may be non-parallel to the first angle.

In some embodiments, a system for performing a metatarsal arthroplasty surgical procedure may include a repositioning guide 160 configured to guide placement of a metatarsal arthroplasty implant on a metatarsal bone 125. The repositioning guide 160 may include a repositioning guide body 1170 having an offset guide portion 162 and an angular guide portion 166. The offset guide portion 162 may include a first guide pin hole 161 configured to receive a first guide pin 150 placed in the metatarsal bone at a first location and a first angle, and a first plurality of guide pin holes 169 configured to guide repositioning of the first guide pin 150 at a second location and a second angle that is parallel to the first angle. The angular guide portion 166 may include one or more guide pin holes 164 configured to receive the first guide pin 150 placed in the metatarsal bone 125 at the first location and the first angle and guide repositioning of the first guide pin 150 to a third location and a third angle non-parallel to the first angle.

In some embodiments of the system, the offset guide portion 162 may include an offset concave surface 1171 configured to abut the metatarsal bone 125, the first guide pin hole 161 may be a central guide pin hole 161 configured to receive the first guide pin 150 placed in the metatarsal bone 125 at the first location and the first angle, and the first plurality of guide pin holes 169 may be arranged about the central guide pin hole 161 and configured to guide repositioning of the first guide pin 150 at the second location and the second angle that is parallel to the first angle.

In some embodiments of the system, the angular guide portion 166 may include an angular concave surface 1172 configured to abut the metatarsal bone 125, and the one or more guide pin holes 164 may include an angular guide pin hole 164 having an oval shape that may be configured to receive the first guide pin 150 placed in the metatarsal bone 125 at the first location and the first angle and guide repositioning of the first guide pin 150 to the third location and the third angle non-parallel to the first angle.

Continuing with FIGS. 12-21, the method may further include selecting a reamer 180 that corresponds to a selected sizing disc. The reamer 180 may be placed over the guide pin 150 and advanced towards the bone 125. The reamer 180 may be size specific and packaged in a corresponding tray that may also contain a trial device 210, an inserter device 220, an implant, etc. The cutting edge 181 of the reamer 180 may be designed with a concave profile that may be generally similar in shape and dimensions to the concave inner surface of the implants disclosed herein. The reamer 180 may further include a window 182 in its shaft that may reveal laser etched (or otherwise formed) guide pin markings 142 on the guide pin 150. In the area of the window 182, the reamer shaft may further include a laser etched (or otherwise formed) radial indication mark 184 that may be alignable with the guide pin markings 142 on the guide pin 150 to indicate that the reamer 180 has cut to a corresponding depth into the metatarsal head. By aligning the radial indication mark 184 on the shaft of the reamer 180 with the guide pin markings 142 of the guide pin 150, the depth of the guide pin 150 placed into the bone 125 and/or the cutting depth of the reamer 180 may be controlled relative to each other. This may minimize the amount of bone removed for proper implant placement. In some embodiments, initial reaming may be performed at a 2-3 mm depth into the metatarsal head, depending on required bone decompression. Following reaming, a rongeur (not shown) may be used to remove peripheral bone. Particular attention may be given to circumferential decompression to avoid residual impingement in all directions.

Figure 12:
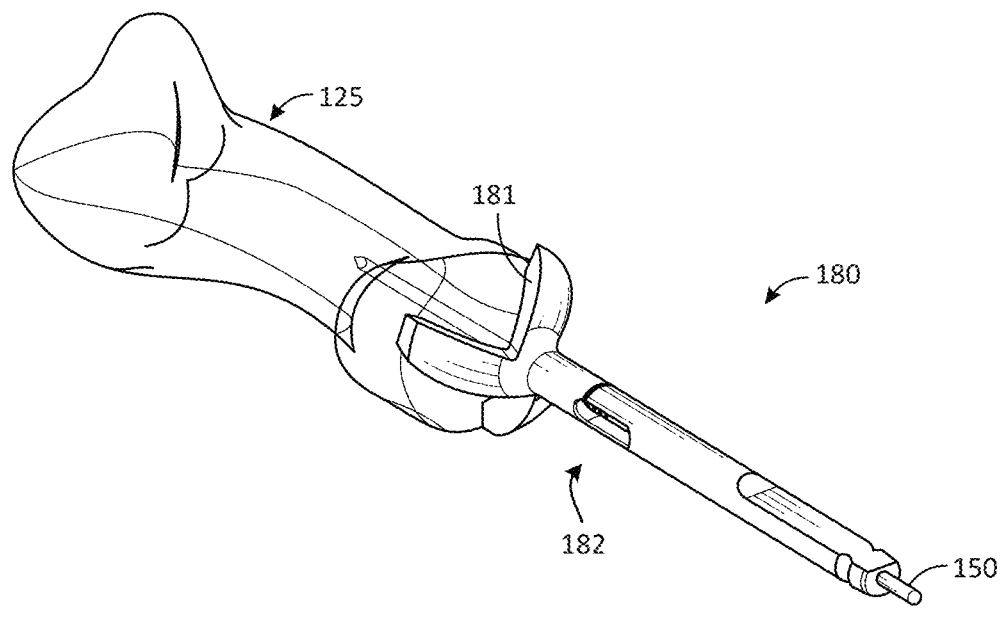
FIG. 12 is a perspective view of a reamer placed on a metatarsal head, according to an embodiment of the present disclosure.

FIG. 12 is a perspective view of the reamer 180 engaged with the metatarsal 125 over the guide pin 150. The reamer 180 may have a cutting edge 181 designed with a concave profile that is generally similar in shape and dimensions to the concave inner surface 112 of the implant 100. The reamer 180 may have a plurality of sizes, each with the cutting edge 181 corresponding to implant 100 sizes that may be determined via engagement of the sizing guides.

Figure 13:
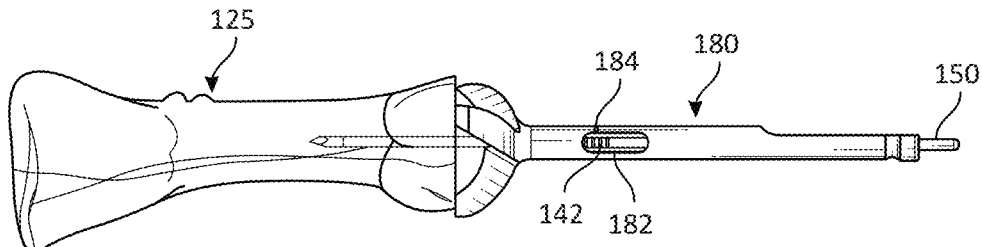
FIG. 13 is a side view of FIG. 12.
Figure 14:
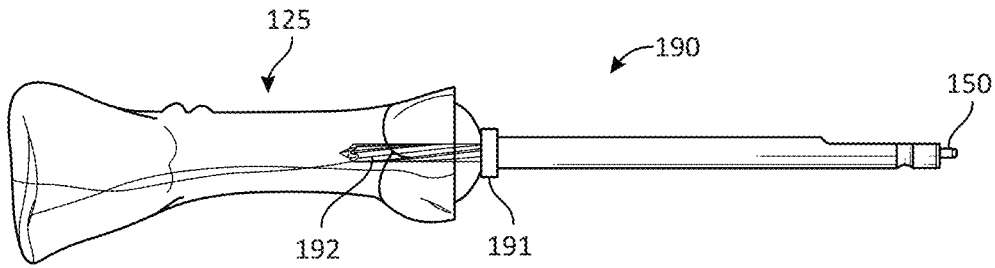
FIG. 14 is a side view of a drill bit inside a metatarsal head, according to an embodiment of the present disclosure.

FIG. 13 is a side view of the reamer 180 engaged with the metatarsal 125 over the guide pin 150. As can be seen, the guide pin 150 is visible through the window 182 when the reamer 180 is advanced over the guide pin 150. The radial indication mark 184 may be aligned with guide pin markings 142 on the guide pin 150 when the reamer 180 cuts to a corresponding depth into the metatarsal 125.

The method may then utilize a drill bit 190 placed over the guide pin 150 and advanced in the direction of the bone 125 to cut a cylindrical hole. In some embodiments, the drill bit 190 may be designed for use with all implant sizes. In some embodiments, the drill bit 190 may include a cutting diameter 192 that may be between about 2.0 mm and 4.0 mm in length. In some embodiments, the cutting diameter 192 may be about 2.7 mm in length. In some embodiments, the drill bit 190 may be designed with a step 209 or other feature along its shaft that may act as a depth stop 191. The depth stop 191 may ensure that the drill does not drill too deep into the metatarsal head. The depth stop 191 may be located such that the drill depth is between about 18 mm and 25 mm in length, or more specifically 21.5 mm in certain embodiments. In some embodiments, the depth stop 191 may result in a hole that is about 0.5 mm and 4.0 mm deeper than the stem 113 of the implant 100 intended to sit within the bone 125.

Figure 15:
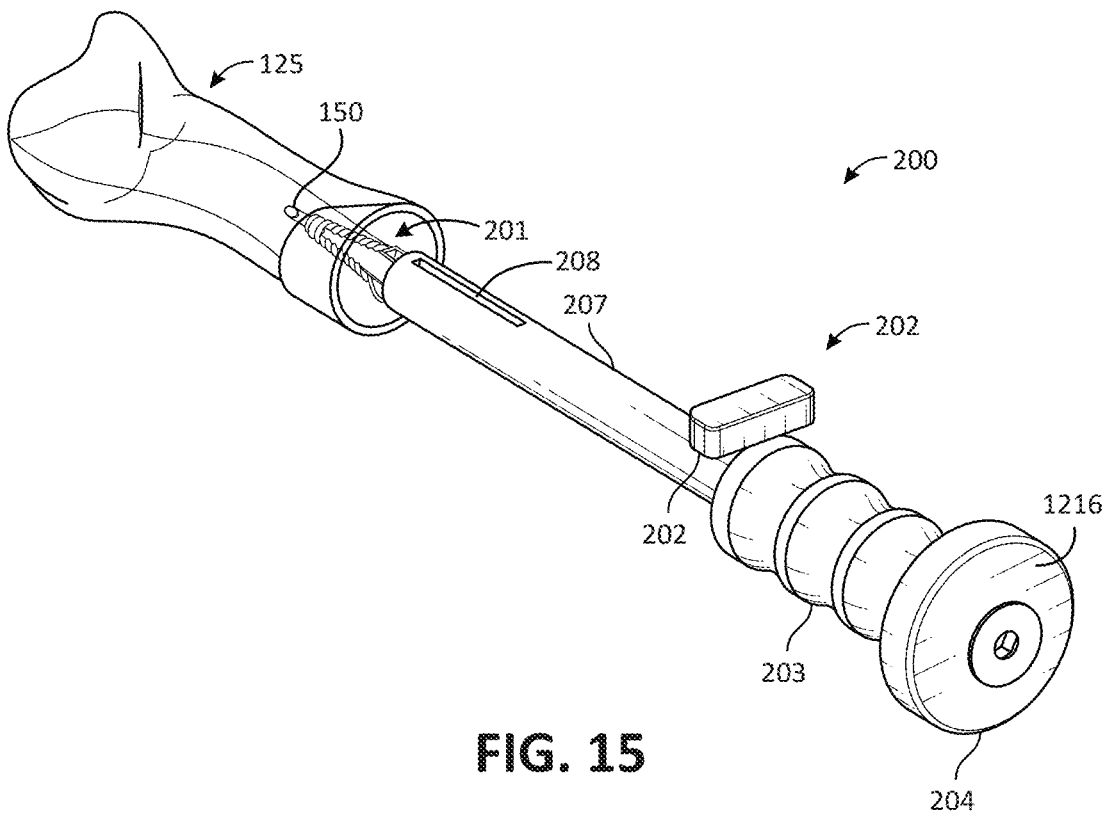
FIG. 15 is a perspective view of a broach tool preparing a metatarsal head, according to an embodiment of the present disclosure.
Figure 16:
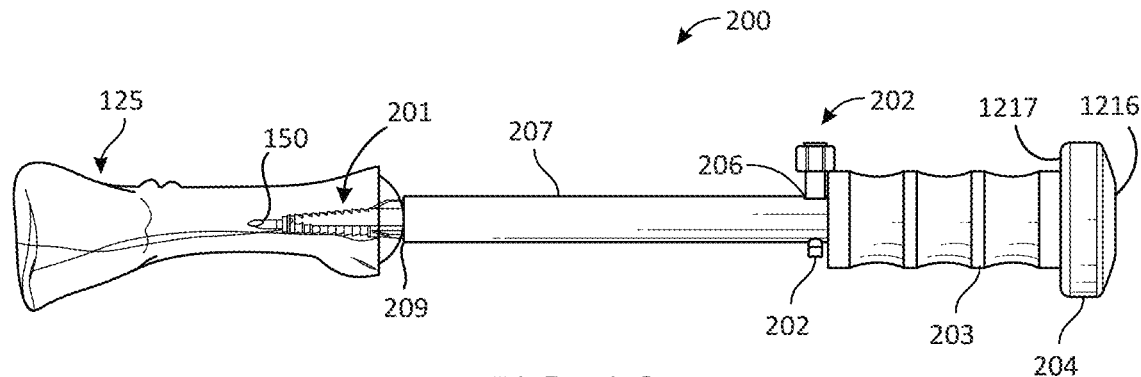
FIG. 16 is a side view of FIG. 15.

The method may also include a broach tool or form broach 200 that may be utilized. FIG. 15 is a perspective view of the form broach 200 engaged with a metatarsal 125 over the guide pin 150. The form broach 200 may include a cutting form 201 with a cross-sectional profile generally corresponding to the cross-sectional profile of any stem of an implant. FIG. 16 is a side view of the form broach 200 engaged with the metatarsal 125 over the guide pin 150.

FIGS. 42-45C show additional views of the form broach 200 and its various components in more detail.

In some embodiments, the form broach 200 may be placed over the guide pin 150 and advanced towards the bone 125. The form broach 200 may include at least one marking or an alignment line 208 that may be aligned with a cutting form 201 of the broach tool. The form broach 200 may further be designed such that the cutting form 201 is at the distal end of a slap hammer 203 style device. Further, the slap hammer 203 device may include a keyed retention pin or pin 202 for securing the slap hammer 203 in a secure position when the pin 202 is in place and allowing the slap hammer 203 to slide along the shaft 207 of the device when the pin 202 is removed. Further, the pin 202 may be designed such that when it has a specific orientation with respect to the shaft 207 of the device, the pin 202 cannot be removed, but when the pin 202 is rotated 90 degrees from its initial orientation, it can be removed. The form broach 200 may be inserted over the guide pin 150 with the alignment line 208 oriented at a 12 o'clock position. The form broach 200, with the pin 202 in a position so that the slap hammer 203 is in a secure position, may then be impacted on a strike plate 204 with a mallet (not shown). The form broach 200 may have a step 209 along its shaft 207 to limit the maximum depth the cutting form 201 can travel into the bone 125. The form broach 200 may be impacted on the strike plate 204 until the maximum depth is achieved. The pin 202 may then be removed to allow the slap hammer 203 to move freely along the shaft 207 of the device. The slap hammer 203 may then be used to remove the cutting from 201 its engagement within the bone 125.

In some embodiments, a system for preparing a metatarsal bone 125 with a broach tool 200 to receive a metatarsal arthroplasty implant may include a broach tool shaft 207 having a longitudinal axis 1210, a proximal end 1211, and a distal end 1212, a cutting form 201 disposed at the distal end 1212 of the broach tool shaft 207 that may be shaped to correspond to a central shaft of a metatarsal arthroplasty implant, a strike plate 204 disposed at the proximal end 1211 of the broach tool shaft 207 having an insertion strike surface 1216 and a removal strike surface 1217 opposite the insertion strike surface 1216, and a slap hammer 203 slidable along the broach tool shaft 207 to facilitate removal of the cutting form 201 from the metatarsal bone 125. The insertion strike surface 1216 of the strike plate 204 may be configured to receive and transmit an insertion impact force (e.g., from a mallet, not shown) to drive the cutting form 201 into the metatarsal bone 125 and prepare the metatarsal bone 125 to receive the metatarsal arthroplasty implant. The removal strike surface 1217 of the strike plate 204 may be configured to receive and transmit a removal impact force from the slap hammer 203 to remove the cutting form 201 from the metatarsal bone 125.

In some embodiments of the system, the broach tool 200 may also include a retention feature 1213 configured to selectively control movement of the slap hammer 203 along the broach tool shaft 207.

In some embodiments of the system, the retention feature 1213 may include a keyed retention pin 202 and a hole or keyed hole 206 formed through the broach tool shaft 207 and configured to receive the keyed retention pin 202 therein to selectively control movement of the slap hammer 203 along the broach tool shaft 207.

In some embodiments of the system, when the keyed retention pin 202 is placed in a first orientation with respect to the keyed hole 206, the keyed retention pin 202 may be allowed to pass through the keyed hole 206 to remove the keyed retention pin 202 from the broach tool shaft 207 and allow the slap hammer 203 to slide along the broach tool shaft 207. Moreover, when the keyed retention pin 202 is placed in a second orientation with respect to the keyed hole 206, the keyed retention pin 202 may be retained within the keyed hole 202 to prevent the slap hammer 203 from sliding along the broach tool shaft 207.

In some embodiments of the system, the cutting form 201 may include a plurality of cutting form teeth 1218 and/or a plurality of longitudinal grooves 1219. The plurality of cutting form teeth 1218 and/or the plurality of longitudinal grooves 1219 may be arranged and shaped to correspond to a shape of a central shaft of a metatarsal arthroplasty implant.

In some embodiments of the system, the at least one marking 208 may be configured to indicate an orientation of the cutting form 201 with respect to the broach tool shaft 207.

In some embodiments, a system for preparing a metatarsal bone 125 with a broach tool 200 to receive a metatarsal arthroplasty implant may include a broach tool shaft 207, a strike plate 204 having an insertion strike surface 1216 and a removal strike surface 1217 opposite the insertion strike surface 1216, a slap hammer 203 slidable along the broach tool shaft 207 to facilitate removal of the cutting form 201 from the metatarsal bone 125, and a retention feature 1213 configured to selectively control movement of the slap hammer 203 along the broach tool shaft 207. The insertion strike surface 1216 of the strike plate 204 may be configured to receive and transmit an insertion impact force (e.g., from a mallet, not shown) to drive the cutting form 201 into the metatarsal bone 125 and prepare the metatarsal bone 125 to receive the metatarsal arthroplasty implant. The removal strike surface 1217 of the strike plate 204 may be configured to receive and transmit a removal impact force from the slap hammer 203 to remove the cutting form 201 from the metatarsal bone 125.

In some embodiments of the system, the broach tool shaft 207 may also include a central longitudinal passageway 1221 configured to receive the guide pin 150 therethrough.

In some embodiments, a method for preparing a metatarsal bone 125 with a broach tool 200 to receive a metatarsal arthroplasty implant may include placing a cutting form 201 of the broach tool 200 against the metatarsal bone 125, the cutting form 201 comprising a shape corresponding to a central shaft of the metatarsal arthroplasty implant, as well as imparting at least one insertion impact force to an insertion strike surface 1216 of a strike plate 204 of the broach tool 200 to drive the cutting form 201 into the metatarsal bone 125.

In some embodiments, the method may also include inserting a keyed retention pin 202 into a broach tool shaft 207 of the broach tool 200 to prevent a slap hammer 203 of the broach tool 200 from sliding along the broach tool shaft 207 as the cutting form 201 is driven into the metatarsal bone 125.

In some embodiments, the method may also include removing the keyed retention pin 202 from the broach tool shaft 207 to allow the slap hammer 203 to slide along the broach tool shaft 207 after the cutting form 201 has been driven into the metatarsal bone 125.

In some embodiments, the method may also include imparting at least one removal impact force to a removal strike surface 1217 of the strike plate 204 with the slap hammer 203 to remove the cutting form 201 from the metatarsal bone 125.

In some embodiments, the method may also include placing the keyed retention pin 202 in a first orientation with respect to a keyed hole 206 formed in the broach tool shaft 207 to permit removal of the keyed retention pin 202 from the keyed hole 206 and allow the slap hammer 203 to slide along the broach tool shaft 207.

In some embodiments, the method may also include placing the keyed retention pin 202 in a second orientation with respect to a keyed hole 206 formed in the broach tool shaft 207 to prevent removal of the keyed retention pin 202 from the keyed hole 206 and prevent the slap hammer 203 from sliding along the broach tool shaft 207.

Figure 17A:
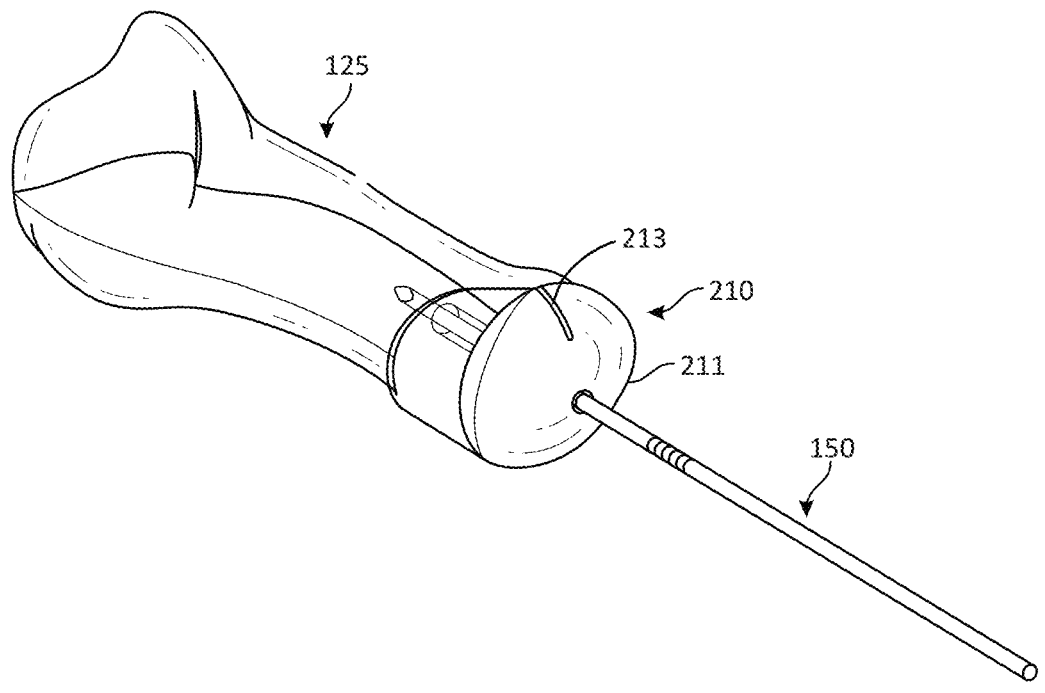
FIG. 17A is a perspective view of a trial device placed on a metatarsal head, according to an embodiment of the present disclosure.
Figure 17B:
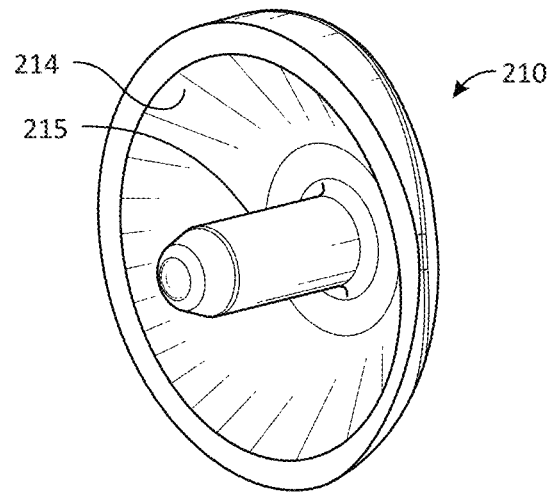
FIG. 17B is a perspective view of the trial device of FIG. 17A.
Figure 18:
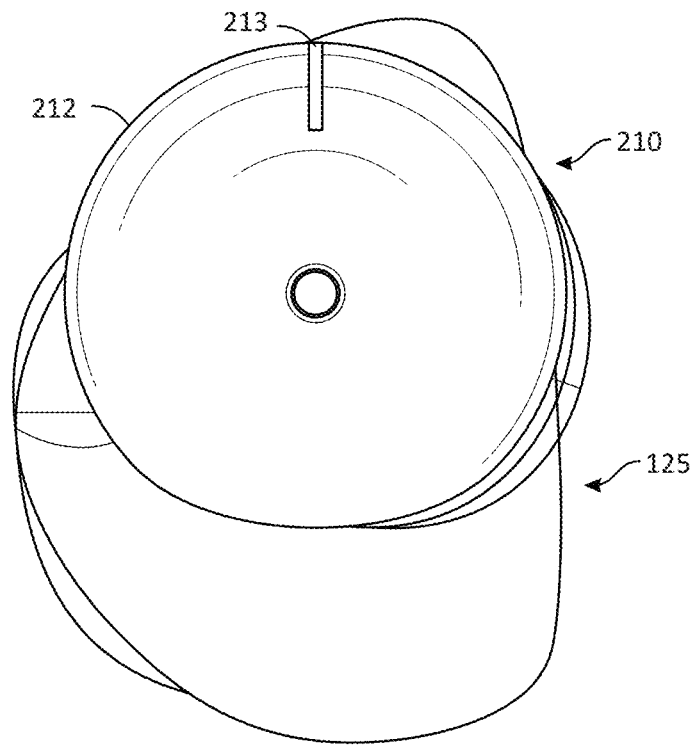
FIG. 18 is a front view of the trial device trial device of FIG. 17A.

As shown if FIGS. 17A-18, in some embodiments the method may also include use of a trial device 210 to confirm sizing, placement, and/or range of motion prior to placing the implant 100. The trial device 210 may be placed over the guide pin 150 and advanced towards the bone 125. The trial device 210 may include a convex outer surface 211 and a concave inner surface 214 that may be generally equal to the corresponding concave inner surface 112 of the implant 100, at least in some embodiments. As the anatomy of patients may vary, the implant 100 may include a plurality of sizes all with the same general profile and features. The trial device 210 may further include a stem 215 that may be shorter than the stem 113 of the implant 100 and/or that may have a smaller diameter than the stem 113 of the implant 100 such that, when the trial device 210 is placed into the bone 125, the trial device 210 may lightly engage the bone 125 such that it can sufficiently maintain its position while remaining easy to remove from the bone 125. The trial device 210 may be made from a plastic material or a metal material and may be manufactured using conventional techniques or using 3d printing technology, etc. The trial device 210 may be inserted over the guide pin 150 until it is secured on the metatarsal head. The guide pin 150 may then be removed from the bone and the joint may be put through a range of motion test. If the joint is too tight (e.g., the joint cannot complete a full range of motion), additional reaming may be warranted. If additional reaming is warranted, the guide pin 150 may be re-inserted and the trial device 210 may be removed. After the trial device 210 has been removed, reaming, drill and/or broaching may be repeated. Once these steps of the method are completed, the trial device 210 may be re-inserted over the guide pin 150, the guide pin 150 may be removed again, and the range of motion may be re-tested. This process may be repeated until a desired range of motion is achieved.

FIG. 18 is a front view of one embodiment of a trial device 210 engaged with a metatarsal 125 over the guide pin 150. The outer periphery 212 of the trial device 210 may generally correspond to the profile of the metatarsal 125. The trial device may further include an indication mark 213 on the convex outer surface 211 so that the orientation of the trial device 210 may represent the orientation of the implant 100.

Figure 19:
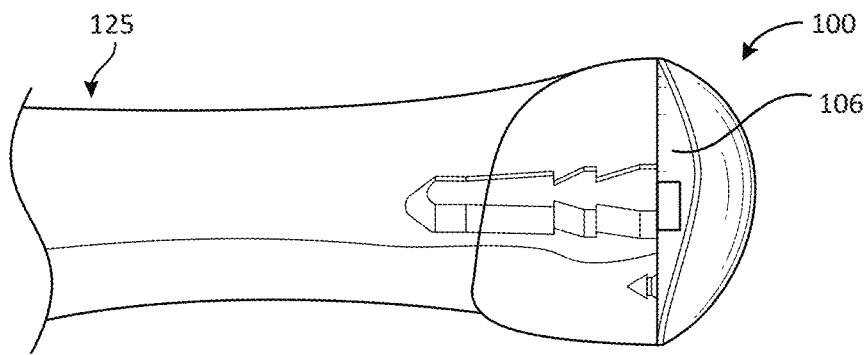
FIG. 19 is a side view of the metatarsal arthroplasty implant of FIG. 1A fully seated within a metatarsal bone.

As shown in FIG. 19, the method may then proceed with final placement of the implant 100 on the bone 125. FIG. 19 is a side view of the implant 100 fully seated in the metatarsal 125.

Figure 20:
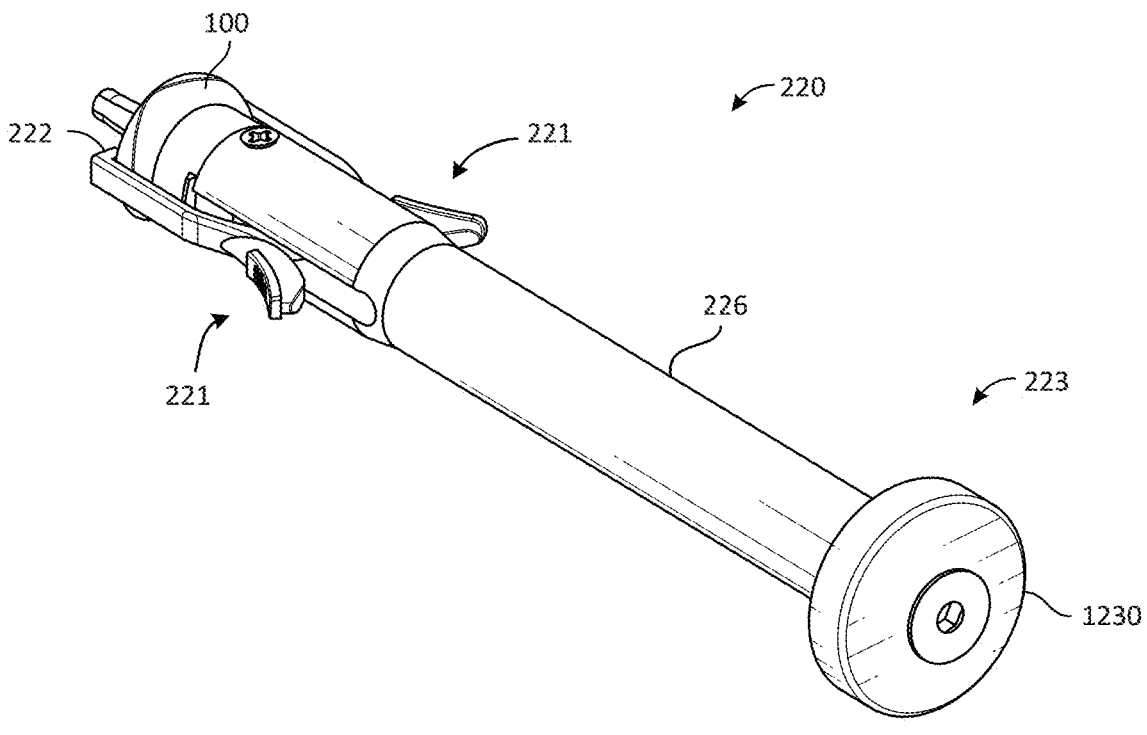
FIG. 20 is a perspective view of an inserter tool coupled to the metatarsal arthroplasty implant of FIG. 1A, according to an embodiment of the present disclosure.
Figure 21:
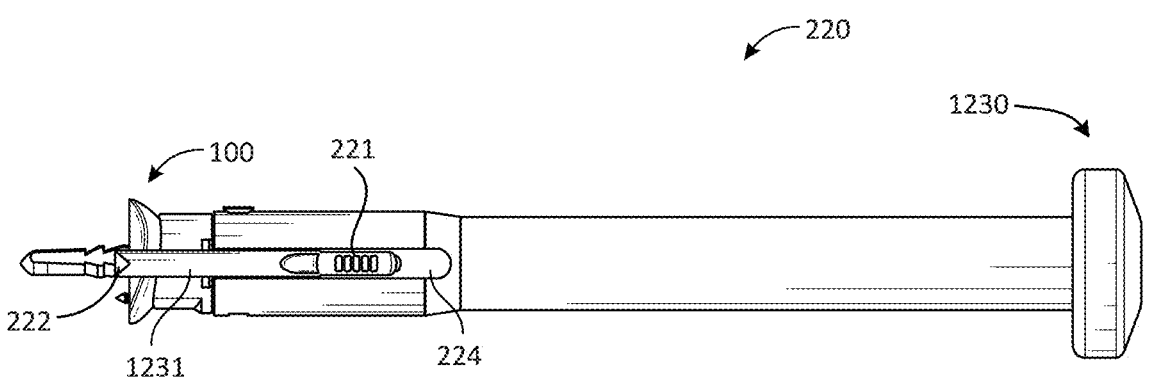
FIG. 21 is a side view of FIG. 20.
Figure 22A:
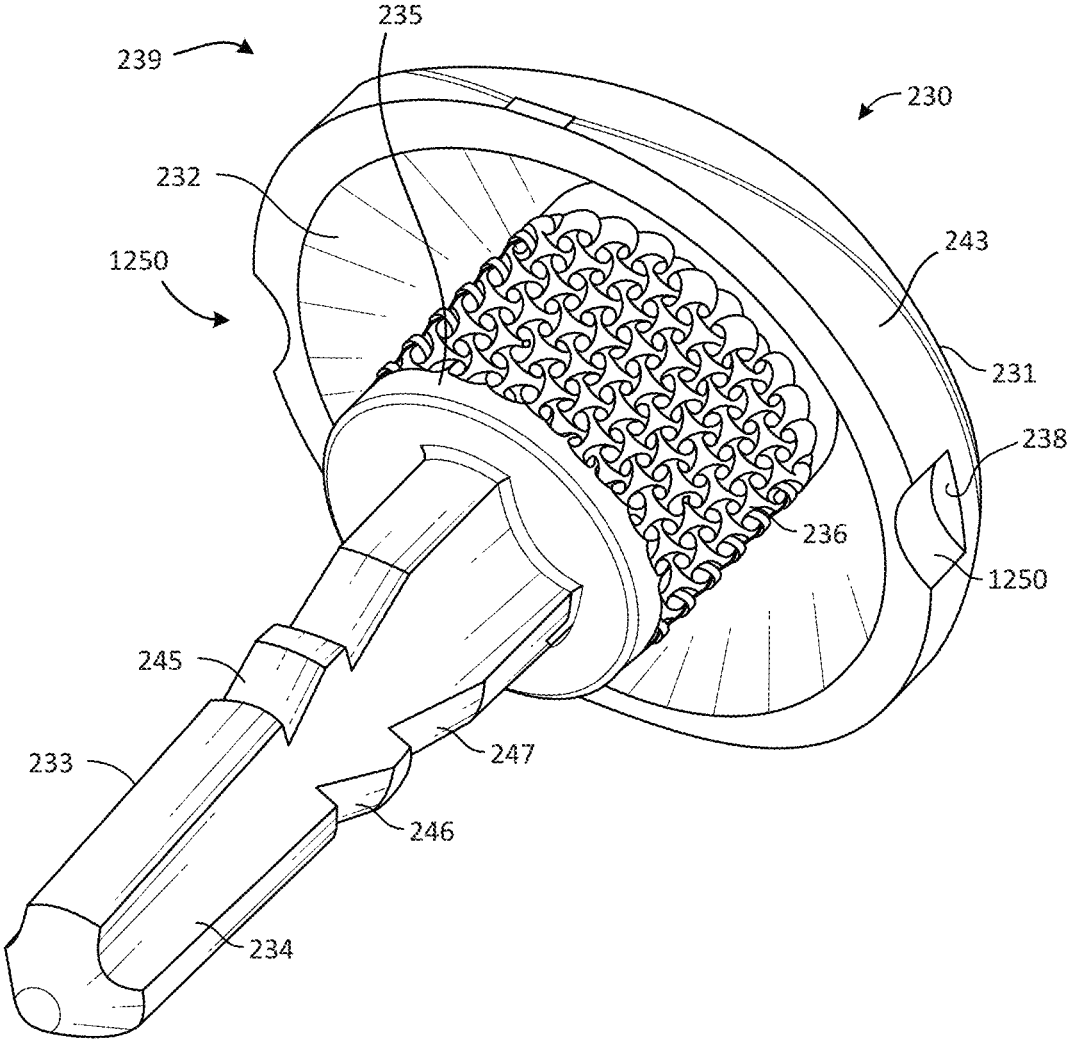
FIG. 22A is a perspective view of a metatarsal arthroplasty implant, according to another embodiment of the present disclosure.
Figure 22B:
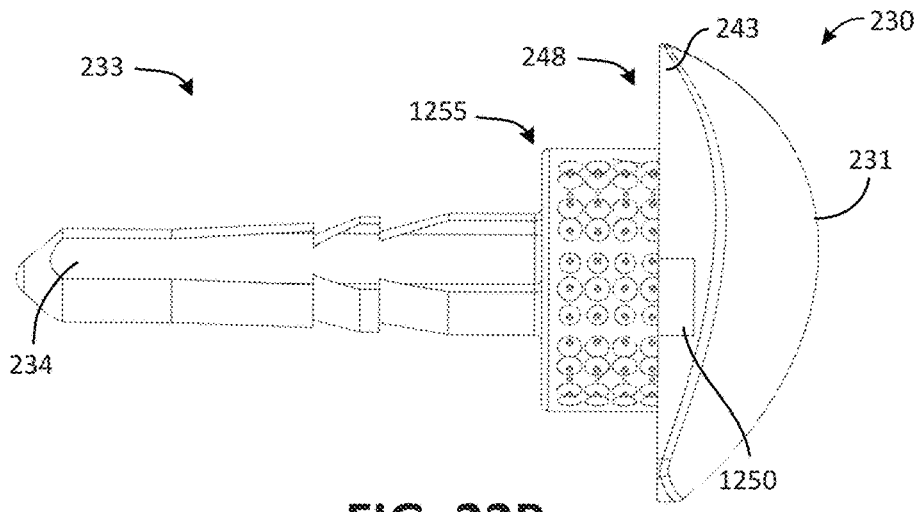
FIG. 22B is a side view of FIG. 22A.
Figure 22C:
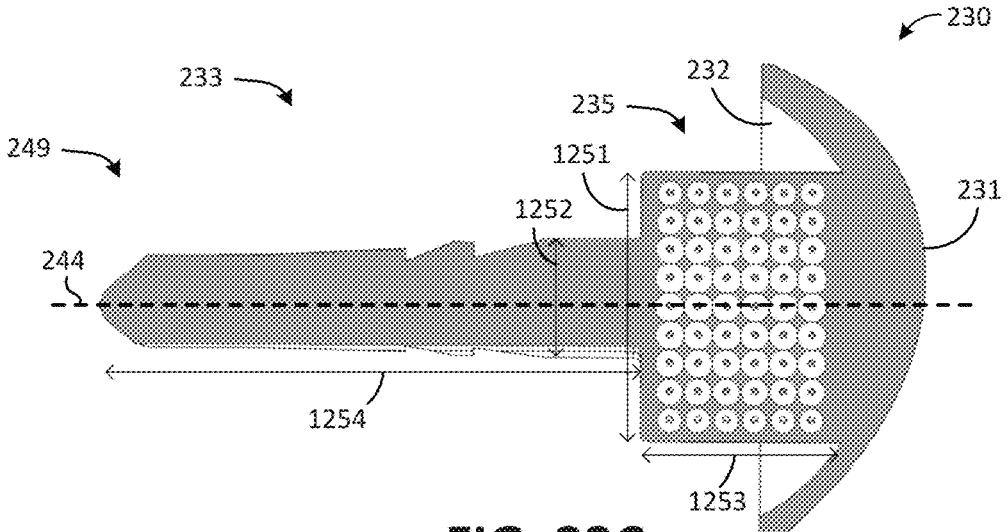
FIG. 22C is a cross-sectional side view of FIG. 22B.

In some embodiments, the implant 100 may be preassembled on an inserter tool or inserter device 220, as shown in FIGS. 20 and 21. FIG. 20 is a perspective view of an inserter device 220 engaged with the implant 100 and FIG. 21 is a side view of the inserter device 220 engaged with the implant 100. FIGS. 38-41B show additional views of the inserter tool 220 and its components in more detail.

The inserter device 220 may be designed such that the implant 100 is securely held in place with one or more gripping fingers 221 that may comprise a first release member and a second first release member, as will be discussed in more detail below. The inserter device 220 may further be designed to allow impaction with a mallet (not shown) on the proximal end 223 of the inserter device 220 to facilitate impaction of the implant 100 into the bone 125. In some embodiments, the gripping fingers 221 may also include fingers or tabs 222 designed to engage with the undercuts 123 formed in the periphery of the implant 100. The inserter device 220 may also include cut outs 224 to allow pivoting of the gripping fingers 221 to release the implant 100.

In some embodiments, the gripping fingers 221 may further be designed such that pressing the gripping fingers 221 may release the grip on the implant 100. The gripping fingers 221 may further be designed such that, when released, the gripping fingers 221 may retract away from the implant 100.

Prior to impaction, the implant 100 may be positioned such that the cross-sectional profile of the stem 113 may align with the profile in the bone 125 created by the cutting form 201. Partial impaction of the implant 100 may be performed by impacting the proximal end 223 of the inserter device 220 with a mallet (not shown) until the implant 100 is secure in the bone (but may not be fully seated at this point). After the implant 100 is partially impacted, the gripping fingers 221 may be actuated to release the implant 100 and retract away from the implant 100. Further impaction may then be performed until the implant 100 is fully seated in the bone. Additional fluoroscopic images in the anterior-posterior and sagittal planes may also be obtained to confirm desired placement.

In some embodiments, a system for performing a metatarsal arthroplasty surgical procedure with an inserter tool 220 configured to place a metatarsal arthroplasty implant on a metatarsal bone 125 may include an inserter tool shaft 226 having a longitudinal axis 227, a proximal end 228, and a distal end 229, a first finger or tab 222 disposed at the distal end 229 of the inserter tool shaft 226 configured to engage a first undercut surface 123 formed on the metatarsal arthroplasty implant, and a second finger or tab 222 disposed at the distal end 229 of the inserter tool shaft 226 opposite the first finger and configured to engage a second undercut surface 123 formed on the metatarsal arthroplasty implant. In this manner, the first finger and the second finger may be configured to removably couple the metatarsal arthroplasty implant to the inserter tool 220 during the metatarsal arthroplasty surgical procedure. The inserter tool 220 may also include a strike plate 1230 disposed at the proximal end 228 of the inserter tool shaft 226 configured to receive and transmit an impact force to the metatarsal arthroplasty implant through the inserter tool shaft 226 to drive a central shaft of the metatarsal arthroplasty implant into the metatarsal bone 125 and place the metatarsal arthroplasty implant on the metatarsal bone 125.

Figure 39:
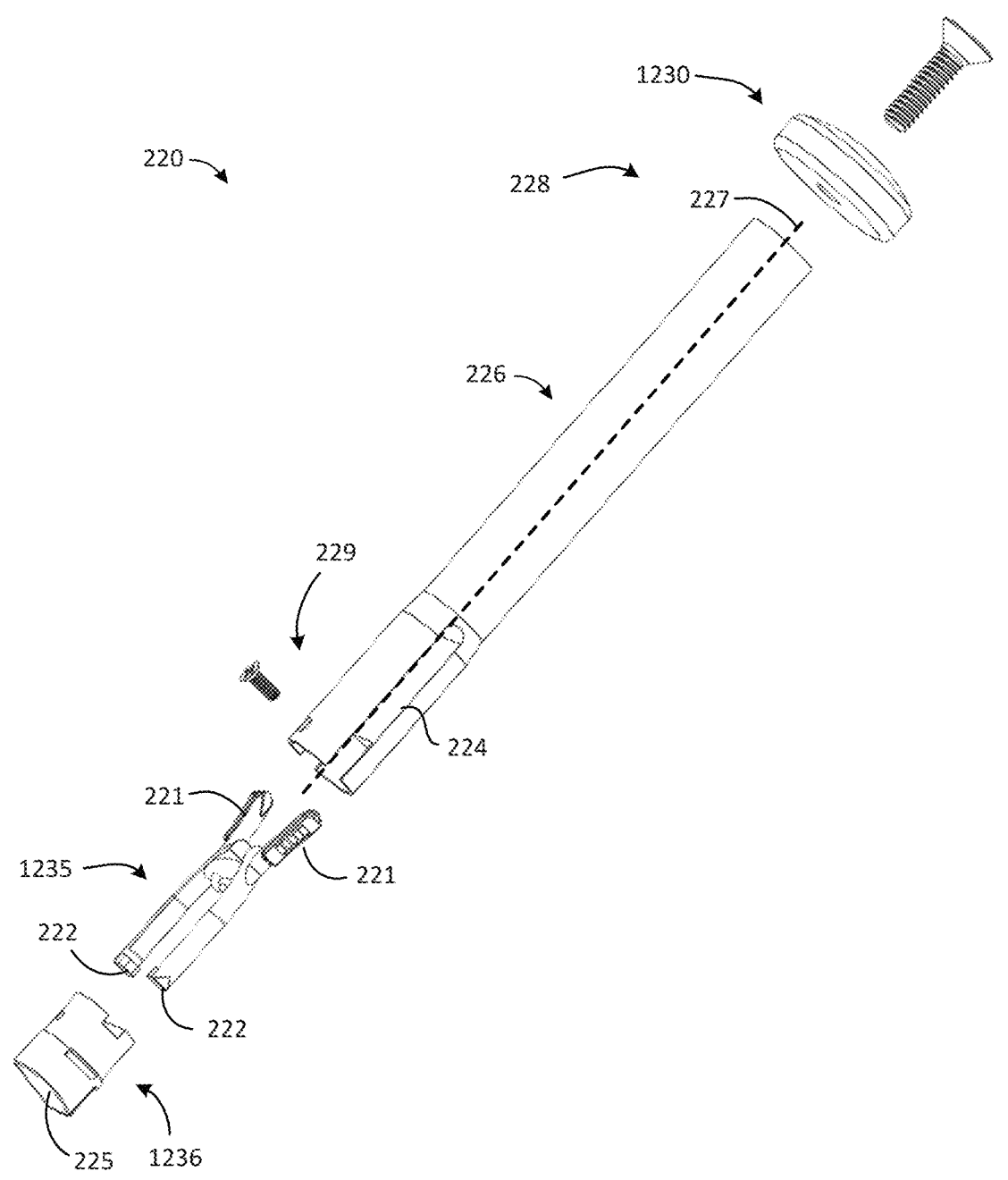
FIG. 39 is an exploded view of the inserter tool shown in FIG. 38.
Figure 40A:
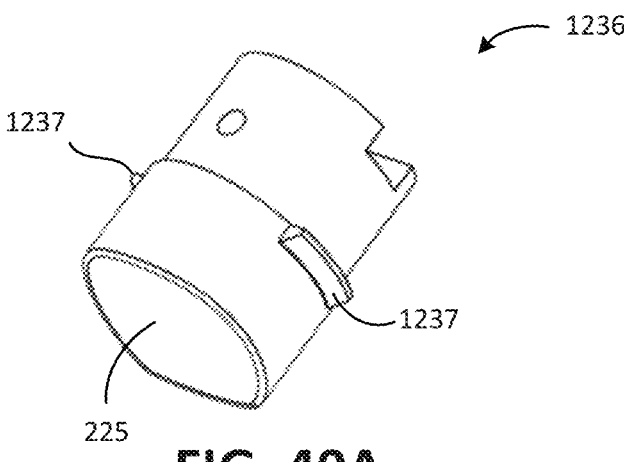
FIG. 40A is a perspective view of a distal member of the inserter tool shown in FIG. 39, according to an embodiment of the present disclosure.
Figure 40B:
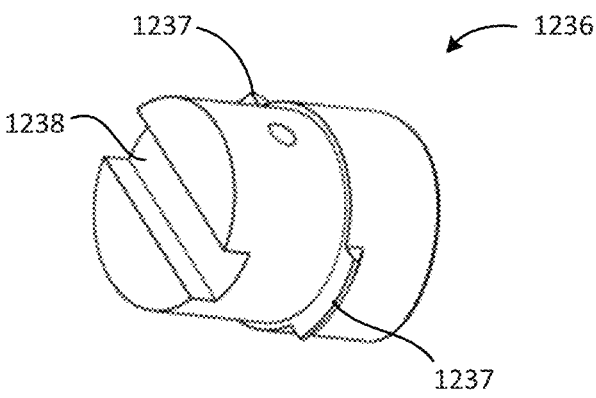
FIG. 40B is another perspective view of the distal member.
Figure 40C:
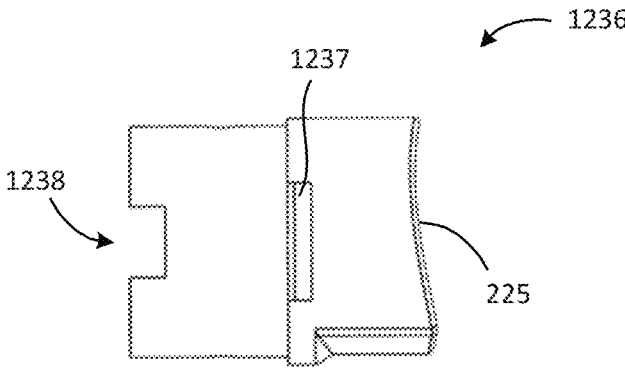
FIG. 40C is a side view of the distal member.
Figure 41A:
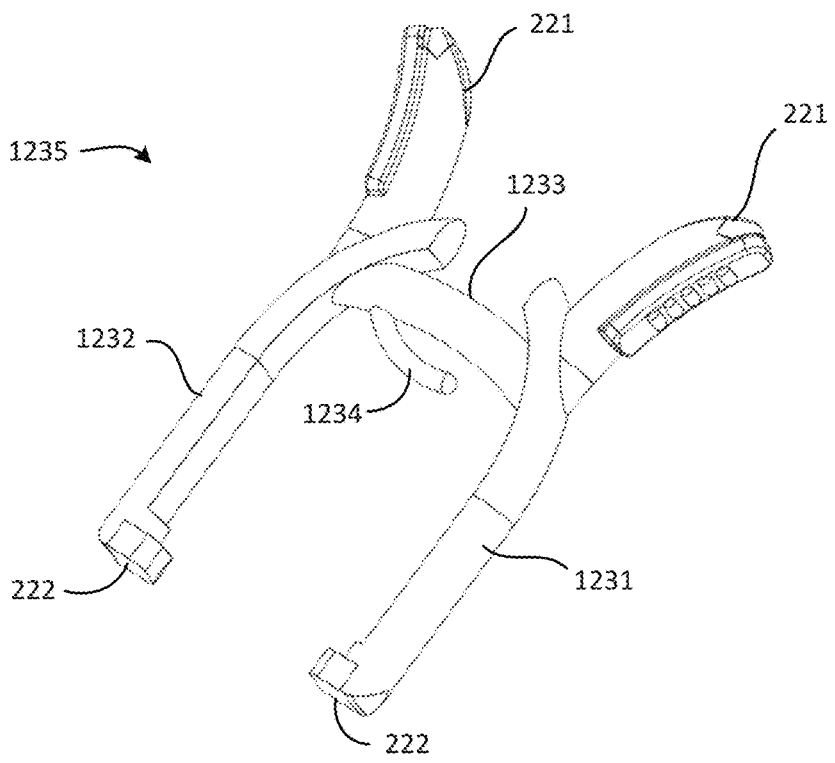
FIG. 41A is a perspective view of a retainer member of the inserter tool shown in FIG. 39, according to an embodiment of the present disclosure.
Figure 41B:
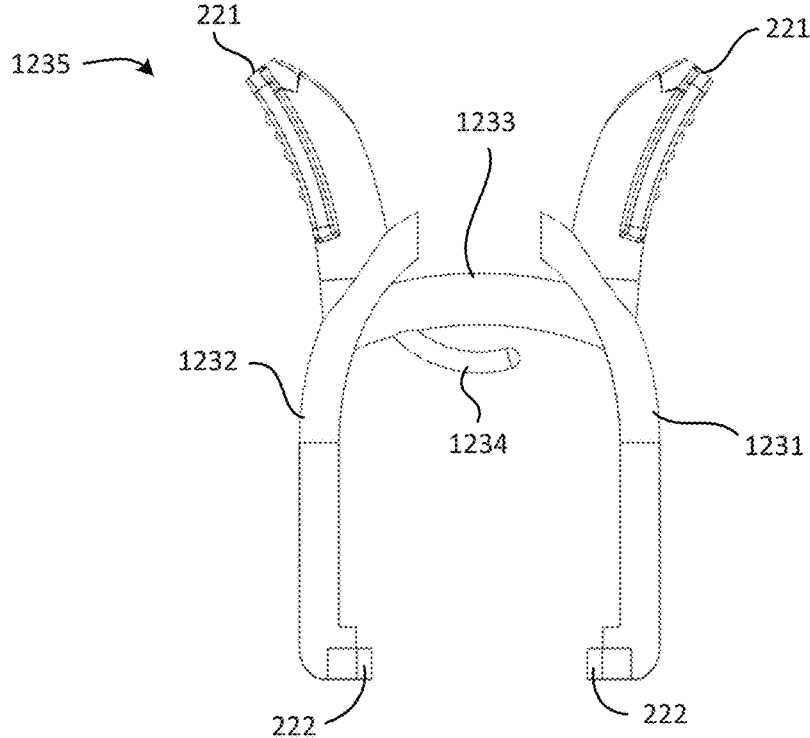
FIG. 41B is a front view of the retainer member.
Figure 42:
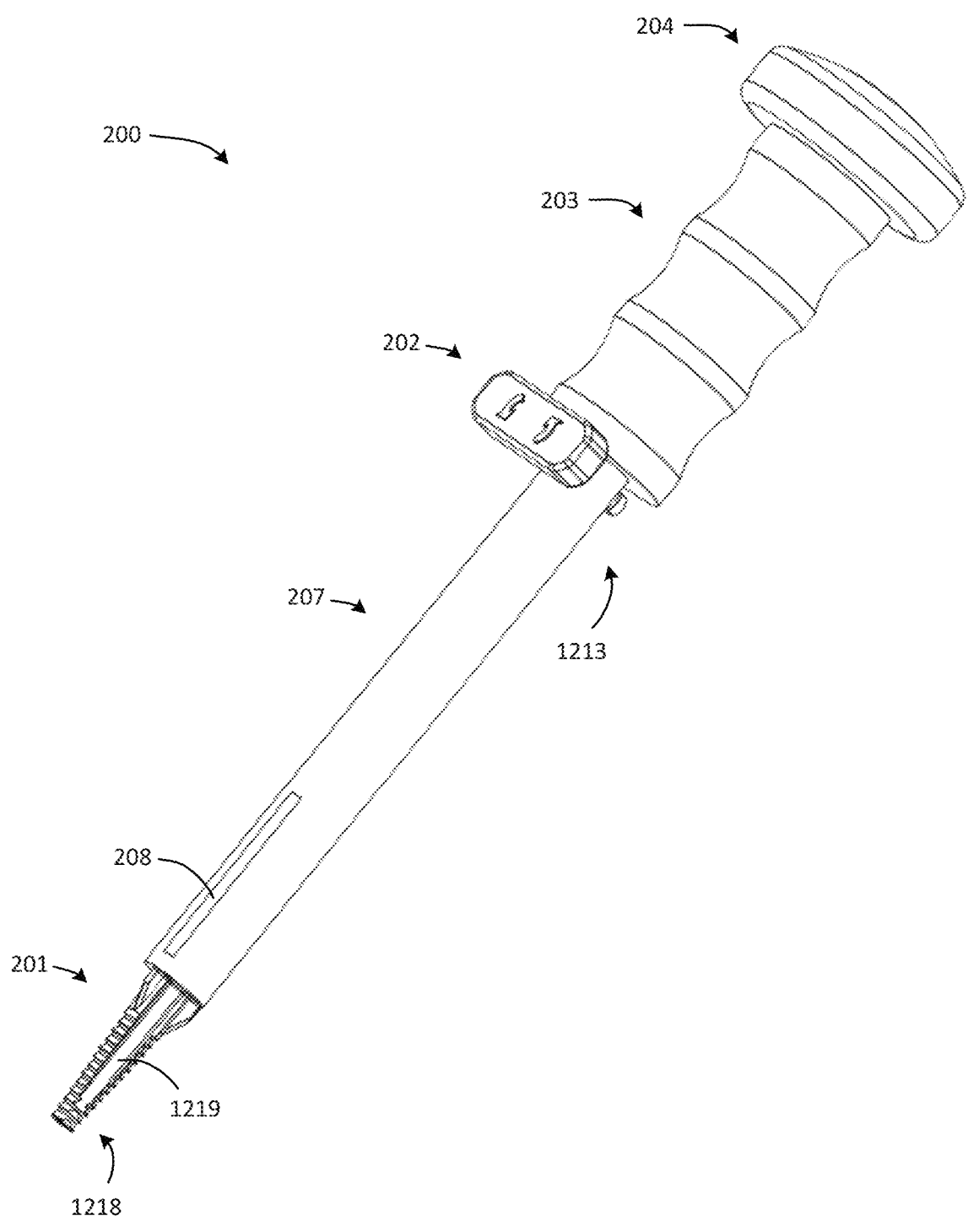
FIG. 42 is a perspective view of the broach tool shown in FIG. 15.
Figure 43:
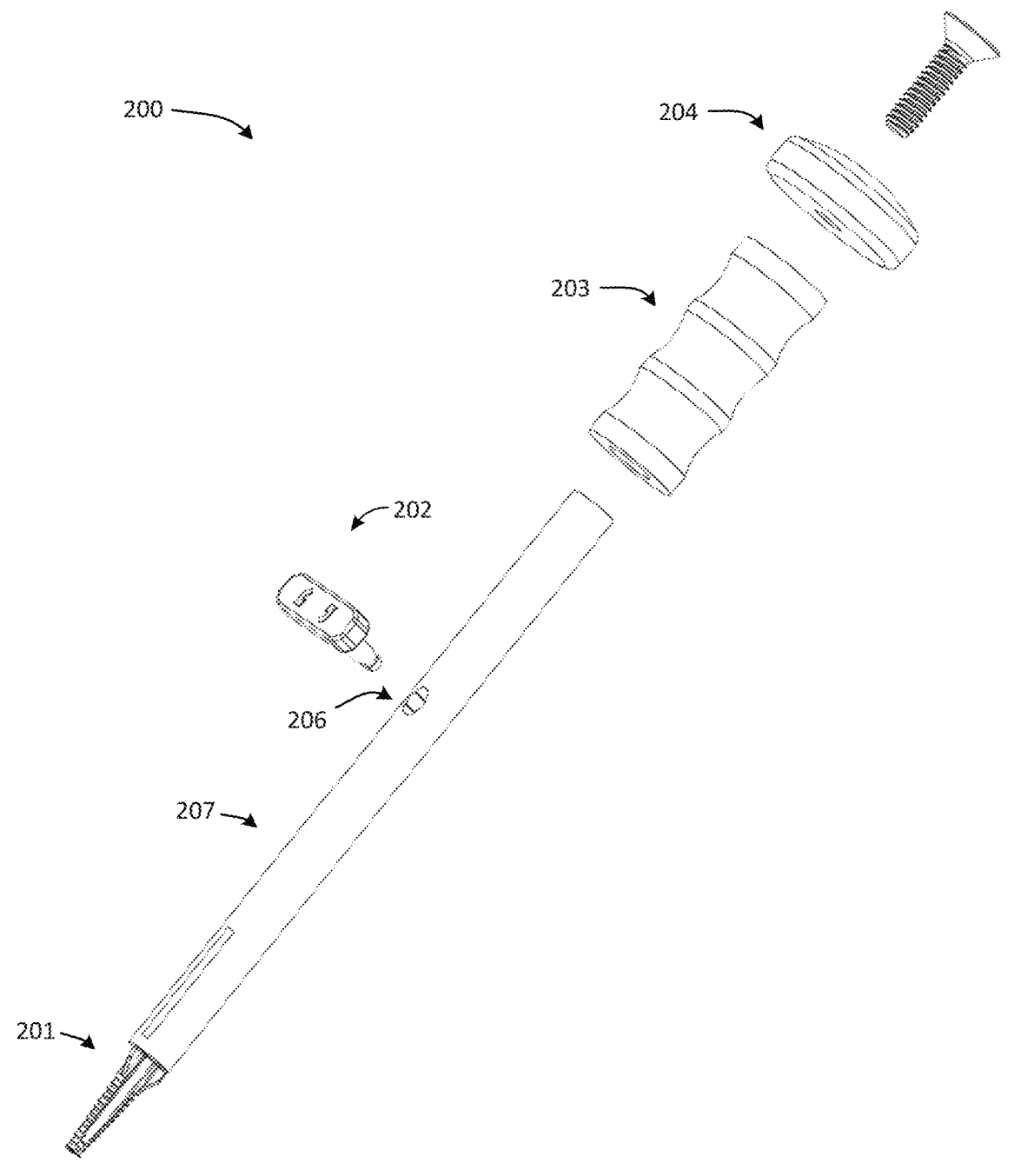
FIG. 43 is an exploded view of the broach tool of FIG. 42.

In some embodiments, the inserter tool 220 may include a retainer member 1235, as shown in FIGS. 39 and 41A-41B. The retainer member 1235 may include a first arm 1231, a second arm 1232, the one or more gripping fingers 221 (that may comprise a first release member and a second first release member), a resilient member 1233, and/or a tension member 1234. The first finger or tab 222 may be disposed at a distal end of the first arm 1231, the second finger or tab 222 may be disposed at a distal end of the second arm 1232. The first finger of the first arm and the second finger of the second arm may be configured to removably couple the metatarsal arthroplasty implant to the inserter tool 220 during the metatarsal arthroplasty surgical procedure.

In some embodiments, the resilient member 1233 may be coupled intermediate the first arm 1231 and the second arm 1232 and may be configured to resiliently bias the first arm 1231 and the second arm 1232 toward each other with a bias force to retain the implant therebetween.

In some embodiments, the tension member 1234 may be coupled to the resilient member 1233. Alternatively, the tension member 1234 may be coupled to the first arm 1231 and/or the second arm 1232.

In some embodiments, the tension member 1234 may fit within the tension member slot 1238 and may be likewise configured with a resilient bias force that tends to push away from the distal member 1236 to maintain a proximally directed tension force on the first finger and the second finger to retain the metatarsal arthroplasty implant on the inserter tool 220 during the metatarsal arthroplasty surgical procedure.

In some embodiments, the one or more gripping fingers 221 may comprise a first release member coupled to a proximal end of the first arm 1231, and a second release member coupled to a proximal end of the second arm 1232, opposite the first release member. Compressing the first release member and the second release member toward each other may overcome the bias force of the resilient member 1233 to disengage the first finger from the first undercut surface and the second finger from the second undercut surface of the implant to remove the implant from the inserter tool 220.

As shown in FIGS. 38-40C, in some embodiments the inserter tool 220 may also include a distal member 1236 having projections 1237, the tension member slot 1238, and/or a concave abutment surface 225 shaped to engage the convex articular surface of the metatarsal arthroplasty implant.

In some embodiments, the projections 1237 may help hold the retainer member 1235 proximally when an implant is not coupled with the inserter 220.

In some embodiments, the concave abutment surface 225 may be configured to receive the impact force through the inserter tool shaft 226 and transmit the impact force to the convex articular surface of the metatarsal arthroplasty implant to drive the central shaft of the metatarsal arthroplasty implant into the metatarsal bone 125 to place the metatarsal arthroplasty implant on the metatarsal bone 125.

Figure 46:
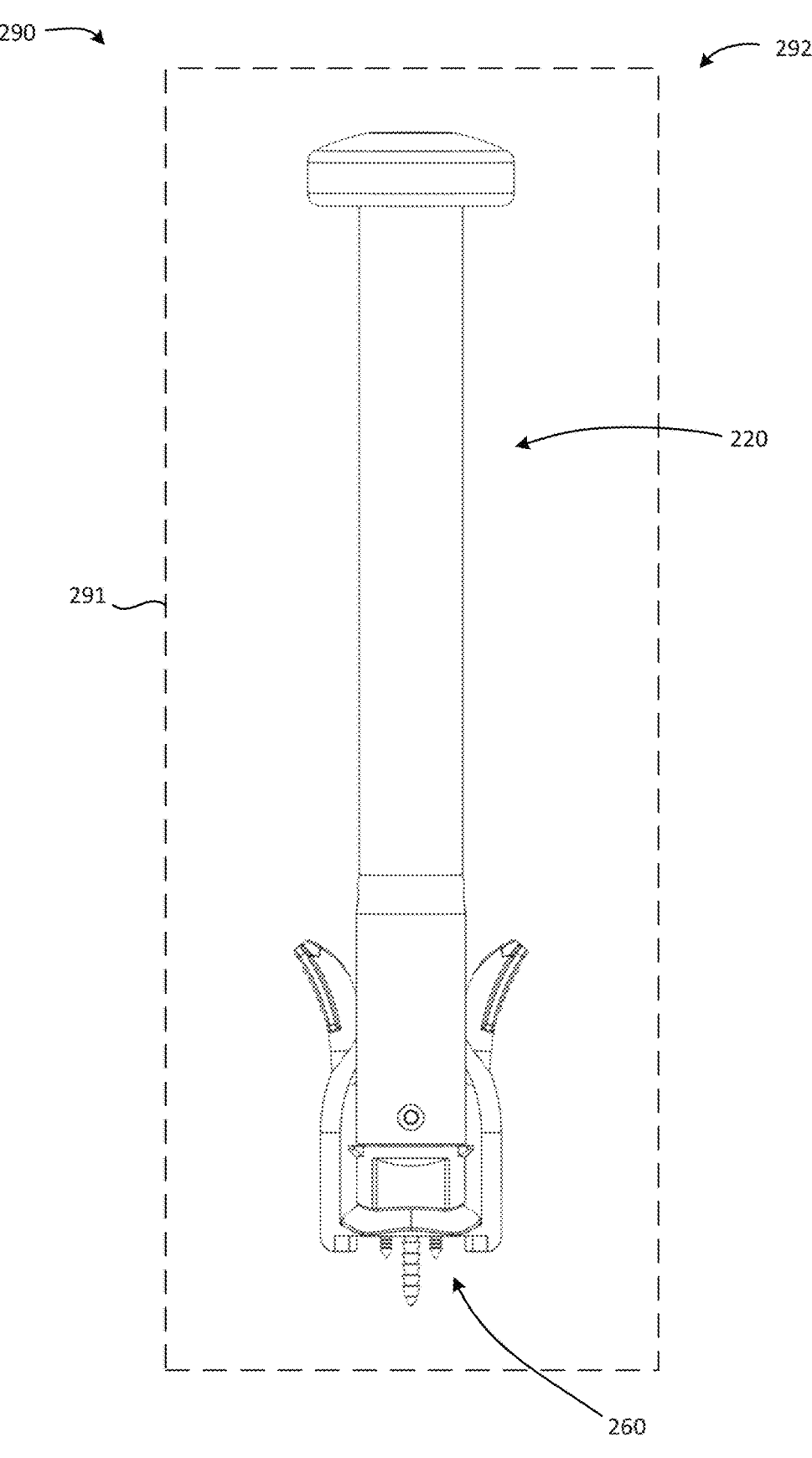
FIG. 46 is a top view of surgical kit comprising a metatarsal arthroplasty implant and inserter tool assembly placed within a sterilized package, according to an embodiment of the present disclosure.

As shown in FIG. 46, in some embodiments a surgical kit 290 for performing a metatarsal arthroplasty surgical procedure may include a sterilized package 291 and/or sterilizable packaging and a metatarsal arthroplasty implant 260 pre-loaded onto an inserter tool 220 (forming a metatarsal arthroplasty implant and inserter tool assembly 292 placed inside the sterilized package 291) that may be configured to install the metatarsal arthroplasty implant 260 on a metatarsal bone 125. However, it will be understood that the sterilized package 291 may be configured to hold any/all of the implants and instruments that are described or contemplated herein, in any size or range of sizes.

After the implant has been installed on the bone 125, in some embodiments the method may further include closure of the incision with absorbable sutures followed by subcuticular and skin closures and/or a compressive dressing that may be applied to the surgical site.

FIGS. 22A-29 illustrate various views of a revision metatarsal arthroplasty implant, revision implant, or implant 230, according to an alternative embodiment of the present disclosure, as well as instruments and methods for installing the implant 230. The implant 230 may be designed for use in revision surgery to replace a failed implant (for example, the implant 100 and/or another metatarsal resurfacing implant) and to replace the natural joint engaging surface and engage the proximal phalanx after removal of the failed implant. As the anatomy of patients may vary, the implant 230 may include a plurality of sizes all with the same general profile and features. Variations in size may also be used to adapt the implant 230 to the size and/or shape of the failed implant, for example, by ensuring that the implant 230 properly fills the space left by the previous implant while removing minimal additional bone.

The implant 230 may be intended to provide a replacement articulating surface of the metatarsal head. The implant 230 may be designed to articulate with the proximal phalanx (not shown). The implant 230 and instruments that may be necessary to complete the surgical procedure may be provided to a clinician in a single use sterilized package or may be provided in a package that requires sterilization prior to use, as previously discussed. The packages may include trays specifically designed to accommodate the implant 230 and instruments. The method for implantation may include any step described or contemplated herein, such as the following: (1) Create incision and expose metatarsal head; (2) Remove previous failed implant; (3) Insert defect sizing instrument to determine implant size; (4) Sizing of the metatarsal head to determine optimal implant size; (5) Placement of the guide pin 150; (6) Fluoroscopic confirmation of guide pin position; (7) Repositioning of the guide pin, as desired; (8) Reaming the metatarsal head such that the profile generally corresponds to the concave inner surface of the implant; (9) Drill with a step drill bit into the medullary canal; (10) Form broach the medullary canal to generally match the implant stem profile; (11) Place trial device and test range of motion of the joint; (12) If the joint is too tight, repeat previous steps, as desired; (13) Implant insertion; (14) Fluoroscopic confirmation of implant location; and/or (15) Close incision.

In some embodiments, the implant 230 may include a convex articular surface or convex outer surface 231 and a concave bone-facing surface or concave inner surface 232. The concave inner surface 232 may include an enlarged proximal portion or bone engagement block 235 extending therefrom. In some embodiments, the bone engagement block 235 may have a substantially cylindrical shape.

In some embodiments, an outer surface of the bone engagement block 235 may include at least one surface feature to promote bone in-growth. In some embodiments, the at least one surface feature may include at least one of pores 236, a surface roughness feature, a nano texture feature, hydroxyapatite, and/or any other surface treatment that may promote bone in-growth.

In some embodiments, the bone engagement block 235 may further include a central shaft or stem 233 extending therefrom. In some embodiments, the stem 233 may comprise a conical member having a constant thickness, or decreases in thickness along the length thereof, or the stem 233 may include one or more flutes 234 or longitudinal grooves extending along the length of the stem 233. The one or more flutes 234 may limit the rotational movement of the implant 230 after implantation in the metatarsal 125. Further, the stem 233 may include radial grooves 245 or at least one barb central shaft barb that may be designed to prevent the implant 230 from backing out of the metatarsal 125 after implantation. In some embodiments, each of the radial grooves 245 may have a first leading angle 246 and a second trailing angle 247.

In some embodiments, a metatarsal arthroplasty implant 230 may include an articular member 239 and a central shaft 233 sized for insertion into a metatarsal bone 125. The articular member 239 may include a convex articular surface 231, a concave bone-facing surface 232 opposite the convex articular surface 231, and at least one side surface 243 intermediate the convex articular surface 231 and the concave bone-facing surface 232. The central shaft 233 may include a central shaft longitudinal axis 244, a central shaft proximal end 248 coupled to the concave bone-facing surface 232 of the articular member 239, a central shaft distal end 249 extending away from the concave bone-facing surface 232 of the articular member 239, and at least one surface feature formed along at least a portion of the central shaft 233 and configured to promote bone in-growth therein.

In some embodiments, the at least one surface feature configured to promote bone in-growth comprises at least one of: a surface roughness feature, a nano texture feature, and at least one pore 236.

In some embodiments, the at least one surface feature may include a plurality pores 236 formed along a proximal portion 235 of the central shaft 233 configured to promote bone in-growth therein.

In some embodiments, the proximal portion 235 of the central shaft 233 comprises a first width 1251 or diameter and a distal portion 249 of the central shaft 233 comprises a second width 1252 or diameter, wherein the first width 1251 of the proximal portion 235 may be greater than the second width 1252 of the distal portion 249.

In some embodiments, the proximal portion 235 of the central shaft 233 may comprise substantially circular cross-sectional shapes taken transverse the central shaft longitudinal axis 244.

In some embodiments, the distal portion 249 of the central shaft 233 may include at least one central shaft barb 245 shaped to resist removal of the central shaft 233 from the metatarsal bone 125.

In some embodiments, the articular member 239 may also include a plurality of notches 1250 formed in the at least one side surface 243 with undercut surfaces 238 extending below the convex articular surface 231 configured to facilitate installation and removal of the metatarsal arthroplasty implant 230 from the metatarsal bone 125.

In some embodiments, the metatarsal arthroplasty implant 230 may include an enlarged proximal portion 235 having a substantially cylindrical shape and a distal portion 249 having at least one central shaft barb 245 shaped to resist removal of the central shaft 233 from the metatarsal bone 125.

In some embodiments, the enlarged proximal portion 235 of the central shaft 233 may have a first diameter 1251 and the distal portion 249 of the central shaft 233 may have a second diameter 1252, wherein the first diameter 1251 may be greater than the second diameter 1252.

In some embodiments, the enlarged proximal portion 235 of the central shaft 233 may have a first length 1253 and the distal portion 249 of the central shaft 233 may have a second length 1254, wherein the second length 1254 may be greater than the first length 1253.

In some embodiments, the central shaft may also include a transition portion 1255 intermediate the enlarged proximal portion 235 and the distal portion 249 of the central shaft 233.

In some embodiments, the transition portion 1255 may comprise a circular surface.

In some embodiments, the transition portion 1255 may comprise a ramped surface (not shown). In some embodiments, ramped surface may comprise a conical surface tapering down toward the smaller distal portion 249 of the central shaft 233.

In some embodiments, at least one of the transition portion and the enlarged proximal portion may include at least one surface feature configured to promote bone in-growth therein, as previously described.

In some embodiments, a method of performing a revision surgical procedure on a metatarsal bone 125 may include: removing a first metatarsal arthroplasty implant from the metatarsal bone 125 (the first metatarsal arthroplasty implant comprising a first central shaft having a first proximal portion with a first diameter), and inserting a second metatarsal arthroplasty implant into the metatarsal bone 125 (the second metatarsal arthroplasty implant comprising a second central shaft having a second proximal portion with a second diameter) wherein the second diameter of the second proximal portion may be larger than the first diameter of the first proximal portion.

In some embodiments of the method, removing the first metatarsal arthroplasty implant from the metatarsal bone 125 may include grasping at least one notch formed in the first metatarsal arthroplasty implant and transmitting at least one extraction force proximally through at least one under-cut surface associated with the at least one notch to remove the first metatarsal arthroplasty implant from the metatarsal bone.

In some embodiments, the method may also include forming a recess within the metatarsal bone configured to receive the larger second proximal portion of the second metatarsal arthroplasty implant therein.

In some embodiments of the method, forming the recess within the metatarsal bone may include at least one of: drilling the recess into the metatarsal bone, reaming the recess into the metatarsal bone, and broaching the recess into the metatarsal bone.

In some embodiments of the method, inserting the second metatarsal arthroplasty implant into the metatarsal bone may also include engaging a concave abutment surface of an inserter tool against a convex articular surface of an articular member of the second metatarsal arthroplasty implant, and transmitting at least one insertion force distally through the concave abutment surface of the inserter tool to the convex articular surface of the second metatarsal arthroplasty implant to insert the second metatarsal arthroplasty implant into the metatarsal bone.

Figure 23:
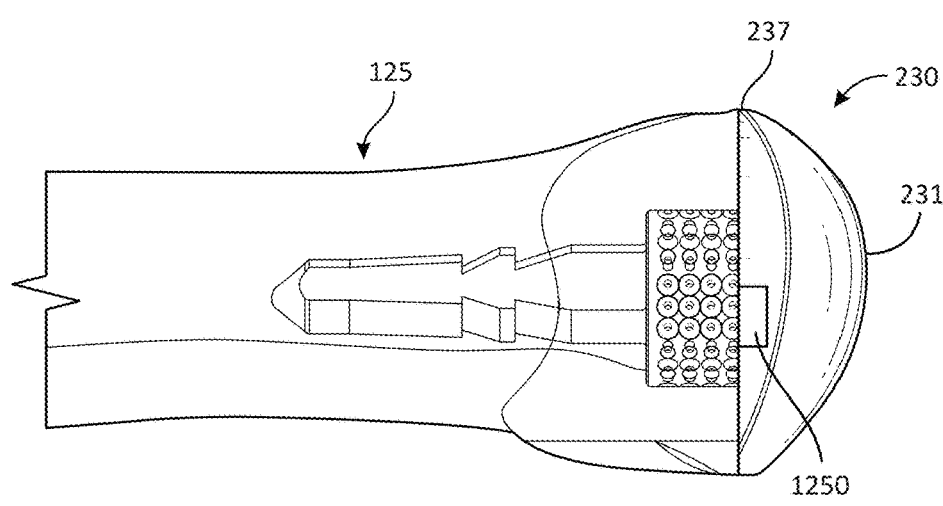
FIG. 23 is a side view of the metatarsal arthroplasty implant of FIG. 22A fully seated in a metatarsal bone.

FIG. 23 is a side view of the implant 230 fully seated in a metatarsal 125. The outer profile 237 of the implant 230 may be generally aligned with the outer profile of the prepared metatarsal head.

Figure 24:
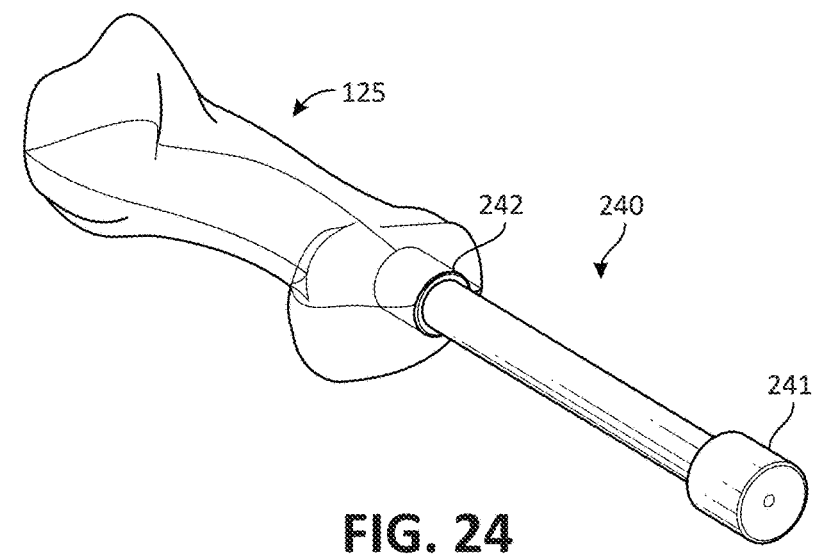
FIG. 24 is a perspective view of a defect sizing instrument placed within a metatarsal bone, according to an embodiment of the present disclosure.
Figure 25:
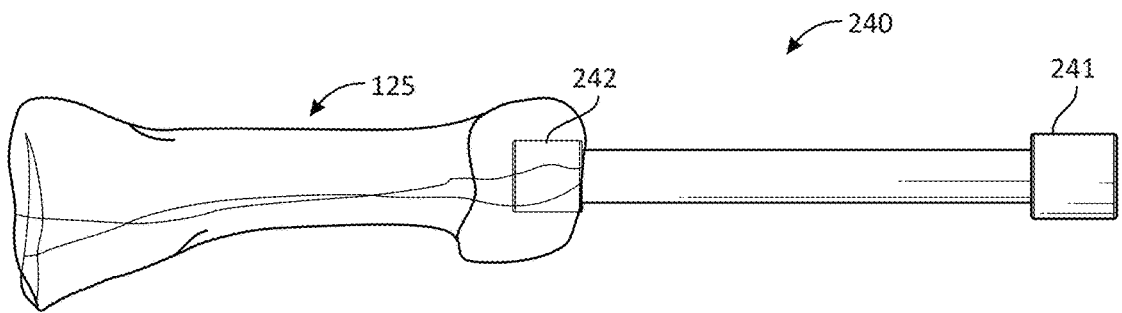
FIG. 25 is a side view of FIG. 24.

FIG. 24 is a perspective view of a defect sizing instrument 240 engaged with a metatarsal 125. FIG. 25 is a side view of a defect sizing instrument 240 engaged with a metatarsal 125. The defect sizing instrument 240 may include a first sizing head 242 on one end and a second sizing head 241 on a second end.

In a revision procedure, the method may include removal of the failed previous implant. After removal, the defect sizing instrument 240 may be used to determine the size of the previous implant. The defect sizing instrument 240 may be designed such that the diameter of a first sizing head 241 and a second sizing head 242 generally correspond to typical sizes of metatarsal head implants. The defect sizing instrument 240 may be inserted into the cavity in the metatarsal head resulting from the removal of the previous implant. The defect size may correspond to the largest diameter of the sizing head that may be insertable into the cavity. It will be understood that various defect sizing instruments with various diameter sizing heads can be utilized to find the best fit.

Figure 26:
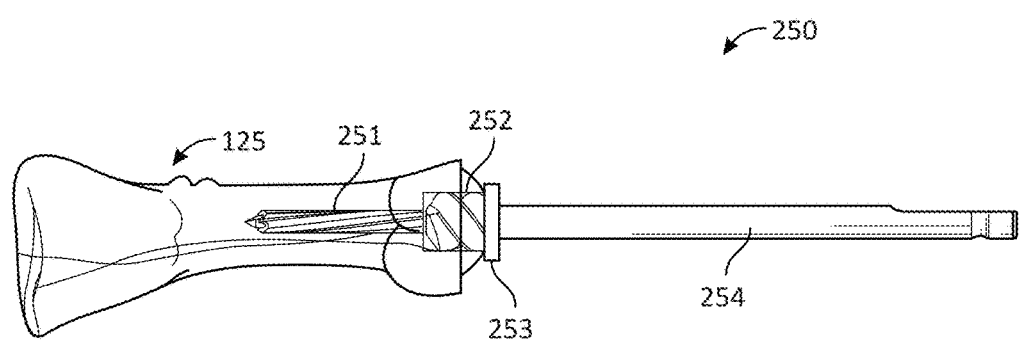
FIG. 26 is a side view of a step drill bit placed within a metatarsal bone, according to an embodiment of the present disclosure.

The revision method may additionally include use of a step drill bit 250 that may have a first fluted cutting diameter 251 and a second fluted cutting diameter 252. FIG. 26 is a side view of the step drill bit 250 engaged with a metatarsal 125. The step drill bit 250 may include a first fluted cutting diameter 251 and a second fluted cutting diameter 252 that has a greater cross-sectional diameter than the first fluted cutting diameter 251. The step drill bit 250 may further include a step or other feature along the shaft 254 to provide a depth stop 253. The depth stop may ensure that the step drill bit 250 does not drill too deep into the metatarsal 125.

The step drill bit 250 may be placed over the guide pin 150 and advanced towards the bone 125. In some embodiments, the first fluted cutting diameter 251 may be between about 2.0 mm and 4.0 mm (e.g., 2.7 mm, in some embodiments). In some embodiments, the length of the first fluted cutting diameter 251 may be between about 18 mm and 25 mm (e.g., 21.5 mm, in some embodiments). In some embodiments, the depth of the first fluted cutting diameter 251 may result in a hole that is about 0.5 mm and 4.0 mm deeper than the stem 233 of the implant 230 that is intended to sit within the bone 125.

The second fluted cutting diameter 252 may be between about 8 mm and 9 mm, or more specifically 8.5 mm. In this embodiment, the second fluted cutting diameter 252 may correspond to an 8 mm diameter previously failed implant. Further, the length of the second fluted cutting diameter 252 may be between about 8 mm and 9 mm, or more specifically 8.5 mm. In some embodiments, the step drill bit 250 may be designed with a step or other feature along the shaft 254 to provide the depth stop 253. The depth stop 253 may ensure that the step drill bit 250 does not drill too deep into the metatarsal 125. The depth stop 253 may be located such that the total drill depth within the bone is between about 28 mm and 32 mm, or more specifically 30 mm.

In another embodiment, the second fluted cutting diameter 252 may have a diameter between about 10 mm and 11 mm, or more specifically 10.5 mm. In this embodiment the second fluted cutting diameter 252 may correspond to a 10 mm diameter previously failed implant. Further, the length of the second fluted cutting diameter 252 may be between 10 mm and 11 mm, or more specifically 10.5 mm. The depth stop 253 may be located such that the total drill depth is between 30 mm and 34 mm, or more specifically 32 mm.

Figure 27:
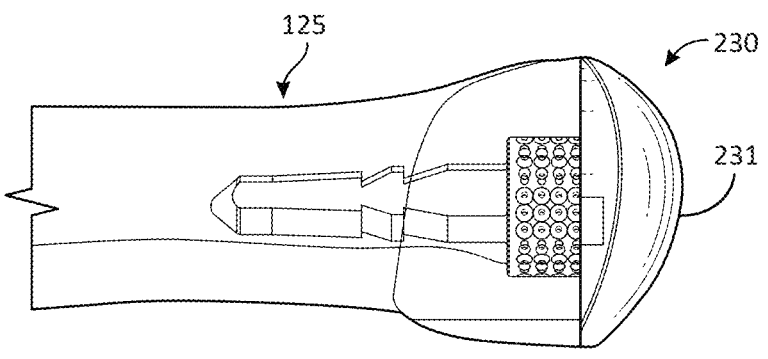
FIG. 27 is a side view of the metatarsal arthroplasty implant of FIG. 22A placed within a metatarsal bone.
Figure 28:
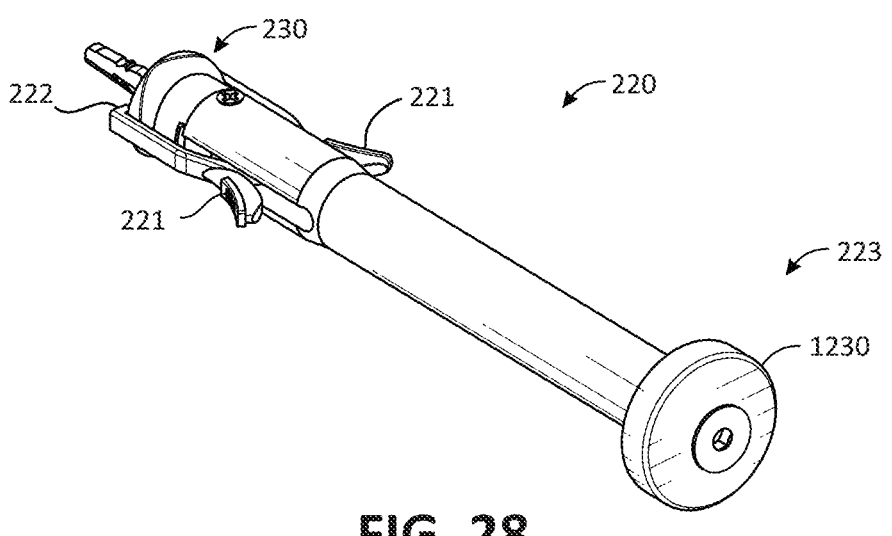
FIG. 28 is a perspective view of an inserter tool coupled to the metatarsal arthroplasty implant of FIG. 22A.
Figure 29:
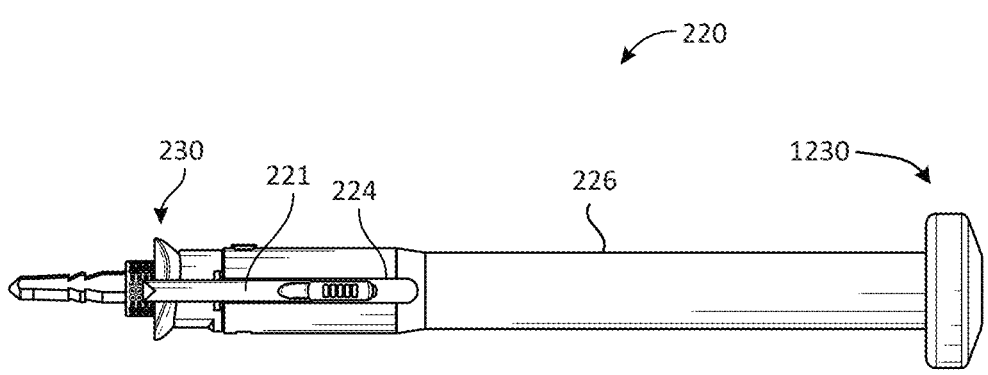
FIG. 29 is a side view of FIG. 28.
Figure 30A:
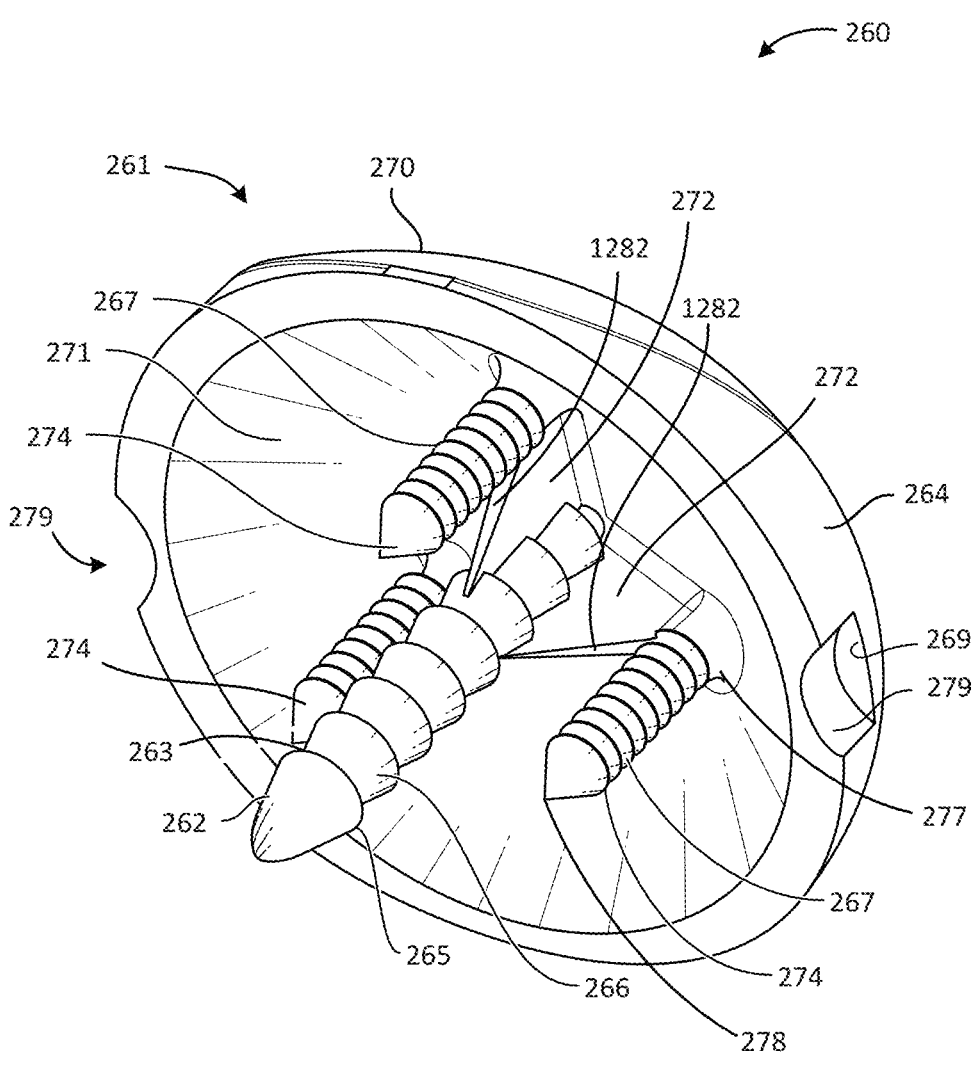
FIG. 30A is a perspective view of a metatarsal arthroplasty implant, according to another embodiment of the present disclosure.
Figure 30B:
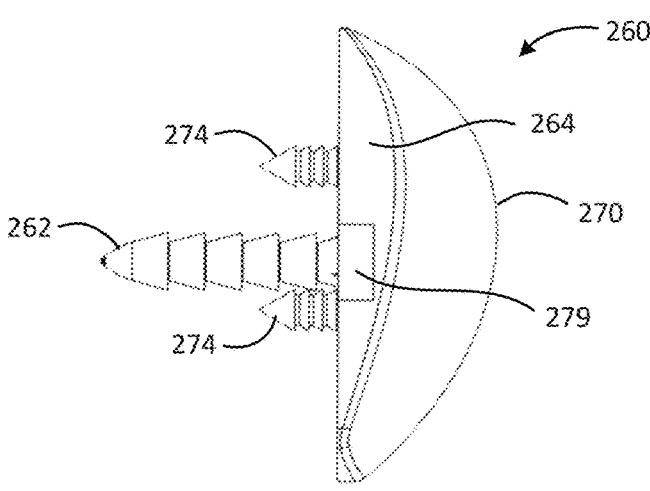
FIG. 30B is a side view of FIG. 30A.
Figure 30C:
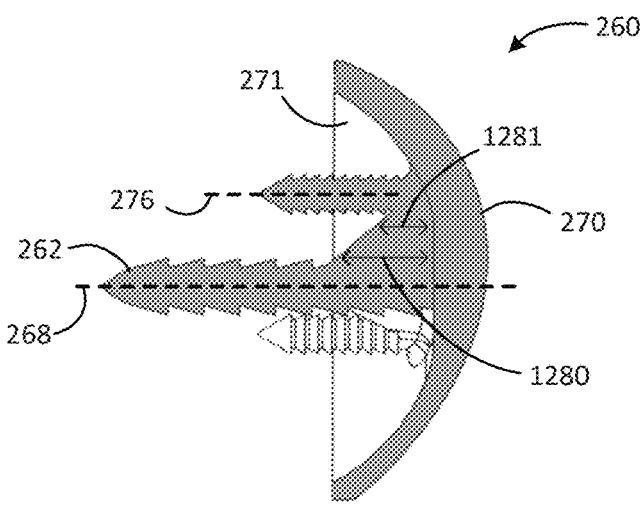
FIG. 30C is a cross-sectional side view of FIG. 30A.

The revision method may then include final placement of the implant 230, as shown in FIG. 27. In some embodiments, the implant 230 may be preassembled on the inserter device 220 to facilitate the insertion procedure, as shown in FIGS. 28 and 29, and previously described. FIG. 29 is a side view of an inserter device 220 engaged with an implant 230. The inserter device 220 may include cut outs 224 to allow pivoting of the gripping fingers 221.

FIGS. 30A-37 illustrate various views of a metatarsal arthroplasty implant or implant 260, according to an alternative embodiment of the present disclosure, as well as instruments and methods for installing the implant 260. The implant 260 may be designed to replace the natural joint engaging surface and engage the proximal phalanx. As the anatomy of patients may vary, the implant 260 may include a plurality of sizes, all with the same general profile and features. The implant 260 may be intended to provide a replacement articulating surface of the metatarsal head such that bone removal at the metatarsal head related to implant placement may be minimized. The implant 260 may be designed to articulate with the proximal phalanx (not shown).

The implant 260 and instruments for completing the surgical procedure may be provided to a clinician in a single use sterilized package or may be provided in a package that requires sterilization prior to use. The packages may include trays specifically designed to accommodate the implant 260 and instruments.

The method for implantation may include or omit any step described herein, such as: (1) Incision and exposure of the metatarsal; (2) Sizing of the metatarsal to determine optimal implant size; (3) Placement of a guide pin; (4) Fluoroscopic confirmation of guide pin position; (5) Repositioning of the guide pin, as desired; (6) Reaming the metatarsal head so that the profile generally corresponds to the concave inner surface of the implant; (7) Drill into the medullary canal; (8) Form broach the medullary canal to generally match the implant stem profile, as desired; (9) Place trial implant and test range of motion of the joint; (10) If the joint is too tight, steps 6 through 9 above may be repeated, as desired; (11) Implant insertion; (12) Fluoroscopic confirmation of implant location; and (13) Close the incision.

The implant 260 may have a convex articular surface or convex outer surface 270 and a concave bone-facing surface or concave inner surface 271. The concave inner surface 271 may have a central shaft or stem 262 extending therefrom.

In some embodiments, the stem 262 may have a constant thickness, may decrease in thickness along the length thereof, or may vary in thickness along the length thereof.

In some embodiments, the stem 262 may include at least one central shaft barb or radial grooves 263 that may be designed to prevent the implant 260 from backing out of the metatarsal 125 after implantation. Each of the radial grooves 263 may have a first leading angle 265 and a second trailing angle 266.

In some embodiments, the concave inner surface 271 may include at least one anti-rotation pin or one or more spikes 274 protruding therefrom.

In some embodiments, three spikes 274 may be present, but it will be understood that any number of spikes 274 may be present. For example, this disclosure encompasses the use of 1, 2, 3, 4, 5, 6, 7, 8, 9, 10 or more spikes 274.

In some embodiments, the spikes 274 may be distributed along the concave inner surface 271. Such distribution may or may not be along a radially symmetrical pattern. Each of the spikes 274 may be proximate the outer edge of the concave inner surface 271, closer to the stem 262, or positioned anywhere along the concave inner surface 271.

In some embodiments, each spike 274 may optionally have a generally circular cross-section such that a centerline or anti-rotation pin longitudinal axis 276 of the spike 274 may be parallel to a centerline or central shaft longitudinal axis 268 of the stem 262.

In some embodiments, the stem 262 may include a plurality of radial grooves 263. Each of the radial grooves 263 may have a first leading angle 265 and a second trailing angle 266.

In some embodiments, each spike 274 may include at least one anti-rotation pin barb or a plurality of radial grooves 267, each having a first leading angle a second trailing angle. These may optionally be similar to those of the stem 262. However, any leading and/or trailing angles may be used for the spikes 274.

In some embodiments, the implant 260 may include at least one rib member or one or more rib sections 272 connecting the stem 262 to the concave inner surface 271. The one or more rib sections 272 may provide additional support for the stem 262 to help avoid bending of the stem 262 relative to the concave inner surface 271. The one or more rib sections 272 may also engage with the bone 125 as the implant 260 is installed to help prevent rotation on the implant 260 after implantation. The combination of the stem 262 with the one or more spikes 274 may allow the thickness of the stem 262 to be reduced while the spikes 274 resist rotational movement of the implant 260 during use. This may also allow the surgeon to remove less bone from the metatarsal head during the procedure. The ability to reduce bone removal may allow the surgeon to maintain the symmetry of the MTP joint with less bone loss to maintain a larger distal end of the metatarsal bone in the event of implant failure.

In some embodiments, a metatarsal arthroplasty implant 260 may include an articular member 261, a central shaft 262 sized for insertion into a metatarsal bone 125, at least one anti-rotation pin 274 spaced apart from the central shaft 262 and sized for insertion into the metatarsal bone 125 adjacent the central shaft 262, and at least one rib member 272 that radially projects from and couples a proximal portion of the central shaft 262 to a proximal portion 277 of the at least one anti-rotation pin 274. The articular member 261 may include a convex articular surface 270, a concave bone-facing surface 271 opposite the convex articular surface 270, and at least one side surface 264 intermediate the convex articular surface 270 and the concave bone-facing surface 271. The central shaft 262 may include a central shaft longitudinal axis 268, a central shaft proximal end coupled to the concave bone-facing surface 271 of the articular member 261, and a central shaft distal end extending away from the concave bone-facing surface 271 of the articular member 261. The at least one anti-rotation pin 274 may include an anti-rotation pin longitudinal axis 276, an anti-rotation pin proximal end 277 coupled to the concave bone-facing surface 271 of the articular member 261, and an anti-rotation pin distal end 278 extending away from the concave bone-facing surface 271 of the articular member 261.

In some embodiments, a first height 1280 of the at least one rib member 272 proximate the central shaft 262 may be greater than a second height 1281 of the at least one rib member 272 proximate the at least one anti-rotation pin 274.

In some embodiments, the at least one rib member 272 may include a substantially straight leading edge 1282 that extends between the first height 1280 and the second height 1281 of the at least one rib member 272.

In some embodiments, the at least one rib member 272 may include a curved leading edge (not shown) that extends between the first height 1280 and the second height 1281 of the at least one rib member 272. For example, the curved leading edge may be configured to curve in the proximal direction, the distal direction, or both.

In some embodiments, the leading edge may also comprise one or more cutting features (e.g., a sharp edge, serrations, etc., not shown) to facilitate insertion of the at least one rib member 272 into the bone 125.

In some embodiments, the at least one anti-rotation pin 274 may include three anti-rotation pins that are radially spaced apart from each other about the central shaft 262, and the at least one rib member 272 may include three rib members that each radially project from the central shaft 262 to couple with one of the three anti-rotation pins.

In some embodiments, the three anti-rotation pins and/or three rib members may be equally spaced apart from each other about the central shaft at 120 degree angles.

In some embodiments, the at least one anti-rotation pin 274 may also include at least one barb shaped to resist removal of the at least one anti-rotation pin from the metatarsal bone.

In some embodiments, the central shaft 262 may comprise a first plurality of circular cross-sectional shapes taken transverse the central shaft longitudinal axis 268, and the at least one anti-rotation pin 274 may comprise a second plurality of circular cross-sectional shapes taken transverse the anti-rotation pin longitudinal axis 276.

In some embodiments, the implant 260 may include at least one side surface 106 with a notch or a plurality of notches 279 formed therein comprising undercut surfaces or undercuts 269, as previously described.

Figure 31:
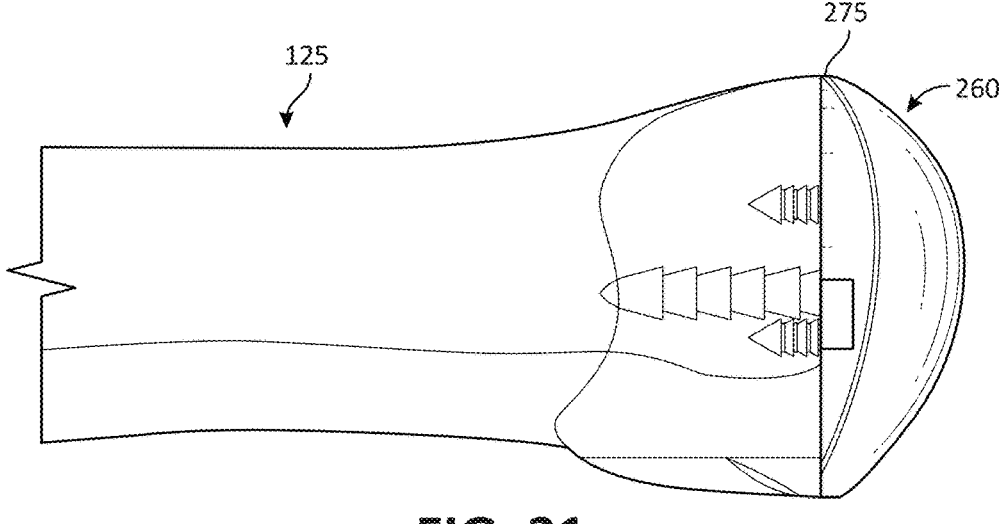
FIG. 31 is a side view of the metatarsal arthroplasty implant of FIG. 30A fully seated in a metatarsal bone.
Figure 32:
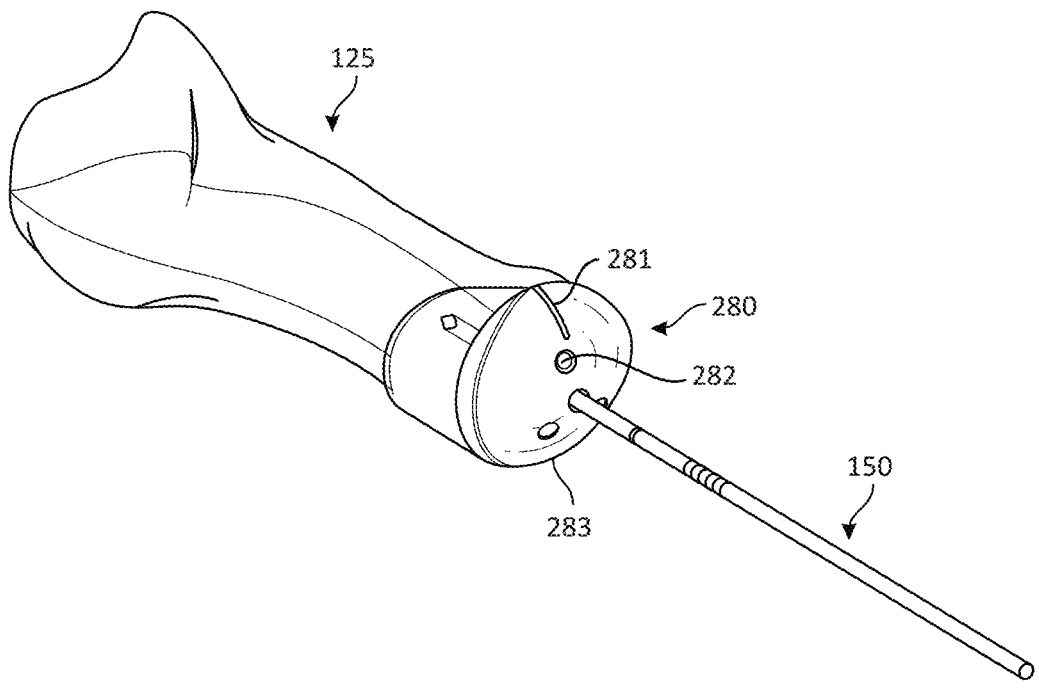
FIG. 32 is a perspective view of a trial device placed on a metatarsal head with a guide pin, according to another embodiment of the present disclosure.

FIG. 31 is a side view of the implant 260 fully seated in a metatarsal 125. In some embodiments, the outer profile 275 of the implant 260 may be generally aligned with the outer profile of the prepared metatarsal head.

Continuing with FIGS. 32-37, the method may include using a trial device 280 to confirm sizing, placement, and range of motion prior to placing the implant 260. The trial device 280 may be placed over the guide pin 150 and advanced towards the bone 125. The trial device 280 may include a convex outer surface 283 that may generally correspond to the convex outer surface 270 of the implant 260, and a concave inner surface 286 that may generally correspond to the concave inner surface 271 of the implant 260. As the anatomy of patients may vary, the implant 260 may include a plurality of sizes having the same general profile and features.

The trial device 280 may further include a stem 287 that may be shorter than the implant 260 stem 262 and have a smaller diameter than the implant 260 stem 262 such that, when the trial device 280 is placed into the bone 125, the trial device 280 may be lightly engaged with the bone 125 so it can maintain its position, but also be easy to remove therefrom. Additionally, the trial device 280 may include a plurality of holes 282 generally positioned such that they align with the plurality of spikes 274 protruding from the concave inner surface 271 of the implant 260. After positioning the trial device 280, a small drill (not shown) with a cross-sectional diameter generally similar to the cross-sectional diameter of the spikes 274 may be used to drill through the plurality of holes 282 in the trial device 280 and into the metatarsal. The trial device 280 may be made from a plastic material or a metal material and may be manufactured using conventional techniques or using 3D printing technology. The trial device 280 may be inserted over the guide pin 150 until it is secure on the metatarsal head. The guide pin 150 may then be removed from the bone and the joint may be put through a range of motion test. If the joint is too tight (e.g., it cannot complete a full range of motion), additional reaming may be necessary. If additional reaming is necessary, the guide pin 150 may be re-inserted and the trial device 280 may be removed. After the trial device 280 is removed, reaming and/or drilling may be repeated. Once completed, the trial device 280 may be re-inserted over the guide pin 150, the guide pin 150 may be removed again, and the range of motion may be re-tested. This process may be repeated until a desired range of motion is achieved.

Figure 33:
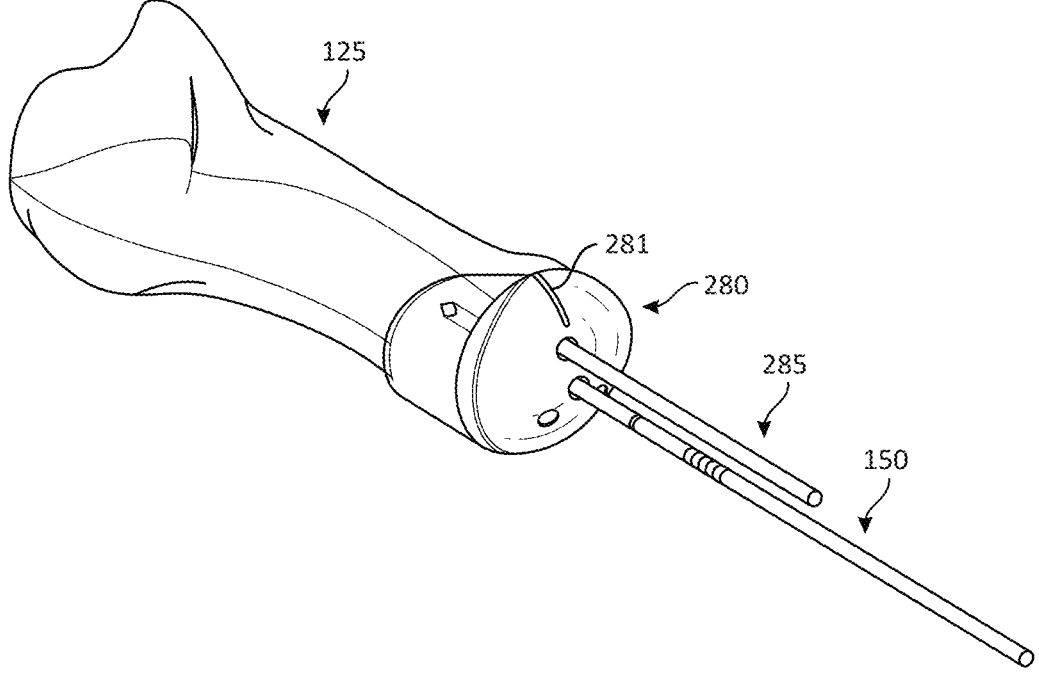
FIG. 33 is a perspective view of FIG. 32 with a second guide pin placed through the trial device.
Figure 34A:
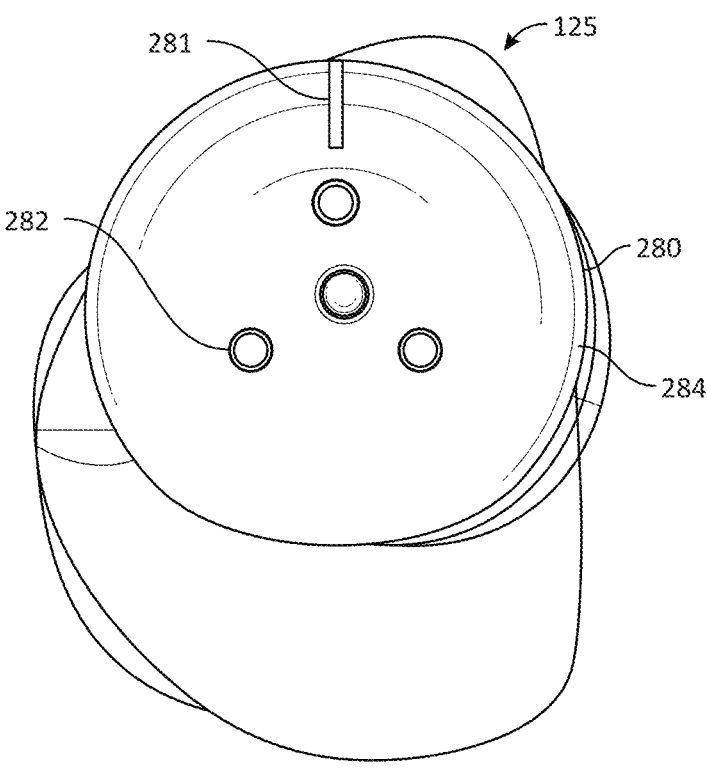
FIG. 34A is a front view of the trial device shown in FIGS. 32 and 33.
Figure 34B:
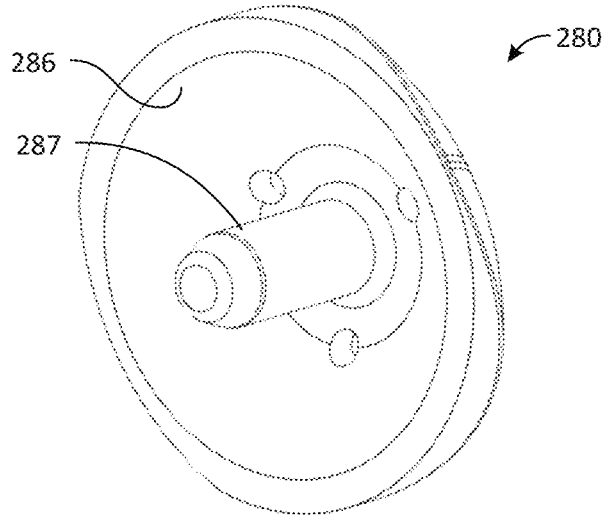
FIG. 34B is a perspective rear view of the trial device shown in FIG. 34A.
Figure 38:
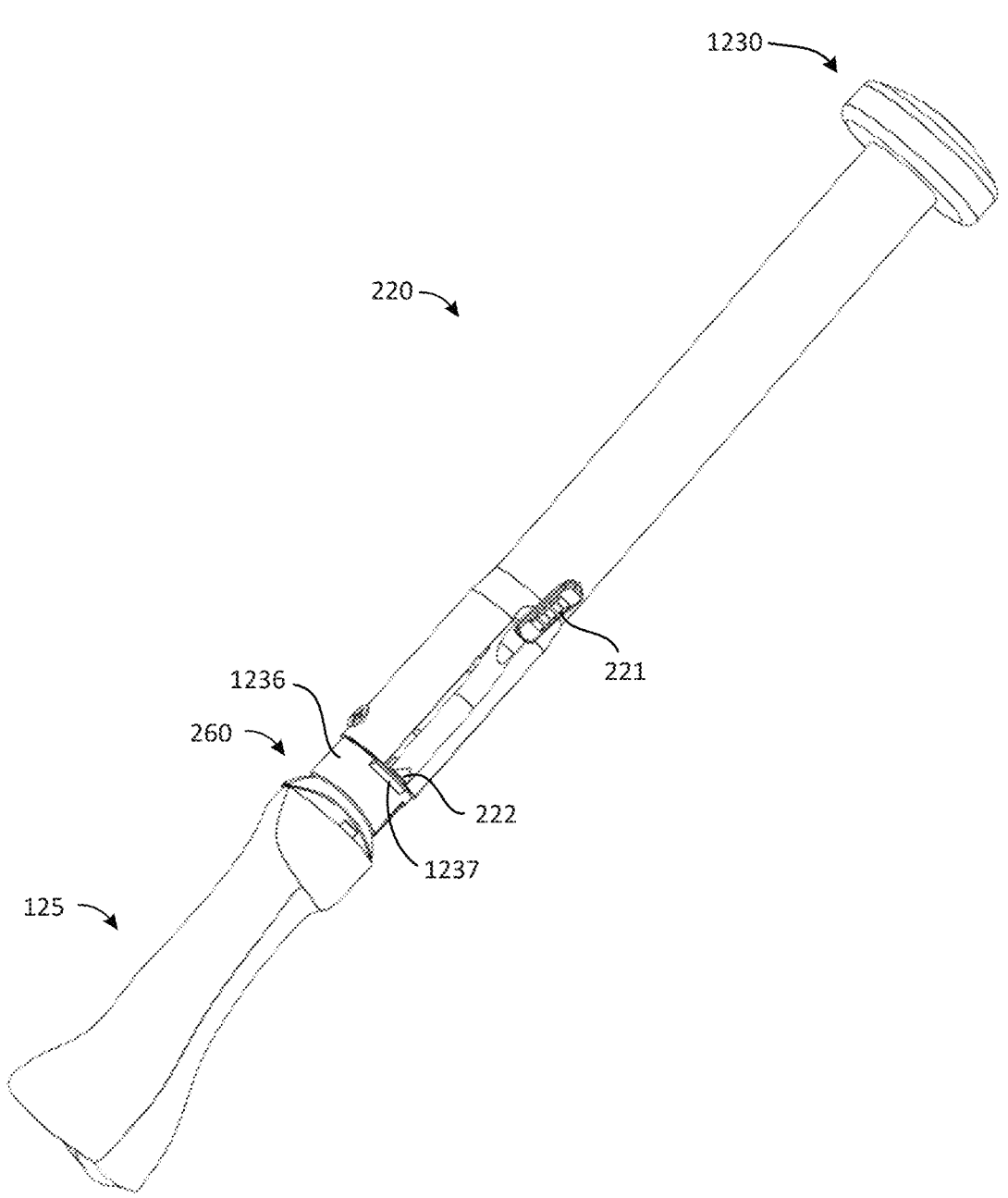
FIG. 38 is a perspective side view of FIG. 36 with the metatarsal arthroplasty implant fully seated in a metatarsal bone and the inserter arms retracted to release the metatarsal arthroplasty implant.

FIG. 33 is a perspective view of the trial device 280 engaged with a metatarsal 125 over the guide pin 150 and a K-wire 285 drilled into the metatarsal 125 through the trial device 280. FIG. 34A is a front view of the trial device 280 engaged with a metatarsal 125 over the guide pin 150. The outer periphery 284 of the trial device 280 may generally correspond to the profile of the metatarsal 125. The trial device 280 may also include an indication mark 281 on the convex outer surface 283 so that the orientation of the trial device 280 may represent the orientation of the implant 260. The trial device 280 may also include a plurality of holes 282 generally positioned such that they align with the plurality of spikes 274 protruding from the concave inner surface 271 of the implant 260.

The method may then include final placement of the implant 260. The implant 260 may be preassembled on an inserter device 220, as shown in FIGS. 36 and 37, and previously discussed. FIG. 35 is a side view of the implant 260 fully seated in the metatarsal 125.

In some embodiments, prior to impaction, the implant 260 may be positioned such that the cross-sectional profile of the stem aligns with the profile in the bone 125 created by the cutting form 201. Partial impaction of the implant 260 may be performed by impacting the proximal end 223 of the inserter device 220 with a mallet (not shown) until the implant 260 is secure in the bone but not fully seated. After the implant 260 is partially impacted, the gripping fingers 221 may be actuated to release the implant 260 and retract away from the implant 260. Further impaction may then be performed until the implant 260 is fully seated in the bone 125. Additional fluoroscopic images in the anterior-posterior and sagittal planes may also be obtained to confirm desired placement.

It will be understood than any feature or group of features described or contemplated herein with respect to any implant may be combined in any fashion with any other implant described or contemplated herein to make any number of different implant configurations. Moreover, any feature or group of features described or contemplated herein with respect to any instrument may be combined in any fashion with any other instrument described or contemplated herein to make any number of different instrument configurations.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles set forth herein.

While specific embodiments and applications of the present disclosure have been illustrated and described, it is to be understood that the scope of the appended claims is not limited to the precise configuration and components disclosed herein. Various modifications, changes, and variations which will be apparent to those skilled in the art may be made in the arrangement, operation, and details of the methods and systems disclosed herein.

What is claimed is:

1. A system for performing a metatarsal arthroplasty surgical procedure comprising a repositioning guide configured to guide placement of a metatarsal arthroplasty implant on a metatarsal bone, the system comprising:
    a metatarsal arthroplasty implant comprising:
        an articular member comprising:
            a convex articular surface;
            a concave bone-facing surface opposite the convex articular surface; and
            at least one side surface intermediate the convex articular surface and the concave bone-facing surface; and
        a central shaft sized for insertion into the metatarsal bone comprising:
            a central shaft longitudinal axis;
            a central shaft proximal end coupled to the concave bone-facing surface of the articular member; and
            a central shaft distal end extending away from the concave bone-facing surface of the articular member along the central shaft longitudinal axis; and
    a repositioning guide comprising:
        a repositioning guide body comprising:
            a first guide pin hole configured to receive a first guide pin placed in the metatarsal bone at a first location and a first angle; and
            a second guide pin hole configured to receive one of:
                a second guide pin placed through the second guide pin hole and into the metatarsal bone at a second location and a second angle to guide placement of the metatarsal arthroplasty implant on the metatarsal bone with respect to the second location and the second angle; and
                the first guide pin repositioned through the second guide pin hole and into the metatarsal bone at a third location and a third angle to guide placement of the metatarsal arthroplasty implant on the metatarsal bone with respect to the third location and the third angle.

2. The system of claim 1, wherein:
    the repositioning guide body comprises an offset guide portion comprising an offset concave surface configured to abut the metatarsal bone;
    the first guide pin hole comprises a central guide pin hole; and
    the second guide pin hole comprises one or more peripheral holes arranged about the central guide pin hole.

3. The system of claim 2, wherein the one or more peripheral holes comprise four peripheral holes arranged about the central guide pin hole and configured to guide the second guide pin into the metatarsal bone at the second location and the second angle, parallel to the first guide pin.

4. The system of claim 1, wherein:
    the repositioning guide body comprises an angular guide portion comprising an angular concave surface configured to abut the metatarsal bone;
    the second guide pin hole comprises an attachment guide pin hole spaced apart from the first guide pin hole and configured to guide the second guide pin into the metatarsal bone at the second location and the second angle to secure the angular guide portion to the metatarsal bone; and
    the first guide pin hole comprises an angular guide pin hole having an oval shape that is configured to guide repositioning of the first guide pin through the angular guide pin hole and into the metatarsal bone at the third location and the third angle, non-parallel to an initial placement of the first guide pin in the metatarsal bone at the first location and the first angle.

5. The system of claim 4, wherein the angular guide portion further comprises one or more angle markings configured to indicate a relative change in angular position between the first angle and the third angle.

6. The system of claim 1, wherein the repositioning guide body comprises:
    an offset guide portion; and
    an angular guide portion,
    wherein the offset guide portion and the angular guide portion are coupled to each other via one or more connecting arms intermediate the offset guide portion and the angular guide portion.

7. A system for performing a metatarsal arthroplasty surgical procedure comprising a repositioning guide configured to guide placement of a metatarsal arthroplasty implant on a metatarsal bone, the system comprising:
    a metatarsal arthroplasty implant comprising:
        an articular member comprising:
            a convex articular surface;
            a concave bone-facing surface opposite the convex articular surface; and
            at least one side surface intermediate the convex articular surface and the concave bone-facing surface; and
        a central shaft sized for insertion into the metatarsal bone comprising:
            a central shaft longitudinal axis;
            a central shaft proximal end coupled to the concave bone-facing surface of the articular member; and
            a central shaft distal end extending away from the concave bone-facing surface of the articular member along the central shaft longitudinal axis; and
    a repositioning guide comprising:
        a repositioning guide body comprising:
            a first guide pin hole configured to receive a first guide pin placed in the metatarsal bone at a first location and a first angle,
            wherein the first guide pin hole is elongated to permit adjustment of at least one of:
                a sagittal orientation of the first guide pin in the metatarsal bone with respect to the first location and the first angle; and
                a lateral orientation of the first guide pin in the metatarsal bone with respect to the first location and the first angle.

8. The system of claim 7, wherein the first guide pin hole comprises an angular guide pin hole having an oval shape configured to guide repositioning of the first guide pin through the angular guide pin hole and into the metatarsal bone to adjust the sagittal orientation of the first guide pin in the metatarsal bone at a second angle, non-parallel to the first angle.

9. The system of claim 7, wherein the repositioning guide body further comprises:
an attachment guide pin hole spaced apart from the first guide pin hole and configured to guide a second guide pin into the metatarsal bone at a second location and a second angle, parallel to the first angle, to secure the repositioning guide body to the metatarsal bone.

10. The system of claim 9 wherein, with the first guide pin removed from the first guide pin hole, the repositioning guide body is rotatable about the second guide pin to adjust the medial-lateral orientation of the first guide pin repositioned through the first guide pin hole and into the metatarsal bone at a third location and a third angle.

11. The system of claim 10, wherein the third angle is parallel to the first angle.

12. The system of claim 10, wherein the third angle is non-parallel to the first angle.

13. A system for performing a metatarsal arthroplasty surgical procedure comprising a repositioning guide configured to guide placement of a metatarsal arthroplasty implant on a metatarsal bone, the repositioning guide comprising:
a repositioning guide body comprising:
an offset guide portion comprising:
a first guide pin hole configured to receive a first guide pin placed in the metatarsal bone at a first location and a first angle; and
a first plurality of guide pin holes configured to guide repositioning of the first guide pin at a second location and a second angle that is parallel to the first angle; and
an angular guide portion comprising:
one or more guide pin holes configured to receive the first guide pin placed in the metatarsal bone at the first location and the first angle and guide repositioning of the first guide pin to a third location and a third angle non-parallel to the first angle.

14. The system of claim 13, wherein the metatarsal arthroplasty implant comprises:
an articular member comprising:

a convex articular surface;
a concave bone-facing surface opposite the convex articular surface; and
at least one side surface intermediate the convex articular surface and the concave bone-facing surface; and
a central shaft sized for insertion into the metatarsal bone comprising:
a central shaft longitudinal axis;
a central shaft proximal end coupled to the concave bone-facing surface of the articular member; and
a central shaft distal end extending away from the concave bone-facing surface of the articular member along the central shaft longitudinal axis.

15. The system of claim 13, wherein:
the offset guide portion comprises an offset concave surface configured to abut the metatarsal bone;
the first guide pin hole comprises a central guide pin hole configured to receive the first guide pin placed in the metatarsal bone at the first location and the first angle; and
the first plurality of guide pin holes are arranged about the central guide pin hole and configured to guide repositioning of the first guide pin at the second location and the second angle that is parallel to the first angle.

16. The system of claim 13, wherein:
the angular guide portion comprises an angular concave surface configured to abut the metatarsal bone; and
the one or more guide pin holes comprises an angular guide pin hole having an oval shape that is configured to receive the first guide pin placed in the metatarsal bone at the first location and the first angle and guide repositioning of the first guide pin to the third location and the third angle non-parallel to the first angle.

17. The system of claim 16, wherein the angular guide portion further comprises one or more angle markings configured to indicate a relative change in angular position between the third angle non-parallel to the first angle.

18. The system of claim 13, wherein the offset guide portion and the angular guide portion are coupled to each other via one or more connecting arms intermediate the offset guide portion and the angular guide portion.

* * * * *